(12) United States Patent
Peterson et al.

(10) Patent No.: US 7,771,931 B2
(45) Date of Patent: Aug. 10, 2010

(54) METHODS FOR DIAGNOSING AND TREATING DISEASES AND CONDITIONS ASSOCIATED WITH PROTEIN KINASE Cλ

(75) Inventors: Randall Peterson, Belmont, MA (US); Mark C. Fishman, Newton Center, MA (US)

(73) Assignee: The General Hospital Corporation, Boston, MA (US)

( * ) Notice: Subject to any disclaimer, the term of this patent is extended or adjusted under 35 U.S.C. 154(b) by 844 days.

(21) Appl. No.: 10/488,292

(22) PCT Filed: Sep. 6, 2002

(86) PCT No.: PCT/US02/28410

§ 371 (c)(1), (2), (4) Date: Jan. 27, 2005

(87) PCT Pub. No.: WO03/023048

PCT Pub. Date: Mar. 20, 2003

(65) Prior Publication Data

US 2005/0172352 A1    Aug. 4, 2005

Related U.S. Application Data

(60) Provisional application No. 60/317,653, filed on Sep. 6, 2001.

(51) Int. Cl.
| | | |
|---|---|---|
| *C12Q 1/00* | (2006.01) | |
| *C12Q 1/68* | (2006.01) | |
| *C12P 21/06* | (2006.01) | |
| *C12P 19/34* | (2006.01) | |
| *A61K 38/00* | (2006.01) | |
| *C07H 21/00* | (2006.01) | |
| *C07H 21/04* | (2006.01) | |

(52) U.S. Cl. ............................. 435/6; 435/4; 435/69.1; 435/91.2; 536/23.1; 536/23.2; 536/25.3; 514/12

(58) Field of Classification Search ........................ None
See application file for complete search history.

(56) References Cited

U.S. PATENT DOCUMENTS

| 5,885,970 A | 3/1999 | Bennett et al. |
| 2003/0017969 A1 | 1/2003 | Tennenbaum et al. |

FOREIGN PATENT DOCUMENTS

| WO | WO 94/18328 | 8/1994 |

OTHER PUBLICATIONS

Peterson et al, Curr Biol. 11(19):1481-1491, 2001.*
Chen et al, TIG, 16(9):383-388, 2000.*
Fisherman et al Development, 124:2099-2117, 1997.*
Peterson et al, Convergence of distinct pathways to heart patterning revealed by the small molecule concentramide and the mutation heart-and-soul. Curr Biol. 11(19):1481-1491, 2001.*

Home-Badovinac et al., "Danio Rerio Atypical Protein Kinase C Lambda mRNA, Complete cds," EMBL-SVA Database Accession No. AF390109, Aug. 15, 2001.
Malicki et al., "Mutations Affecting Development of the Zebrafish Retina," Development 123:263-273, 1996.
Murray et al., "Atypical Protein Kinase C ι Protects Human Leukemia Cells Against Drug-Induced Apoptosis," J. Biol. Chem. 272:27521-27524, 1997.
Peterson et al., "Convergence of Distinct Pathways to Heart Patterning Revealed by the Small Molecule Concentramide and the Mutation Heart-and-Soul," Curr. Biol. 11:1481-1491, 2001.
Rybin et al., "PKC-λ is the Atypical Protein Kinase C Isoform Expressed by ImmatureVentricle," Am. J. Physiol. 272:H1636-H1642, 1997.
Schier et al., "Mutations Affecting the Development of the Embryonic Zebrafish Brain," Development 123:165-178, 1996.
Stainer et al., "Mutations Affecting the Formation and Function of the Cardiovascular System in the Zebrafish Embryo," Development 123:285-292, 1996.
Suzuki et al., "Atypical Protein Kinase C Is Involved in the Evolutionarily Conserved PAR Protein Complex and Plays a Critical Role in Establishing Epithelia-Specific Junctional Structures," J. Cell Biol. 152:1183-1196, 2001.
Yelon et al., "Restricted Expression of Cardiac Myosin Genes Reveals Regulated Aspects of Heart Tube Assembly in Zebrafish," Dev. Biol. 214:23-37, 1999.
Akimoto et al., "A New Member of the Third Class in the Protein Kinase C Family, PKCλ, Expressed Dominantly in an Undifferentiated Mouse Embryonal Carcinoma Cell Line and Also in Many Tissues and Cells," J. Biol. Chem. 269:12677-12683, 1994.
Bandyopadhyay et al., "Effects of Adenoviral Gene Transfer of Wild-Type, Constitutively Active, and Kinase-Defective Protein Kinase C-λ on Insulin-Stimulated Glucose Transport in L6 Myotubes," Endocrinology 141:4120-4127, 2000.
Capecchi, "Targeted Gene Replacement," Scientific American 270:34-41, 1994.
Home-Badovinac et al., "Positional Cloning of Heart and Soul Reveals Multiple Roles for PKCλ in Zebrafish Organogenesis," Current Biology 11:1492-1502, 2001.
Wang et al., "Expression of a Dominant-Negative Type II Transforming Growth Factor β (TGF-β) Receptor in the Epidermis of Transgenic Mice Blocks TGF-β-Mediated Growth Inhibition," Proc. Natl. Acad. Sci. U.S.A. 94:2386-2391, 1997.
Bareggi et al., "Atypical Isoenzymes of PKC, -iota, -lambda, -mu: Relative Distribution in Mouse Foetal and Neonatal Organs," Ital. J. Anat. Embryol. 103(4):127-143, 1998.

* cited by examiner

*Primary Examiner*—Sumesh Kaushal
(74) *Attorney, Agent, or Firm*—Clark & Elbing LLP

(57) ABSTRACT

The invention provides methods of diagnosing diseases and conditions associated with PKCλ, methods for identifying compounds that can be used to treat or to prevent such diseases and conditions, and methods of using these compounds to treat or to prevent such diseases and conditions. Also provided in the invention are animal model systems that can be used in screening methods.

16 Claims, 8 Drawing Sheets

SEQUENCE LISTING

```
<160> NUMBER OF SEQ ID NOS: 6

<210> SEQ ID NO 1
<211> LENGTH: 3437
<212> TYPE: DNA
<213> ORGANISM: Danio rerio
<220> FEATURE:
<221> NAME/KEY: CDS
<222> LOCATION: (143)...(1906)

<400> SEQUENCE: 1
```

-continued

```
gccaggctgt ttatttaacc ggagacggca ctattgctgt ccaaagaata cgtttagttt      60
taaaactccg gtagttttc  ctcgtcagac gatagctggc tagcatcatt agctaagcta     120
gcaggagtac ggatagtcca ta atg ccc acg ctg cgg gac agc acc atg tcc     172
                         Met Pro Thr Leu Arg Asp Ser Thr Met Ser
                          1               5                      10 cac ccc gga gaa aac ccg cac caa gtc cgg gta aaa gcc tac tac aga     220
His Pro Gly Glu Asn Pro His Gln Val Arg Val Lys Ala Tyr Tyr Arg
             15                  20                  25 ggg gac atc atg atc aca cat ttt gag cct tcg atc tcc tat gag gga     268
Gly Asp Ile Met Ile Thr His Phe Glu Pro Ser Ile Ser Tyr Glu Gly
         30                  35                  40 ctc tgc aat gag gtg cgt gat atg tgc tcc atg gac aat gac cag ctc     316
Leu Cys Asn Glu Val Arg Asp Met Cys Ser Met Asp Asn Asp Gln Leu
     45                  50                  55 ttc acc atg aaa tgg att gat gag gaa ggg gat ccg tgc acc gtt tct     364
Phe Thr Met Lys Trp Ile Asp Glu Glu Gly Asp Pro Cys Thr Val Ser
 60                  65                  70 tct cag ctg gag ctg gag gag gcc ttg cgt cta tat gaa ctc aac aaa     412
Ser Gln Leu Glu Leu Glu Glu Ala Leu Arg Leu Tyr Glu Leu Asn Lys
 75                  80                  85                  90 gac tcg gag ctc att att cac gtg ttt cct tgt gtc cct gaa aaa cct     460
Asp Ser Glu Leu Ile Ile His Val Phe Pro Cys Val Pro Glu Lys Pro
                 95                 100                 105 ggc atg ccc tgt cct gga gaa gac aag tct ata tac cgg cgg gga gct     508
Gly Met Pro Cys Pro Gly Glu Asp Lys Ser Ile Tyr Arg Arg Gly Ala
             110                 115                 120 cga cgt tgg agg aaa ctc tac tat gcc act gga cat gcg ttt cag gcc     556
Arg Arg Trp Arg Lys Leu Tyr Tyr Ala Thr Gly His Ala Phe Gln Ala
         125                 130                 135 aaa cgc ttt aac agg cgt gct cat tgt gcc atc tgc aca gat cgt atc     604
Lys Arg Phe Asn Arg Arg Ala His Cys Ala Ile Cys Thr Asp Arg Ile
     140                 145                 150 tgg ggt ctg ggc agg cag gga tac aag tgt atc aac tgt aag ctt ctg     652
Trp Gly Leu Gly Arg Gln Gly Tyr Lys Cys Ile Asn Cys Lys Leu Leu
155                 160                 165                 170 gtg cat aag aaa tgc cat aag ctg gtc aca gta gaa tgt ggt aga cag     700
Val His Lys Lys Cys His Lys Leu Val Thr Val Glu Cys Gly Arg Gln
                 175                 180                 185 gta ata cag gac cca atg atc gga aga atc gat cca ggg tcg act cat     748
Val Ile Gln Asp Pro Met Ile Gly Arg Ile Asp Pro Gly Ser Thr His
             190                 195                 200 cca gag cac cca gat caa gtt ctg ggc aaa aag aac tca aca gaa agc     796
Pro Glu His Pro Asp Gln Val Leu Gly Lys Lys Asn Ser Thr Glu Ser
         205                 210                 215 atc aat cat gag gga gag gag cat gag gct gtg ggc agt cgg gaa tca     844
Ile Asn His Glu Gly Glu Glu His Glu Ala Val Gly Ser Arg Glu Ser
     220                 225                 230 gga aaa gcg gtg tcc agt ttg ggt cta ata gac ttt gac ctg ctg cga     892
Gly Lys Ala Val Ser Ser Leu Gly Leu Ile Asp Phe Asp Leu Leu Arg
235                 240                 245                 250 gtg att ggc agg ggc agc tac gcc aaa gtt ctg ctg gtg cgt ctc aaa     940
Val Ile Gly Arg Gly Ser Tyr Ala Lys Val Leu Leu Val Arg Leu Lys
                 255                 260                 265 aag aca gaa cgc atc tat gcc atg aag gtg gtg aag aag gag ctg gtc     988
Lys Thr Glu Arg Ile Tyr Ala Met Lys Val Val Lys Lys Glu Leu Val
             270                 275                 280 aac gat gac gag gat att gac tgg gtt cag act gaa aag cat gtg ttt    1036
Asn Asp Asp Glu Asp Ile Asp Trp Val Gln Thr Glu Lys His Val Phe
```

```
                  285                 290                 295
gag cag gct tca aac cat ccc ttc ctt gtg gga ctt cac tcc tgc ttc    1084
Glu Gln Ala Ser Asn His Pro Phe Leu Val Gly Leu His Ser Cys Phe
300                 305                 310 cag acg gag agc aga ctg ttc ttt gta atc gag tat gtg aat gga ggg    1132
Gln Thr Glu Ser Arg Leu Phe Phe Val Ile Glu Tyr Val Asn Gly Gly
315                 320                 325                 330 gat ctc atg ttc cac atg cag cgg cag agg aaa ctt ccg gaa gag cac    1180
Asp Leu Met Phe His Met Gln Arg Gln Arg Lys Leu Pro Glu Glu His
                335                 340                 345 gcc agg ttt tac tct gca gag atc agt ctt gcc ttg aac tac ctc cat    1228
Ala Arg Phe Tyr Ser Ala Glu Ile Ser Leu Ala Leu Asn Tyr Leu His
            350                 355                 360 gag cgt ggc att att tac agg gac ctg aaa ctg gac aat gtt ctg ctg    1276
Glu Arg Gly Ile Ile Tyr Arg Asp Leu Lys Leu Asp Asn Val Leu Leu
        365                 370                 375 gat tca gag gga cac atc aaa ctc act gat tac ggc atg tgt aag gag    1324
Asp Ser Glu Gly His Ile Lys Leu Thr Asp Tyr Gly Met Cys Lys Glu
380                 385                 390 gga ctg aga cca gga gat aca acc agc act ttc tgt gga act ccc aat    1372
Gly Leu Arg Pro Gly Asp Thr Thr Ser Thr Phe Cys Gly Thr Pro Asn
395                 400                 405                 410 tac att gca cca gag att ctg aga gga gaa gac tat ggt ttt agt gtg    1420
Tyr Ile Ala Pro Glu Ile Leu Arg Gly Glu Asp Tyr Gly Phe Ser Val
                415                 420                 425 gac tgg tgg gct ctg ggc gtc ctg atg ttt gag atg atg gct gga aga    1468
Asp Trp Trp Ala Leu Gly Val Leu Met Phe Glu Met Met Ala Gly Arg
            430                 435                 440 tct ccc ttc gac ata gtc ggc agc tct gat aac cct gac caa aac aca    1516
Ser Pro Phe Asp Ile Val Gly Ser Ser Asp Asn Pro Asp Gln Asn Thr
        445                 450                 455 gag gat tat ctt ttc caa gtc att ttg gag aag cag atc aga att ccc    1564
Glu Asp Tyr Leu Phe Gln Val Ile Leu Glu Lys Gln Ile Arg Ile Pro
460                 465                 470 aga tcg tta tcg gtc aaa gcc gca agc gtg ctg aag gga ttc ctc aac    1612
Arg Ser Leu Ser Val Lys Ala Ala Ser Val Leu Lys Gly Phe Leu Asn
475                 480                 485                 490 aag gag tcg aag gaa cgg ctg gga tgt cat cct cag aca ggc ttc gca    1660
Lys Glu Ser Lys Glu Arg Leu Gly Cys His Pro Gln Thr Gly Phe Ala
                495                 500                 505 gac atc atg gcc cat cct ttt ttc cga aat gta gac tgg gat ctt atg    1708
Asp Ile Met Ala His Pro Phe Phe Arg Asn Val Asp Trp Asp Leu Met
            510                 515                 520 gag cag aag caa gta gtt cca ccg ttc aaa cct aac atc tcg ggc gag    1756
Glu Gln Lys Gln Val Val Pro Pro Phe Lys Pro Asn Ile Ser Gly Glu
        525                 530                 535 ttt ggt ctg gat aac ttt gat gcc cag ttc acc aac gag ccc att cag    1804
Phe Gly Leu Asp Asn Phe Asp Ala Gln Phe Thr Asn Glu Pro Ile Gln
540                 545                 550 ctc acg cct gac gat gat gat gct gta aag aag atc gac cag tct gag    1852
Leu Thr Pro Asp Asp Asp Asp Ala Val Lys Lys Ile Asp Gln Ser Glu
555                 560                 565                 570 ttt gaa ggc ttc gag tac atc aac cct ctg ctg atg tct gcg gag gag    1900
Phe Glu Gly Phe Glu Tyr Ile Asn Pro Leu Leu Met Ser Ala Glu Glu
                575                 580                 585 tgt gtg tgaacggtcg ctttatccct ctgttactcg catatcatcg ctgcctttat     1956
Cys Val ttgcatggtc gcaatcaatc acacgaaagg aagcaacaag aacctgactt tgctttgttg  2016
```

-continued

```
ggaccagatg aaacagtaac tttgccaaat gtctttcact ttctgccatt tgtaaccact       2076
agtccttaag tgtctatttt tttctcaatt attttttgtat catgttaatc agcagcactg      2136
atgaaaggac atttgtcagt gccttcgacc aacagtttta gctttccgga ctctgcaaac      2196
taaaggaaaa aagaatgact gtgatggtac gcaggacctc ccaatgctaa agatatgcat      2256
tttattttgt aaatatgaaa gagaatcctt tgagcatata tagtaagcca ttttaaaact      2316
ctataccaca tgggatattc ttgaagaaag tttctgatta tctgttttct gtagcgtaag      2376
gatgagaaca ctttgtttta ttactatatt tttatttaag agtactgtca tctatataga      2436
atgtgcacaa tgtgttgaat cagagttttc cagaagttgt tttaagacgg ttggacttgt      2496
ttcctcgttt tagattgaag attgattgga gcagggaaca ttattgaaca ctgttgtaga      2556
tacttacaac tgtgaatgga ggagacattt tctgtataga gaggtgaaaa cacaacagct      2616
ttcttcaatg caggaccaaa ataagacact aaaatgagtg ttcctcttgg cgatctccaa      2676
acagacgagg taaacgcatg ttactactct aactgcagca tgtataaact atttctcgct      2736
ttcttgtttg atttcttgct cttttttcttg tgttaaatgt tatatattgc ctttctggtt     2796
atgatattcc gttgatgtat ttttgcattg aacaaactga gcatcggtga gcattgtttt      2856
tcgatacagt caccgtaaag tggcttcttt cagcccttttt ggggatttca gcctgatca      2916 gatgcatgat gaggtttgtg tttactccac acggcgcccg gttttttgggg tgatgcgttt     2976 tttttaaaca tcatgtctgg acgtgttttt tgtttgtgga ctaaactgaa aggacctttg      3036
accataatga ccaaatgatg acattaaaca ggctactcgt atgcagcatc accctctctc      3096
attccactcc atgcacgctt caactcgctt actatttcac agatgttcac accggtttgg      3156
agctgcgagg atctcgttag caacccggcg ttagaaatga ttgaatcgct taaggccctc      3216
gatgcattcc cagaaaaaag aaaatgatgt gctaatatgc tttaaagaag catcgggggg      3276
ctgaattgga cctgtttttt tcttctctct gtatgttttg tgtattaata tgcacactga      3336
aaaacactat caactgactg gaataataaa ctgtaccact tattttgtta acacctcatt      3396
aaagtattta agaaaatctc aaaaaaaaaa aaaaaaaaa a                           3437
```

<210> SEQ ID NO 2
<211> LENGTH: 588
<212> TYPE: PRT
<213> ORGANISM: Danio rerio

<400> SEQUENCE: 2

```
Met Pro Thr Leu Arg Asp Ser Thr Met Ser His Pro Gly Glu Asn Pro
 1               5                  10                  15

His Gln Val Arg Val Lys Ala Tyr Tyr Arg Gly Asp Ile Met Ile Thr
            20                  25                  30

His Phe Glu Pro Ser Ile Ser Tyr Glu Gly Leu Cys Asn Glu Val Arg
        35                  40                  45

Asp Met Cys Ser Met Asp Asn Asp Gln Leu Phe Thr Met Lys Trp Ile
    50                  55                  60

Asp Glu Glu Gly Asp Pro Cys Thr Val Ser Ser Gln Leu Glu Leu Glu
65                  70                  75                  80

Glu Ala Leu Arg Leu Tyr Glu Leu Asn Lys Asp Ser Glu Leu Ile Ile
                85                  90                  95

His Val Phe Pro Cys Val Pro Glu Lys Pro Gly Met Pro Cys Pro Gly
            100                 105                 110

Glu Asp Lys Ser Ile Tyr Arg Arg Gly Ala Arg Arg Trp Arg Lys Leu
        115                 120                 125
```

```
Tyr Tyr Ala Thr Gly His Ala Phe Gln Ala Lys Arg Phe Asn Arg Arg
        130                 135                 140

Ala His Cys Ala Ile Cys Thr Asp Arg Ile Trp Gly Leu Gly Arg Gln
145                 150                 155                 160

Gly Tyr Lys Cys Ile Asn Cys Lys Leu Leu Val His Lys Lys Cys His
                165                 170                 175

Lys Leu Val Thr Val Glu Cys Gly Arg Gln Val Ile Gln Asp Pro Met
            180                 185                 190

Ile Gly Arg Ile Asp Pro Gly Ser Thr His Pro Glu His Pro Asp Gln
        195                 200                 205

Val Leu Gly Lys Lys Asn Ser Thr Glu Ser Ile Asn His Glu Gly Glu
210                 215                 220

Glu His Glu Ala Val Gly Ser Arg Glu Ser Gly Lys Ala Val Ser Ser
225                 230                 235                 240

Leu Gly Leu Ile Asp Phe Asp Leu Leu Arg Val Ile Gly Arg Gly Ser
                245                 250                 255

Tyr Ala Lys Val Leu Leu Val Arg Leu Lys Lys Thr Glu Arg Ile Tyr
            260                 265                 270

Ala Met Lys Val Val Lys Lys Glu Leu Val Asn Asp Asp Glu Asp Ile
        275                 280                 285

Asp Trp Val Gln Thr Glu Lys His Val Phe Glu Gln Ala Ser Asn His
        290                 295                 300

Pro Phe Leu Val Gly Leu His Ser Cys Phe Gln Thr Glu Ser Arg Leu
305                 310                 315                 320

Phe Phe Val Ile Glu Tyr Val Asn Gly Gly Asp Leu Met Phe His Met
                325                 330                 335

Gln Arg Gln Arg Lys Leu Pro Glu Glu His Ala Arg Phe Tyr Ser Ala
            340                 345                 350

Glu Ile Ser Leu Ala Leu Asn Tyr Leu His Glu Arg Gly Ile Ile Tyr
        355                 360                 365

Arg Asp Leu Lys Leu Asp Asn Val Leu Leu Asp Ser Glu Gly His Ile
370                 375                 380

Lys Leu Thr Asp Tyr Gly Met Cys Lys Glu Gly Leu Arg Pro Gly Asp
385                 390                 395                 400

Thr Thr Ser Thr Phe Cys Gly Thr Pro Asn Tyr Ile Ala Pro Glu Ile
                405                 410                 415

Leu Arg Gly Glu Asp Tyr Gly Phe Ser Val Asp Trp Trp Ala Leu Gly
            420                 425                 430

Val Leu Met Phe Glu Met Met Ala Gly Arg Ser Pro Phe Asp Ile Val
        435                 440                 445

Gly Ser Ser Asp Asn Pro Asp Gln Asn Thr Glu Asp Tyr Leu Phe Gln
        450                 455                 460

Val Ile Leu Glu Lys Gln Ile Arg Ile Pro Arg Ser Leu Ser Val Lys
465                 470                 475                 480

Ala Ala Ser Val Leu Lys Gly Phe Leu Asn Lys Glu Ser Lys Glu Arg
                485                 490                 495

Leu Gly Cys His Pro Gln Thr Gly Phe Ala Asp Ile Met Ala His Pro
            500                 505                 510

Phe Phe Arg Asn Val Asp Trp Asp Leu Met Glu Gln Lys Gln Val Val
        515                 520                 525

Pro Pro Phe Lys Pro Asn Ile Ser Gly Glu Phe Gly Leu Asp Asn Phe
530                 535                 540
```

-continued

```
Asp Ala Gln Phe Thr Asn Glu Pro Ile Gln Leu Thr Pro Asp Asp Asp
545                 550                 555                 560

Asp Ala Val Lys Lys Ile Asp Gln Ser Glu Phe Glu Gly Phe Glu Tyr
            565                 570                 575

Ile Asn Pro Leu Leu Met Ser Ala Glu Glu Cys Val
            580                 585
```

<210> SEQ ID NO 3
<211> LENGTH: 71843
<212> TYPE: DNA
<213> ORGANISM: Danio rerio
<220> FEATURE:
<221> NAME/KEY: misc_feature
<222> LOCATION: (1)...(71843)
<223> OTHER INFORMATION: n=a, c, t or g

<400> SEQUENCE: 3

| | | | | | |
|---|---|---|---|---|---|
| aagctttaca | ttgaatagag | cagaaggaaa | gagcatgtcc | tcactcggac | acctgccagg | 60 |
| tttttatttt | tatatataca | taagtagcct | aaatatgcac | ttgtcatctg | ttaaaattca | 120 |
| tccgattaaa | catttgtatg | tattattagc | atttcgacat | ttatctgcgt | atatacagtg | 180 |
| catccggaaa | gtactcatag | cgcttcactt | attccacatt | ttttgttaca | gatttattcc | 240 |
| taaatggatt | aaattattgt | ctcaacattc | tacacacaat | agcccataat | gacaatgtga | 300 |
| tttttttttt | aattgttgca | aatttattca | aaataaaaaa | cctgaaaaat | cacatgtaca | 360 |
| taagtatttta | cagcctttgc | cgtgaagctc | taaactgagc | tcaggtacat | tttgtttcca | 420 |
| ctgatcattc | ctgagatttt | tcagcagctt | aattggagat | cacttgtggt | aaatttagtt | 480 |
| gatttgaaaa | cgcatacacc | tttctatata | aggtcctata | aagggttga | tagtgcttgt | 540 |
| caaagcacaa | accaagcatg | aagacaaagg | acctgtcttt | ccggatgcac | tgtagctgtg | 600 |
| agcagatttt | tttaaaaaca | caaagacatg | catttcatct | tcaaacttgg | aaactctgcc | 660 |
| tactgagaaa | tctcccaggt | caaaaatcct | ggatcatata | ctgatgataa | ttatcgggtc | 720 |
| taactcttct | tcagactgtg | tttctctctc | tctttccaac | acacagttgc | tgaattcatc | 780 |
| cactcgagcc | agatcaataa | ttctcctcaa | tcactctcac | tctctcccat | aaacacacac | 840 |
| tcagtggcct | ccgctcccct | tatgtaaaca | gagactgatt | aggtcattct | gctgcttatt | 900 |
| ttgagggctt | gcgttgcatc | tactggagtc | tctgatattt | acactggagc | agacctggag | 960 |
| ctcaacaccc | tccatcaaac | agacaaaacc | gcgaggctct | tccacctctg | acctttcatt | 1020 |
| acccttcaat | atcttaccaa | acacatgctg | gatgaagata | aagctccaaa | gacacaatgt | 1080 |
| catgctaagc | aaattcctga | aaatgccatg | tttgcagagg | tcagacaggg | agtataaaat | 1140 |
| aaagcagaaa | tctttgtaaa | actggactga | aggcacagtc | atattaatcc | ttttctgcta | 1200 |
| aaagaaaaaa | aaattaggaa | gttaaattca | gtaatcttaa | caggaaatca | tgcaatcagg | 1260 |
| tgttatttgg | ttggaaagtg | acttcagcgt | gtgcgatgct | ttatttactg | cttttttgaat | 1320 |
| ataatattta | gtatgtgtat | tttgttaata | actgaacaag | tacacaaata | catgatggta | 1380 |
| tgtgtgtggt | atatggtatt | aggcagtggt | tagaaatcaa | ctgtaagaaa | catctgatca | 1440 |
| taaagatatg | attatatttg | ttgaagcttt | acaattcaac | gctacttcaa | gttacatctt | 1500 |
| gtcttgctta | aatttaccat | taaaaggtcc | aatgagatta | agcgggcttt | tacacttggt | 1560 |
| tcaattgcct | ggaccgaacc | taagttccat | tgccccccct | ttgccacctt | ctctgctggt | 1620 |
| ttgtgttcac | acagtcttttt | ttccttctga | atccaggtac | acttgcatca | aagagcatag | 1680 |
| aataactaag | cggcgacact | agtgtgattt | gggaaactcg | ccgcggcatc | tagtgtctca | 1740 |

```
gcggccattt tggaatgaaa attccaatag aacaagtctt tagcatatta taagtctgta   1800
aaataaacta ttaaaagtgt tgatgattgt gttagtaagt gttatattgc catctttcag   1860
gttcaatgtt aatgcgcttt ttaaataaat aattaaaaaa caaagcagct gcttgccatc   1920
gcgacagcaa aaagaacaaa tcgatggacg attacttttt ctccaaaatg gcagaatagt   1980
aggaggatat ctaagttagt gtgcccaaaa cagtgacaaa atttgcattt agaagatata   2040
aagctgatat aaacatgtaa agcttgtaat ttgtcacttt cacatatata gagcaaattt   2100
cctttgttgt tttacaaagg ggaggagcta atccatgtcc cactctctct tcgtgttttg   2160
gttgaaataa cgtcaaacat caaataacaa tgcacgtttc gaaacaattc aagtcagtgt   2220
cagtttcact tttaattaca attatcatca ccatatatcc agtcaaactg gaggaccaga   2280
actagttcaa gggtggtagg actgggcgat taatcgttaa gtagtcgaaa tcaacattta   2340
aaaccactaa ttgttttaca catttttgaa tgccttgaga cagcatattt tccattacaa   2400
taaaatgatc atttattcaa aaagattcaa aacttaaata ttatttacag gatacagata   2460
ggttatttta tttagaagag atgctgctta ttttatactt tgaatatgaa aaacgttgaa   2520
aataattcat tttgtttcca aaagagcaag ttatttattt atctttattt tttataagtt   2580
ttaggcaatg tgtgttttaa tttcagttgt tcaacgttga agttcaataa ataatcagag   2640
attgtagctt gtgcttcgtt cacttatttt gaaatcaagt aatgcgccct tcattcaaaa   2700
atctcttgtg atatgtgagc ttatttaccc tataaaactt aaggaactat ggaggacaaa   2760
aaataaaata aataaacgaa ataatcgttc atcaatcgta atagagttaa aatgttcaat   2820
taatcaacat ttgaggccaa atcgcaccag ccctaacaag tggtgtgtct cacatgacta   2880
aatggaaaca gcaaagcaaa gcaaagcaaa aaaaaaaaag gaaatgcagc tattagatag   2940
gaagcaaaaa atcaaggggg gtaaaaaatc tgacaacgaa ggtatgtcag agatgaggtt   3000
tgcggttcga gctacaggat ggcagaacaa aatacattag gcaggaaaat gacaggtttt   3060
ctttcacaga tttaaaatgg aaggaaaaaa aactgaaagt ggaaataaga gcacgatagt   3120
ggaagaatta gcctcctcgc ctgaggtgca tgaagtcact gatttcacaa ttacaaaagg   3180
aagacagaga gacgcaaacc gagaaagaga gagcgaaaga ggaagagaga gagaggcagc   3240
tgtctggtgt ctgcaccgca gtcgctgtct catcctctgt gggagatcga caggactcca   3300
tctgtctgcc agacacgtct acacggcaca ccagccctca aaccattaca gctgcatgtc   3360
tatcactgtc gtacaatcaa acaaacacac atgagctaac tgtatgccac ctaagtggga   3420
agactaggac agctaaatta atgggatcat gaaaactcca agtacaggca catgcccaaa   3480
tgactgcgtt cacaccaaag gcgtcgagag catccaagta gctggaaatc attctttttc   3540
aatgggagcc tgcagcgata agcgacaagt cttcacggtt gtgggcgtcg aggagagttg   3600
aaataaagtc aacgttatag taatgtgctg tgatgcagtt cagtggcaac caatcggaac   3660
aagtcatgtt caagtccacc gcttgagagg agtccagaga acacagtcct gtgaactttg   3720
gttctgacca cagttgttcc caagggtttg attattgcgg ttactggatt tccaattatt   3780
tacaaagttt tcttttagga aatgcgtgat gcgcattaat ttttggttt tttccctta   3840 aaaaaaaagc aggtatctca tgctaactac aacaacttaa tattttcgac atatggacac   3900
atattggata agtggagcaa aaccacacca catgaaacaa cttcattttt agttgttaaa   3960
ttaatttgat aaaagggaca caacactttc acgctagaaa gcatgttctt ttaatgtggg   4020
attgtaactt taaatacaag attaatgtag tgaattctcg cggccggagc tgtaaagtca   4080
gacagcgttg tcgccagggt ggccagagtg aactttgaca cactcgccac cctcggtgtg   4140
```

```
aatgcacagt gacttgcatc gttttttgaca agtgccaagc agactactga aatcatttta    4200
gaaagaaatt ctaaaatcaa tctaaatata aactggggtg agaaagctaa atatatttgt    4260
gtttggtaaa taggaaaaaa aagcagtgcg acaagtgttc caatagtgtt tcttgtcagg    4320
tggtccctat atagcatatg agccttaacc actcgtgctc tattgacctt attgtaaaat    4380
gcggaagtgc gcctgttttg acgattgttt tagaaattac gattcagtcg cctatgggag    4440
aaatgactag gaataataaa cggcagaaaa cgatcaaact acttgctcta caaacaaatg    4500
tttgcatgac tatacagacc aagtagaata atataataag aaaatatcag gtttgcaaca    4560
tcaaacagcg aaacgagcag ttttttaatgt ctaaaaataa atggaagtga atgagactgg    4620
aagtctcaag ccaaaaagat tcaaatggct gcgccactcg tcggccaaga ataaggtgaa    4680
tagacaccct aaccgaatac agcgcttgac aacacaaata aatacagact tacaaaaaca    4740
caaaaactgt ccaagaaggt tcctgcgctg aattctctgg agcagcagct gtgcatcaaa    4800
acctagccag gcagcatctt taagcatgca catttcacca aaatgaatac aaaaataact    4860
ggacatctct taagttctaa aactaaatat tttttacttc attattattt acagcaaaat    4920
cctctaagta aaattcactt agtttagata gtatttgctt cttctctaaa ttaaattaaa    4980
gttatacaag ttaatgagac aacgaaagga ttaataaggt gatgattgtg cactgatgat    5040
gaacacctgc tgttaataaa caaacacaaa gagaaacaca aaactacaac tgacttcagt    5100
cacagccttt gataaaatca actgaaatat aaaagattga atctctcaaa atctcagcag    5160
aggatcatta agcaactcaa caaagagcaa ctttacttat aattgtcctt tgagggacca    5220
aatgctctct gaactgagta caatatactc agaggaattt gctgtgtaat tgtaattaat    5280
atgttattat tgttgctatt tgagggatat ttaaatcacc aattttctca gaaatatgct    5340 ccatttgta gttttactaa gcttttgat aatgctctga aaacaaatat atatatatat    5400
atatacttat ataataata agcaataaaa tcttaaaata tttcaggcat gtttcaaaat    5460
ctagcgatct gtcaacctag gttgaattta agggccttat agactatgcc accagaatat    5520
gccacctcct ctggtcaact cactagtttt aaaaaaccca gccagtgttt ccaaaagcac    5580
agcagacagg ggagtcagtg tccttgataa agtggaagag gactgcatcc gagcagactg    5640
aagtgccgtg tgctgaagtc ttgttatgag ggtctgatcg tcaccaacat ccacgcggac    5700
acctgtggaa actctgagtc acttgttctg ccgctccggc atcacagatg tttagagtta    5760
acatttcacc cagtaaactg atgagcctgt ctgccctgct tcccgtacac acacacacac    5820
acacacacac agacgcccgc ataacagtga cttcttgatt tggacaccag cagaagagta    5880
tgcatatgtt gtttctcttt agcggctaga cccgtgtaag ctcagcgtct aggtaatgac    5940 cttctcacgta agcacatatg cctgtttacg gttcctccaa aacagtttaa caaatcttgc    6000
aagcgcctgt gtacttgaca ccacttcaat cttaagcagt gattgttaat ttaaaagtga    6060
ggaaaaaagc gagatacaat ttatgtttta aaaacttttc tgccttggca ataaactgga    6120
acaagtaagt tgaagacaag tttagcagtt gcaaattta gttggaagtt attaatagaa    6180 tattttgaa cattgtttta gtaatctgtg aattaatagt aattgtgaag ttaagaaatg    6240
ctttattttt atttttagtta gtatatttac tttaaaagca aagcaaagat gggaaatatt    6300
agcttaagtg ttttttgcaat cttattttta aatattttaa tttaatctta cttaatttgt    6360
aaacttatca gatacctaga atttaataaa attttattgt tgtatcacaa ataggcatga    6420
gacgataacc attttcaagg tataacacgt ttggaaattt ttttttagga caacagtatc    6480
```

```
tccagcagaa aatatatcca agatgccgtt ttaaatggta aagggaagaa acaaagtttt    6540
agaaacaaat taaaacagaa gtcaaggaat catttgaatt atttaccctg acatgtttac    6600
tgctctaaaa tattttaaat gtctcttaaa atataatata atataatgta ttcaaaggag    6660
aaaaaaaaac tttcagtttt tacccagaca tttaaaaaga acgtattta gagcagtaat    6720 cacaatacag tcaaagcgtg atgtttttat ctaaggttat cataccgtta gaatcttata    6780
ccggcccatg cctaattaca aggaaaacat agcgtgccga taaattgtaa aaatcataaa    6840 taattttaa aacaacatat atttgtgtat gtaagatcat aacgttaaaa aactgtgtta    6900
gaacatgtaa aacacaataa aaggtattgt ttatatgaaa atgaaacctt ttttttttt    6960 ttttccactg aacgcaaaaa aatacatttt caagaaattt tcaagaaaac cttaaaccat    7020
tcacttctat agcaggaaaa acaaatacta tagaagtcaa tggttacaag gttttcagat    7080
atctacaaaa aaaaaagttc cactgttttt aatatacagt gctcagcata taactaga    7140 cccctcacaa atctatcttt caaatttata attttaatat aaagctatac aatattat    7200 ttatgcataa tacattagat tagtcagtac tgaagccaaa tttggaaatt atctaacaaa    7260
ataacttacg ataatgatac aaaaacttgt acacccaaac acatatgtta tagagaaaca    7320
ttaaatacaa attttaaaat gaggaaaaat caagagaaga aaaaaaattg aaaaaagttg    7380
ttgatatatt gtagtttgta cattttttt ttttgcattt tttttgctt gaatttaact    7440 gtattatctt tcaattacta aattggtttg gtgactaaaa tactattta ataaacattt    7500 ctgtttaata aatctgtttt gtttaaatgc accaaaatac attgcctata ttcaccgaga    7560
tgtgaataaa attattgatt gtcaaaatgg ggtctactca tttatgctga gcagtgtaaa    7620 aaataaaacta aagacaggtg tgaaataagt gaagggtgag taaataagga cagaatacat    7680
ttttgggtga actatcccttt tttgggtcat tgcatcttaa aataaaactc aaagttaaga    7740
gcttacagga agtaaaaaaa aaaaggaaa aaaaaagcat gaagtcaggt gcaagacact    7800
gccagacagg gacgtgtcgg gagttcggca gttaacagct cgctgtgcaa agagcaggtg    7860
tcagtgactc actcgtgttt ctgggagttt gatatctcac cctcagctga gcggagcaga    7920
gacgctctca ggggaagttt agcgtgtgcg tgtgaatcaa tttcattagt gtgcgttaag    7980
cagaagtgag ccgagagtta cagtgtagct ggctgtttgt gtgtcagggt gaggtcagtc    8040
tgtgtagcag atgtgactgt atgactgaca gactcaaggt ctgttttagt acatgaagtg    8100
tgtgttgggg gagggtggaa ggaggaatgc ggtttgggtg ctagacgaga caccagacgg    8160
tatttccggc acacttgcat aagcacacag gagagactga ggcttttctt ccgcacacac    8220
agacagaaca caatcatttg ctctcgtcgg aacggaagaa aaataattgt gtgtgctgga    8280
acattacagc acagttaaac cattaactgc tgccacttgc attcgaaaaa gaaaaaaggg    8340
actctggcag caccgacagg gggtcaatct ttgtctaaca tgagcacaaa aaactagaaa    8400
agctctggct tggtcaagtg ggtcatgaga catggctggt caatgggagg gaaacaatcc    8460 agatctttt ttgcactagg ttgacctttc tatagattct acagcacgag gacactttgt    8520 tgagtttgt ttcaaaggtt gcattatgaa agtggaagaa tctccagtgt tctgcttttg    8580
gattttgcaa ttacacaatg caggaatttc cccatctaaa gggacaaatt cacagatggg    8640
aaaatataga actttatttg tcaacactga tttcctgtca gtgtgcaaga ttttcgaaac    8700
attgtagccg ttgcagatta ggcatgggac aatgacattt tgaaatgaat ttttttttt    8760 ttttactttt ttgggaaaac agtatctcca gcagaaaaga tattcaacga tgctgtttta    8820
aatttaaaat gtaaataaat tttaagagta atgaaaacag caaaagtcaa tggttcattt    8880
```

```
gaactattta aggctgattt atacttctgc gtcaaatgca cgcgtatgct acggtgctga    8940
cgcatagccc ttcaccgtgg ccgttggcga cgctgacgtg cacctctcaa aaaatttaac    9000
tacacgtggc aatgacgctt agcgcaagct ctgtgattga tcggcttggt agcgctgacg    9060
agtctgggtg ggaccgagag ccgcgcaaat ggtgcgagcc tgatagagcg attgtttaca    9120
agtgtggagt tccgtgaagg agctccggat ggaaagtttt gttttgtgtt tacctcatag    9180
ttaaagttgt tgtacgtccg ccagttcctg cctctaaatg agcgagtttg agccacttgt    9240
acatccccga agcgttcagg aaaagcaaaa cagtgaagaa actcgacaaa gaggaacatt    9300
tacacctcac tgccaactag cgtttcggaa gtgttaatgc agatcaacag agacagggcg    9360
cagacatata aatacacagc tacgcgcgtt acatgcgccg tgggttacgc aggtcacttg    9420
acgcagaagt ttaaaccagg ctttagccta acatgtttat tgctccaaaa tattttaaat    9480
gtttctgaaa acaaaatata ttggctaaaa tcgcctacta ctcagtaggt actgcatctg    9540
aatttaaatt tacaacccga caaaaacgga cgttctatac agtagtaatg tggctagtat    9600
gaatggagct tggacgtagt acagatgcca ttttgtcatt atcacgtgac atacccgctt    9660
cactcccatt cataaattct ctaacggtgc atcatgggat agcgtagcgt ccatcggata    9720
cacacttcag aatctcaccg cactctaggt catccggata cttctcacat actgattttc    9780
gaattctatg aattcaaaca tactactcgg ctcgcatact gttttagca tatggaagta    9840
tgtgattttg tacggatcca ttgtgttcaa agcgaaaaaa aaacgttgtt gctttactca    9900
gacatttcaa aagatttttt tagagcagta atcacaaac tgtgaaacca aaccatgata    9960
tttttatcaa aggttaccat accgtctgaa ttttatatccc acccatccct attgtagata   10020
aaatactaga agtaacaaag tggtatgtgt gcagaaaaac actgttcgtg atcatttagt   10080
acaatctcag actggaaatc agaaaaaagt tatttaaatc catttccttt aaacttaaca   10140
ttgccactag atagactaga ttaaatacaa aaatatatat tattatacat tatattctta   10200
tcatctcatt atgcatatat taattaagga ttttggatgg aaagggtaag tgtaaaactg   10260
ctgttgcata tttttttaatg ctttgaatat ttaaatacag atttttgaat tgcaatttat   10320
aagaaaaata aatacaggta ctagaaaacc ttgaacatcc aaggtaacaa aattccacca   10380
ttttaatgtg tgctgtcatc attcacccc taaagctgac cctgtactga cctgagagga   10440
agataatgta cttccccttc agccagacca actggaattc cctccctccg gccatacgtc   10500
ccaaccaagc aagcgtcacc tgctcgtgcc accccataaa atgggtcag cactagttta    10560
tcaaaacaac tgcagccttg cccagacaat agcaaacagt ctcctctgcg gactatcaca   10620
cattaccatc tggtcacaca cgtgcaaatc cacttgtgaa catgaagcaa aacttgacct   10680
tagtgaacca gaacacatgc aagacaaaaa gacgcttact ttgtccagag gcctctttag   10740
ctggtagtga aacttctcct tcatctcgtc cagcagctgc ttgagctgtg gctcctcctg   10800
tgtgccctca tgcttgcgcc ccagctgaag gtagcagggc acttggctg aatcgaagcc    10860
ccagtggcag gtcctcttgt caggggactt gtgtgagtgc attacaaagt tctgtgggga   10920
aaacagcagc tggcactcca tgcactgaat gcaagggca tccggctgga cgtagaaatg    10980
gggcacaaac aggccttggc acttgccaag acactggtgc tccacctgga aactggcgtc   11040
actctccttc agcaggcctt ggcctggcag tttgctgttg ggatcggctg agatggtggc   11100
acctgggcga agcagggcat tgcagagccg ttgggcatca gttagggtaa tcaggccaca   11160
ggaaggtgca ttaaaaggca aaatgcccag caccttgaga atgtgcagct gctccgcatc   11220
```

```
acaccgcgaa cagtaaacgt aaagttcatc acaaacagca ttgatctgct gcagagagaa    11280
gtctcggagc actgaattga gtacctgggg cagacaaaga cgcttctcac cacctacaac    11340
aaagcaggag atggactctc cttcaaggag agaatgggta agctctgtgg agctgtcaca    11400
gggcactaag agtgggcctc ctccgaggac tgggggagac ggtaggggag ccatgccagc    11460
aggagaggcg cactcctgtg ccgatttttgc tgagaaagca gcaggacctc ccagggagct    11520
ctggctgctc agcgtgaact gtgccagcgt gtgcttgagg ccggcgctca gatctaaagc    11580
cttggatgct ccgacaatgt ggaattctct ttcctccatg tccatttctg agctggtgtg    11640
ctcctcacgc tccttcttga cctttagggg tttggggatg ctctccaggc tgcgacgttt    11700
caaatgcatc tctgccatta cccgttttttt aatgggagca tcttccagtc gctccctgta    11760
cagcctcttc atgttgcctt taatgaggt caggtctta aaaggggttt tcagacctgt    11820
ctgagggctg gccatatcca ttcacagata actggtcttc cttgggtgga aaataatcgt    11880
cagacacgac acctttgggt tggtcctact ttgctcgctg tgttaaaggt tgcaaatcct    11940
tttacgtcta gctacatgca tgatgctgac agaattaaat gttcaacgag cttcctgtga    12000
atgaaaaggt aaaaaggctt gtattaaaat ataattctta ctaaatcaaa cacaaatcag    12060
aatgtgaagc cacgtgaatg cggatgaatg gaaaatgctg ccagagcaat taaaaggcat    12120
ccagaagcgt tttagcgttg ggcacagtgc taaactagac gacagaaaca ttttcacctc    12180
atcaggataa tctaatttga aagcaatcga tctaaggcca gtttctcgct ggtttagtgc    12240
gctgtttttc tctactgaca acatgccgaa tccgtcaagg cggtaaatga gtcagtgcac    12300
taataacgtc ggtttaacac acagataacc aacagcatca gtaactaaca gcgagcagcc    12360
atttagtcct gtccaaccac agcaggcttg aaacaaaatg tattaacgac acataaacac    12420
cacttctgcc acgcaagatt aaatgtattt attatattgt aaataaaaaa ttatgttttc    12480
atcgtacaag caaaagcctg aactggcgga atttccgagc acgaatatga aggcaaaatg    12540
aaagctcagc ctcaaattca gcgcatgcca gtggggtatc ggcaaaatcc atcagaaaaa    12600
cgcgtttaat ttcagaatca caacatgcgt ttctgttcta caaacggaat gcattcattt    12660
tggcgaaaat taagggcca ccaaagcata ataatctcaa gttcctcgaa ataaacgctt    12720
ggttttgctt taacgttacc agatttgcgg gtcaactcaa acagactgac cctgaccgca    12780
gacgtcgttt catttcctca taaaataacc agtttccaga aacactggca aaacgcggtc    12840 tattttttaac cctgaatgac agcgtctctc ttttttacccc cgcaaggaca ccgcggctct    12900
gtccccgcct ctacccgtct ctccccctctc cttctccggg cagagctgcg ctgagcaccc    12960
gcggtgtgac aatcaccatc cccgcaatcg ggaaaaccct tcacatgaaa aaaaaaacct    13020
gatcacggct attacacctt aaatatccca acacgacatc taaagcttct atttaaaatc    13080
cattcccatg tcttcattcg gcagtgaaaa cgtttgtcaa ccattcagcc agtctgacac    13140
ctgaccaccc cctcaaaata cgttaaacag cgatatcccc aaaactgttt ttgaaaaaca    13200
gaaatacaga catttgtatt aaacacaata tagatcatat ctaagattta aatcaatcac    13260
acaaatactc ccagctcgat caccaatatg accaggttaa acacataata cacacgtata    13320
ttatgccctt ttaaatggca catcaaaagc accaaaagca ccaaaaccgg tttaacatct    13380
gaaaaactgg ctcgttcgca cagacagctt tagcagtgcg gctagaatat ttagacccett    13440 tagcacgcgc taaccgagct aacgctacaa atcccgttc agagacagaa ataaacgtca    13500
cttaactatt acaaaccttc aaaacggttt taaaaaacac agcgacaaac tgctgaacca    13560
ccagagtaat ggacgcagtg tataggcgaa tcagatgtgg gttttaaagg gacttgcctc    13620
```

```
aggatgaacg atctgctctg ctgtctctct cggtctctcc tctagtctgt ctgagcgtca   13680
acaacacgcg cacacactca aagccttcag acagatcgcg cgtcacacac agcgagagcg   13740
cgcactggcg gagcggatga tgttgcgcgg gcgtgtctat gtatgtgtgt ctgtctgtct   13800
gtctgtcctg tctgtctgca gcgcgccgcc agattctcat gaactttgca agaatttaca   13860
ggttacagta aatgtaatgt aatgcatgta atacatgttc agttgtcatc tgtggtctac   13920
tagtaacttg cgcttgcaca catgactaac caagggacat ttctttagaa ataagggagt   13980
tttgctgtct acttagggac agtcatagtg gagcatgctg aatttgaatc actttatggt   14040
aagagaaagg agtaaatgga aattaaatag taactttagc cacatcccca ttcacgctat   14100
gacttagcat gattttttgag gaataatgaa tggcagcatg agctgaggtc tgtcaatgtt   14160
tcacagataa tgactcatct gaaatgggct gtttaaatga atacatatc atgcaaaaca    14220
tcacagtttt tgtacttggt aaagacataa aacattattc tgttttacag aattatagtg   14280
ttgagggcgt aacacattac aagtaacgag ttacgtaata atattacttt tttaagtaat   14340
gagtaatgca tattttttaaa aattaagtaa tactatttga gtgactttt agcttaatta   14400
attagcttat aaaaacaaat ggctgaaata aaatcaatgt cagattgaat cccacactca   14460
atgatagaat gcaggaaaag acagaaacca acatggcaga gccttatatt tctgcaatgg   14520
gagttttctt attattctga acgaatcaca gaaaaggaaa acaggattat agtcttaatg   14580
gatagtgatt ttactttatt aatagcacaa aaaagacaaa agtagtagtc acattgcatt   14640
agactttcat tattacctgt ataggcatat atccttgagg gtcaggaagt tctcaaaaga   14700
taagattatc ctacattatt atttttatgat gtgttttttaa aaggtaaatg aaggtgtagg   14760
ttatttagtg cgatgtttat tgcagagctg ctttatttta aaaagaagg aaaaaatcct    14820
gcaagatctg aaacagatca agtctcagcc aggtcagaaa aggtaatgca aaagtaactc   14880
aaaagtagcg tgcacacatta cttattataa aaagtaactt agtaatgtaa cttacttttt   14940
tgaggagtaa ctaaaaattg taatgcatta ctttgaaaaa taactttccc caataacaat   15000
ttacagttga agtcagtatt ctagccctcc tttgaacttt gttttctttt taaaatattt   15060
tacaaattat gtttaacaga tgtctggtaa tatttttttt tgttctggag aaagtcttac   15120
ctgttatatt taggctatta attcaggagg gcaaataatt cttacttcaa ctgtagttca   15180
aaagttttag gaaatgggtt tcagaaaatc atgcttttt tcagtaaata ttcagctttg    15240
aatcactggc ataaatagca ttttaaacct attcttaatt aaaatgattt tcatttatat   15300
tatttctaaa ccaaaaaaaa atgtataaaa tatgacaaaa attgcgaaaa atgacttaca   15360
gatttttattg tatttattta caaaaaaata cccatttagc tttgtttatt ttatttctat   15420
ttcagttttta gctttaattt ctgtttactt tcaatgtgtt ttgttaagtt gaaaaattat   15480
tagtttttttt tttttacatt tttaaaatat gtttttctat atttccatttt tacttgtaat   15540
ttttataata cattgtgtat tgtgctgtca ttgtttctta aactatttat tcattcattc   15600
atttttcttt tggtttagtc cctttattaa tctggggttg ccagagcgga atgaatcgcc   15660
aatttatcca gcacatgttt taagcagcgg atggccttcc agctgtaacc catctctggg   15720
aaacatgcat acagtcattc acactcatac actaggccta tttagcctgc ccaattcaca   15780
tgtaccgcat gtctttggac tgtgggggaa accctaacgc agggagaaca tgcaaactcc   15840
acacagaaac gccaactgac tcagccgagg ctcaaaccag caaccttctt gctgtcaggt   15900
gacagtgcta cctactgcgc cactgtgtcg ccttaaacta tttttttattg ttttattgtt    15960
```

```
attttttggat ttgaaaattt gtgaaaatta aatcacatta aacaactaaa ctgaacttca    16020
tctcagaaaa ctgggctgtc attttcaatt tactagaact tctatgttaa gcaactttaa    16080
tagaatctac attgtaaaag cgctataaaa ataaagattg tagttttaat aatttatcgt    16140
gtactgtact gtgctgtcat tgtttttgta tactatgtta gtttgaattt ttttatttca    16200
aatttggttt taattcagtt ttagttttac acctccattt gggaaattaa ttccaagttt    16260
taattatttc acctataagg atacatttc agactcatta agttttgata aaatatttta    16320
tttcattttg cattttattt cttgttcaca ttttaatta ttgttgtcct ttttattt     16380 aatcgaaagt tgtagtaagt acaaattccc catgtccact tcattcattc atttatttat    16440
tttccttggg cttagtccct ttattcatca ggggtcgcca cagtggaatg aaccgctaac    16500
ttatcaagca tatgtttcac gcatgaactt ccagctgcaa cccagttctg ggaaacaccc    16560
atacactctc acatacacta aagccaattt agcttattca attcactttt agcgcatgtc    16620 cttgactgt gagggaaaac agagcacttg gaggaaaccc gtgcgaacac agggagaact    16680
tgcaaactcc acacagaaat gccaactgac ccagccagga ctcaaattag tgacctactt    16740
gcggtgaggc gatggtgtaa tcaactccac tcaaatgaaa tatattgtga agtaaagtct    16800
acgcatcaat ccacagaaga ttttcatct cactctgtgg ccataacagc ttaaaagaa    16860 ctttatcgga tttgatgtcc gaattaagct catttaaac cacccagaca tatttatgga    16920
cattagtgtg tgagtaactg ttacgctagt acaaatgttg tggaggcttc agccaaggac    16980
attaagtaat aacactagaa cattctctat ggctgagtaa tggcctggag ccaatccagc    17040
atttcgctcg gtccacaggg cttcaaccat ccaatggcct tcatgttttt gtcaatggac    17100
ccatgatggg gtgctgggat cacctttgct ttggtttcca tctctgtgtg agccatttgt    17160
taggtgtcat ttaaatgtta aatgggagag gcagagcatt cagcagctcc ttcacaagcc    17220
cagagcagca cattaacact tttaaaagct cctcctccac actgacccag gtcatgttca    17280
ggcaagacag ctttcgggag attccaacag ttttgatgtt tgtgctccta ggtgttgtgt    17340
ttttctttta gacttaaagc tcacacaaaa gagcaagggc ttatgttgca aaatcttaca    17400
tttcacttaa aaattgtctt gttgttgcgg aacggcaaac ctttattgga ataatagagg    17460
agaaaataca tagtgtgtgt gtttaataaa gtgctttcaa ttaattaaag aaaaaaacta    17520
atttagagat ttgtataatt aggtttaaat attaaaatcc aaaaatttt aaattatatg    17580 taaataatta caaataagca aaaaaatgct caaaatagag tgtatgggtt aataggttgt    17640
ttaaatgaat aatatacatg cacgtatata cattttattt agtgtacttg tatactataa    17700
caacaaaata ttcactacc tgacaaaagt cttgtcttct atcccagttg taagaacaac    17760
aaataattac ttgtcttgta gttgatcatt tggaaaagtg gtagaaggta gatgcagaaa    17820 gtagatttt cagatgaatc atctgttgaa ctgcatcacg atcatcacaa atactgcaga    17880
agacctattg gaacccgcat ggacccaaga ttcttacaga aatcagtcaa gtttggtgag    17940
agaaaaatca tggtttggag ttaaattcag tttggaggtg tggaaaagat ctgcagagtg    18000
gatggcaaca ttaacagcct gaggtatcta ccctgaggta gcctgaggta ttacaaacca    18060
caagagaggg taaattcttc agcaggatag aactcctcat acttcagctt ccacatcaaa    18120
gttcctgaaa gcaaagaagg ttaaggtgct ccaggattgg ccagcacagt caccagacat    18180
gaacatattg agcatggggt aagatgaaag aaaaggcact gaagatgaat ccgaagaatc    18240
ttgatgaact ccgggagtcc tgcatgaacg ctttcttggc cattccaaat gactttatta    18300
ataagtgatt tgagtcactg cagagatgga tgcagtcctc caagctcatg ggagtcatat    18360
```

```
acaatattca ttcttttacc accgcaccat gacattatat tctatcctga acattatttc    18420
tgttcagacc ttactgtctt aattaaatca ttaaaaatca aagcatgatc atattttatt    18480
ttggtcaaat aagcagaaat tttaacacct tgactttca tataaatcac ttctgtaacc    18540
aaatgatcaa ctagtagtaa agttattatt tgttgttcct aaaacttgga taggcgacaa    18600
tacatttgtc aggtagtgta aatatatata tatatatata tatatatata tatatatata    18660
tatatatata tatatatata tatatatata tatatatata tatatatata tatatatata    18720
tatatatata tatatatata tatatatata tatnnatgta tntannnnnn nnnnnnnnnn    18780
nnnnnnnnnn nnnnnnnnnn nnnnnnnnnn nnnnnnnnnn nnnnnnnnnn nnnnnnnnnn    18840
gtctaatctc cttggtgtta atatctatcc atccacccat ccatccatct catccatccg    18900
tcacttgctc aaaatggata actcattcct caaaagcaag tattgatgtc agtcaaagtg    18960
tcagtgtaag atgaaaagtc ctgacagcat tgtttatgaa caagatagtc aaatggcttt    19020
gtcatgtttt catggtttca cagtttacac taagttttt tccaatgcaa taaagtcaga    19080
ttttggtaac acttgctgaa aatgctcaag acaggactat atactattgg cacagccatt    19140
tgaaaactac agtaaagtta agacatccct gcatttaatg agggatttga gtacaagaca    19200
ctgaatatgt aagtttcaca ttttactgca tttgcatttt gcaatactaa tttagtcaca    19260
gcattgtgca gaagaataaa cacacccta tttacaacaa ataaatttt cctttgggta    19320 gagctgtgca caactggaaa caatattgca gtacatatta caactgaacc tacaacatac    19380
atggtgtagg tctgtaaatc attcatcaaa ttgttcaatt tagaagacat tttcaggatt    19440 tttttttt tttttactt tttaaaaaaa gatttaattt acatttgaca gatttgaca    19500 tctagttcaa aattttgca tgtaatgact ccagtaatga aatgaggact attagtttta    19560
tataaaatga ctattcagca tcaattaatt ttgactgaca tgacattagc aaattaaaat    19620
aatataaaac agcagagagt tgtatgaaag caattaatgc atgtcaaaaa gcatctgcag    19680
tttattggaa ggaataagaa actgctatta tgatgtgcac aaatgaacta attgctttga    19740
gaaatgcatg aactaactgt tgtgcaaatg taaatagtgt tgggagaaat gcactaaagc    19800
gactgagaaa aactgtaatc taaataatt taaggtaatg caaaaactat tttaaaatac    19860
ttcatattat attataatgc tctaaattaa attaactaaa acaaagcatc taagaaaata    19920
tactttgtat ttgaaaaaaa agtcaaaatg aataaatgta tatatgtata tatatatata    19980
tatatatata tatgtgtgtg tgtgtgtgtg nnnnnnnnnn nnnnnnnnnn nnnnnnnnnn    20040
nnnnnnnnnn nnnnnnnnnn nnnnnnnnnn nnnnnnnnnn nnnnnnnnnn nnnnnnnnnn    20100
gacggacgga cggacggacg gacggacgga cggacggacg gacggacgga gacacagaca    20160
gatagataga cagatagata gacagacaga cagacagata gacagacaga tagatagata    20220
gatagacaga cagacagaca gacagacaga cagatagata gacagacga gacagacaga    20280 cagacagaca gacagataga tagatagata gatagataga tagacagaga cggacagaca    20340
gacagacaga cagacagaca gacagacaga cagatagcat agatagatag atagatagat    20400
agatagatag atagatagat agatagatag atggatagat ggatagatgg atatatggat    20460
atatggatag acagatggtc agacggaggg acggaaaaac taatagacag acagaaatgt    20520
agatagataa atagatagac agacagacag accaaggata ttagagatag atcaaagaga    20580
ttaaagatag acagataata taatataata taatataata taatataata taatataata    20640
tgaacaagat agttgtcaac aagctactaa ctatgatttg aacatgatgt gtatcaaatc    20700
```

```
aaatgtcctg agctcaatgt cagcaggctg tgtgtggttt gatgctccag tgatcaaggc   20760
ccatttcagt ggcgttttca gctctggctg cagatagcaa ggtcagcaga tgtattataa   20820
agcaggtgcg cccacacaca cttgcacaca aacacacacg cacacacaga actccaaaca   20880
ctgccacatt gattttttt ccagagggta ataacatcat cccggtattg tgaggagtaa    20940
tttaaactta atatgggtaa atactctcca atagctgata gttcatttaa agcttgacat   21000
aatgctgttt gtgtgcagga gaatgaagga taaagaatgg cagggaaatg gattaagcgc   21060
tgatgggcca cacagttagt caggcagctg tcttcattac agactatggg actaaaccct   21120
aagcaccccc taaggacgga gcttcagagg aaatctatag ctaaatgcat catcagagag   21180
acaaacaaac gcttattgcc aacactactg ctacatgtgc ctgcgacctg ctccgaaaag   21240
gagattctgc ttgttgttta aacagatgaa gtaaaggaaa cgcacctgga tccctcctcc   21300
ctaaagagcc attcaaaacg gcagatgtgt ttggtgtaaa tagaaggatt ttttttagg    21360 atgtgtgggt gcttccaaca acatcaacaa aaaagtgga atcatacata caagatgcta    21420
tgcaaatcat actaatagaa gttaaaaatg taaacatttt gataaaaaac aattttttcaa   21480 atgtgtttta aaaaaaaaaa agttatggcc aaatttagaa ttcattcacc ccagagtgga   21540
tgaaaatatg cccaacagca cataaggggtt aacgtaagtt gcaaacaatg tatataggct   21600
gaatgtaaat taaatgtaga cattaaattg gaaattaaat gttgtaatgt tcaactaaat   21660
ttctttgttt aaattcagcc ccagctgatc tcacgggaaa acagaagtat tttacgtttt   21720
gccagttaat tcagtcgtac gaaattgtac gatttttaaaa aggaggctcg gcacctaacc   21780 ccaccctaa acgcaaccgt cactggggga tgaggaaatc gtactaaatt gtacaaatta    21840
gatcgtacga attcttacga attatccact aaatcaaaaa gttacaaatt gccgtgagat   21900
tgtgttgatc agcccataga aattgtttgc aaccacttac cttaaaaatt tagtaaatcc   21960
aatgattcat tttttagtgc atgtaacata cttggttttc aagattgttc tctgttaatt   22020
tgcaagaaat gctctttaca caaatagaac ttccccatac ccctcaggta agatggacct   22080
ttttaggttc tcagtcacaa aaaacctccc agaaagattt tatgaaggtt ccttttttgtt   22140 caccagaaaa gtatacccaa agaacgctct caaaatgttc caatttggtt ccctaaaaat   22200
aagaaaacag gtaccaaatg gtaccttctg ggaaatgttc tgttgcctgg gttcaaagga   22260
aatcccacag ccactctttt ttctcacagc gtatcatcgt tctctaccac taatcaaaca   22320
aggtcacaca tctccagttt ggagggcagc tcggctctgt cttccgcagg gaatcgtgtg   22380
ccctgttctc cagagaaaga ggacacggag acaatgtcac agcagaaaac agccacaatc   22440
atcgctcctc cagggcttta cagtaacggc caaagtcaca caaggtgagt cgtcaaaggc   22500
agacgcacga ggtgaagccc tcaaccatct ggacaacaag atgcagctcc acacattgcc   22560
atgttctaca tatgtttatt taaatcacag gaagtggctt tcacttttgt aaacttcgaa   22620
gtctgaatat gcatgcacag aggccactgc ttcatattac tgtaacggat ttctgcatca   22680
tgtttacaga caactcaagt tcataggaaa ttacagcaaa gaaacagtct gattgacgtc   22740 tgaactttt tgagcttcgt ttgtttagtc tacaaatgcg cattatatga cttgtgagag   22800
tggttctgat ttcgctatat gaaacaagat atactgtatg cataatgaac taaactccaa   22860
aaataacttc aaaccaagtt caaactactt atttgaaatt attagagttg aaaacacaat   22920
tcttacattg tttcttaaaa caactttgtt caaccaaaga ctatataata tacagtcaag   22980
acgtgtcact cgtaaagttt tgaacgggta aaattgtgac ggtcaatatg acgaatgaag   23040
cactgccttt tagtacaaga gccaatcatt caattcaatt tatctttatt tctatagcgc   23100
```

```
ttttacagtg aagattggta aaaagcagca taatatagaa gttctagcaa actgaaaatg  23160
ttagtccagt tttcagtttg gttcggttca gtttggttta attttcactt tcaaaagtcc  23220
aaaatactga agggcaaatc catcgatgtg cagctccact acttacaaac caagcaagcc  23280
agtggcgaga acaaacttc accaattgac aaaagtgtag agagaaaaaa aaactcaaga  23340
gaaaccaggc tcagttgggc aagtacagtt ttctggccaa acttcatgtg cattactgca  23400
gtctaggcac cagagggtgg agaatgcagg atgtggagaa agaagagacg tggagaagct  23460
gcaggtgcga cggctgtttta ggctggccac aagattgatg cacagactcg tctgtcactg  23520 gagttttca ggactcagtc ctatgctctc cacttcttta tgactgctcc agaatctgct  23580
caggatatgg cctggtcaag gattatggag acctctagaa gtcctctatg gttggaatca  23640
tctcctctga ggtctcaaaa gatctcaaga aaagttatca ttgatcgcta tagatcgatg  23700
attctccagg aaaggggctt ggtttcaaca gatcttgtgt gattcgaaca tttataaata  23760
aactaaatgc agcgatgccc aaactttttc ttatgaaggg ccataaacct tgattgggca  23820
gaaggcaaat atagtttcca tgtgtaattt ccttatttat ttaaaatgat ttaaaaatgt  23880
ctagactaca ttgctttata tgaacttata cagtattttt aacattttac aacgaactta  23940
ttacactaaa tatctaattt ttgccttgat ttgctcgtcg atgtcttctg catagtccgt  24000
cgagatcgta cgaaaggtcc gtcatttaaa tttttttaaa tctgattcat ttacaacatt  24060
taatttaagg atttaatttc agtttgcttt ttttgtagct cagcaacaaa acaaacaaat  24120
taaaactgca agcagcaata aaagggacct tgcactatca aaaaaggtta cgtcaaatta  24180 gaataatga tctcggtgtt aaaagcattt gccccaaccc tctccatcat tctcactctc  24240
atctcagttg gggtggtgaa ccaaatcaaa ggttacaacg ggccaacttt ggcctgcagg  24300
cccaactttg agcatctctg atctaaaaaa acagtcgttg tttaatatta ttggagattc  24360
ctaatatgaa atgtaagctt ggcatgcaat tttagagaat ttgttgtttc cccatttaaa  24420
caaaatgccc gagaggcgtt tcaaagacgg ccgctgagtg aaatgactag ccttaaaggg  24480
actctgcttc aatccacttc agtttgtaaa aaaaatttta tcgattcttt ttgagacaac  24540
atgaagaaat tgtgcacaac ccagcatttt tacagtgtag gtcaaaataa gacaaacctt  24600
cagcatcttt catcgctgcg atgcagttag ctagtctgac actggaggta aaaatgcaag  24660 atatttttc tttcgtatta catacagatg tttcaccgga taaaatctgc ataacgttgc  24720
caagagcaat tattagttt atgcagtcct tctgagctga attaattaat tacaagtaac  24780
aagtcaggtg tgaactgtcc aatcacatca aaacaaactg ctttcacgct tgaaagagaa  24840
tgagattttc ttaaatactt taatgaggtg ttaacaaaat aagtggtaca gtttattatt  24900
ccagtcagtt gatagtgttt ttcagtgtgc atattaatac acaaaacata cagagagaag  24960 aaaaaacag gtccaattca gcccccccgat gcttctttaa agcatattag cacatcatttt  25020 tcttttttct gggaatgcat cgagggcctt aagcgattca atcatttcta acgccgggtt  25080
gctaacgaga tcctcgcagc tccaaaccgg tgtgaacatc tgtgaaatag taagcgagtt  25140
gaagcgtgca tggagtggaa tgagagaggg tgatgctgca tacgagtagc ctgtttaatg  25200
tcatcatttg gtcattatgg tcaaaggtcc tttcagttta gtccacaaac aaaaaacacg  25260
tccagacatg atgtttaaaa aaaacgcatc accccaaaaa ccgggcgccg tgtggagtaa  25320
acacaaacct catcatgcat ctgatcaggc ttgaaatccc caaagggct gaaagaagcc  25380 actttacggt gactgtatcg aaaaacaatg ctcaccgatg ctcagtttgt tcaatgcaaa  25440
```

```
aatacatcaa cggaatatca taaccagaaa ggcaatatat aacatttaac acaagaaaaa   25500
gagcaagaaa tcaaacaaga aagcgagaaa tagtttatac atgctgcagt tagagtagta   25560
acatgcgttt acctcgtctg tttggagatc gccaagagga acactcattt tagtgtctta   25620
ttttggtcct gcattgaaga aagctgttgt gttttcacct ctctatacag aaaatgtctc   25680
ctccattcac agttgtaagt atctacaaca gtgttcaata atgttccctg ctccaatcaa   25740
tcttcaatct aaaacgagga aacaagtcca accgtcttaa aacaacttct ggaaaactct   25800
gattcaacac attgtgcaca ttctatatag atgacagtac tcttaaataa aaatatagta   25860
ataaaacaaa gtgttctcat ccttacgcta cagaaaacag ataatcagaa actttcttca   25920
agaatatccc atgtggtata gagttttaaa atggcttact atatatgctc aaaggattct   25980
ctttcatatt tacaaaataa aatgcatatc tttagcattg ggaggtcctg cgtaccatca   26040
cagtcattct ttttttcctt agtttgcaga gtccggaaag ctaaaactgt tggtcgaagg   26100
cactgacaaa tgtcctttca tcagtgctgc tgattaacat gatacaaaaa taattgagaa   26160
aaaaatagac acttaaggac tagtggttac aaatggcaga aagtgaaaga catttggcaa   26220
agttactgtt tcatctggtc ccaacaaagc aaagtcaggt tcttgttgct tcctttcgtg   26280
tgattgattg cgaccatgca aataaaggca gcgatgatat gcgagtaaca gagggataaa   26340
gcgaccgttc acacacactc ctccgcagac atcagcagag ggttgatgta ctcgaagcct   26400
tcaaactcag actggtcgat cttctttaca gcatcactgg gggaaaggca aacacataat   26460
caatcagtct taacccttta ataggcatcg taactgtctg cttgaccttt ggtccactga   26520
ctttcattca aataaaaacc tcaaaatcag cttagagtgg tggtaggaac aaaatttcaa   26580
taaaaaattc ttagtgtgaa atttaaagag gccaaacaat gttgatatct gaaagcaatt   26640
ttttgatttc tccactaaag ttcctataga cacatctctt ggtgctgatt ggctgcaagt   26700
ctgtttggg acttggtcat tttgcatgta aagtcgaaat actctcactg acgcctctgc   26760
atgagttaat tttttatgtg accattactt agaatgcatc acttcaactt ttccatggca   26820
atgccacaac accagattta tgtatatccc atttttatgta tattctgcaa atattgacaa   26880
acatcctaat tttattgaga aatatctgat atgccaatac taaaatatgt gtaaggaaat   26940
ggactaattt aaatgtctaa gacataaaat gaatgtaagt tgtctgaaaa caccaacaat   27000
attagattta tgacattatt atccagcagc tgatcatgtg acgcactgac tattaatcac   27060
accagtgtga tcgtgcgcat caaagagtta accactattc tcaaaagag acaggctata   27120
aaatatcttc cagaatgttt atgtgtaagc acacagactt tattattcaa aaaccttaat   27180
aaagatcata ttgatggggg atcagagctg ctggatttaa aacatggtaa ttcatcatct   27240
tcacccaaat tacatgaaag taacttactg tttagctgag aaatgaacag agtgaaggtt   27300
attgcacgat gaatccaaaa ttttcgcctg taattttgc acattaaaaa ataaattcaa   27360
cctcacgttg tgtctatcct gttgacagac tgcctctgaa actttcgtcc gttataaaaa   27420
aaaaaattta atcgggtttg atttttaat ttttcacgtc caaaagacg ttttgagagg   27480
cgttttgaca gttcagagcc accatacaag caaaaggcaa aacacaaaat ccccttactt   27540
gagccacaga taactttatg acaaacacag tgcatgatat aagacaaaac atgtcaaaga   27600
gttgaaaacc catatgtctg aatcagtgac tagttcactt ctaacctgct gctgtttggg   27660
ctgtgtgtgt ctctgtgtat gtgtccatac atttgacgta ctgtccatag acattataat   27720
agaaagacac ctcatgtttt ttttcggtcc gttgctccaa tgtcaatgtg gccgccattt   27780
attctaatgt ctatggtact gcaagtctct gttcagtcta tgtgaagcat cacaagcaat   27840
```

```
gtatcaaaat tccactgatt ttctaaaata agtgttgcat ttacattcct ctttcttttt    27900
ctacttcaga aaagagagga gaataaagta tcgctgcttg aattgactcc gaaatgtttt    27960
gcattttttt actgaatgga ttaattaaca cgcatcggac tcagtatgca agcattgtat    28020
ttgttcgtct tacacacgag acgttaaacc gaggtcctga ctctttgtgg ttaaaaatct    28080
catgacattt cttgtaaaga gcaggggtgt aacccggtg tcctggtcaa attttcttca     28140
tcggccctta cccatcatgt actcccaatc atccccatcc aatgaattgg ctttatcact    28200
atctctccac tccaccaata gcttgtgtac aataaataaa tgcatacgta aattttggac    28260
ttcagtgtgc aaagacctta aacgttttag taacattaac agtgtgacac acatcgtcag    28320
ataatgtgta acatgattat catagactat cataaacatt agcgtgacgt tttacaaacc    28380
aataaatgtt atgttttgct agcacttggg taaattaagg ctgaacatta tatcgtttaa    28440
gcatcgatat cgcaatgtgt gtatctgcaa tagtcacata gcaggattag attattttta    28500
agattaaact ataaggatat tattacattt tattgttatt aaaactgttt atacaataat    28560
aagcatgttg ttttacattt gactgttcga tttctgtaca tgaatactct tagacttaac    28620
aaaaaatcat aaagtatcgt ttatccattt gcttttgctt gtaattttta ataatttatg    28680
cagatccact gcattaaatc atcccagtca atctacattt ccaaatagag ctaataaatt    28740
catctggtaa aattatattc atatcacaat atatattgca gtaaaataaa atatcacaat    28800
gtcagatttt tccagtatca tgcagcccta atttaaatga ctgaaaccta aaattaatgt    28860
catttttctg aaaacaccaa caatgttaca tttatgatat tattattcag cagctgatta    28920
tgtgacacat tgatcatttt aatcacacca gtgtgatcgt gcgcatcaaa gagttagcca    28980
ctattttcaa acagagacag gctgtaaaat atcttccagg aaaactgggt tatgtggaaa    29040
tgagtgaatc gagtctgtaa tgtgtcatca tacatcgtaa aaagcaatat tacttcctga    29100
tgaaagctgc attgctgtgg tgaagatgtg aagtagatca atggcgtctg agcctgtgat    29160
tcagaaagca agaggcgtga cagtgacaga tgtacatgaa cagacactca ctcatcgtca    29220
ggcgtgagct gaatgggctc gttggtgaac tgggcatcaa agttatccag accaaactcg    29280
cccgagatgt taggtttgaa cggtggaact acttgcttct gctccatctg aaatacaggt    29340
aacatgagtc aaataatgac tgaaatatac tcatcataat gaggttacta cttcttaaag    29400
ttaattaacc attaactata aagaacagat gtttcagtta aggaagcaag aattctacat    29460
gtacatgagc caaaaatgac gtatatttta accatgattt actaaagaca atcatgataa    29520
gatcattcag tgtagcaata gtttatacac ctaaaaaatc ctgtcatatt aagaacaaga    29580
gtcactggaa gacatattaa aaggttcagc ccaaaaatac tactttagat acctcatcct    29640
ttgtaattat ccttccagcc actatatttt acccttttgt tagtgggttt ttaattcaat    29700
acaaatgtac tacatttaaa tattctttta tatatgtaac aaatatatgt tcacttattc    29760
ctttatgtaa tacatgagaa agaacaacat taagcatttt cattttgtct gtttatgcta    29820
aaataacaca caaatttgtc aattgtgctt gacataaatc ttttttgaaga ataaaaatga    29880 gtgataataa ttctctgata ttttttatttt tgttactttg agcaaaaact taatactgag    29940 tttttttaggg ctgctcttcc cagctcttac tctgtccttg ctgtaaggtc aggattagct    30000
ccccctgcag gccaccacaa acaccgcagt ctgtctgaga gcaaagtgta atctgatcgt    30060
tcaaactgtc tgaccgctac agctgtctgt gtgtgtgttg cccagacaaa acagggacaa    30120
gaggtcactg tttgtctgag tctcatctgc tggtttgaca tcatttaaac ctgcctcaca    30180
```

```
tgatacagtt cacagtctca accctaagag cagaaaaatc aataacatga caccttatca    30240
ccttcattgt atcactgccc ttacacgtga tcatgataca accacaataa aataaaacac    30300 tcagactta atacattcta cagattcaga tatagtatac caatatgtat tagtacggaa     30360
actcgacaga aatcaaaaaa ataaattata aaccgcttga ggatttgctg aatttaatat    30420
ccattggtta aagtaaaaca ctaatattgg tttaattcta aaaggtctg aaaaaaagtc     30480 tcaatttcaa cttattttgt ctctataata aacactttca tttgttgtga ttgaaatgca    30540
gggttgttat cccatacatt attgatctct tgacttttt acagttaaaa cattgtcatt     30600
gtgttgtaaa ataactaaat ctaaaaacat gcaattttg ttatttaatg ctaaaaaagt     30660 atttaaatt tgataaaaat ctgtgcaaat taaacaaaaa atgtaatctg gaggatttta    30720
aacgctaatg ctgtctaaac taatgctcaa gacacaaaaa acctcaaaaa agtactccag    30780
ggtgtcttaa aacctttaat tttgacgcca caaataagtt cttgactttt aaatctaaca    30840
tatgtaatct taaatacac ccctcacttt tctgtttgtg taaaaaaaaa atatacacaa     30900
aactaatagg atgtgtttat aatgactcat ttttgggcga gctttacttt caaagctgac    30960
gctgctgaaa tgctacttga agtggtaaga gctcacgacc aaattacagg aatgactaat    31020
caaatgaagg attcctcaag gtcataaaca acagtaaaca gctcttcagg ctccagtaag    31080
tcctctgttt agtttcacta acgtcaggct agagagaatg actcattgct tcctctgcgt    31140
ctcaagtcaa aacatccaag aagacagata aaggaaacgg agataacaat gactcacaag    31200
atcccagtct acatttcgga aaaaaggatg ggccatgatg tctgcgaagc ctgtctgagg    31260
atgacatccc agccgttcct tcgactccta caaaaaaaag gactaaatgt cagtgagaag    31320
aaataagata tattttagtt ctttttttgct ctaattgtcc agctaattgt ttgctaaaag    31380
tctaatttga tattcatctt gggcctcatg tatcaacgct gcgtacgcac aaaaactttg    31440
cgtacgccag gattcacgct cagaatcgct cacgtttgga tttactaaca atgaactgaa    31500
cgtgggaatg tgcgcaggtt cacggcagct ttctggctgg cgtacgcaca ttttttgtgc    31560
gtgtctgttt tatttccatt ggcgactcct agaggcagtt gtgttaaatt cctctctaca    31620
aagtgtctga gccttgcaat ggcagctgta tgagacgggt tcatctagta ggtatacaag    31680
gtttccatac catacagttg accagctaaa cattaaagca caatttgcag cggtcgcctg    31740
ttttcccaat gtaatctgag cgatctaccg cacgcacatt gctataaaga cactatctga    31800
agatgaattt gcatgagtga atcagaaaca tttccattca attaatgtgc aaataaaata    31860
tgatgcacaa acttattgat gattcctact tgtctttctc gtgataaata gtgggcaaaa    31920
tctgatatgt agcgggggaaa aaagaagaaa gagttcatca gacgctggat tcgagccgag    31980
tttatgctcg aacatgtcag tacatgatca catgcgtctt acgaggtgcg ccactgagac    32040
tgttaagggt actacaacat tttacagata taaaccacac tatttatttt ttaaatgcac    32100
tcagtgcgat gttcagaccc aactgtgtta accgcatcag ctaaactctc ccactctatt    32160 tttttttcttt tgttgttaat tccggagaac aaacttgcaa ataacaccgc ttttctccgg    32220
tctacctccg aaagcagcac ctccatttca cattctgttc aaagtttctc tttttgcttg    32280
cttttgccat tgctttttg ttgggttttt gcattagcat agtcattagc atattcatac     32340
gggggaagag gcaggaggg gttttgtgct cgtgcatgtt gcgctcagtt tcacgttcat     32400
tcggatgtac aaaagaatat gcgtgagatt cggcgtacgc agtgtttcat acatctgaat    32460
ttttctgcgt acgcacattt acagcttgt gcatacgcaa tgttttagta agatttccac     32520
gcaagtcttc gtacatgagg cccctggtct ttgtatgaat aaaacagaaa cagtattatg    32580
```

```
tacaatatta gactaaaaag gaggatcttc atattgctgc ttttctggta atttaacttg   32640
cttctattga cctcatttgt gagttgcttt gaaaaaaaca tctgctaaat caataagtgt   32700
aaatgcaaag agatgaacag acacacagaa tgattaacac acaacagaag gaaataaagt   32760
aaagaatgat tatggcagca ctataacaag ctcatctgac gtaaggacat tagcattgat   32820
ctgtctggtc tgcttcacct tgttgaggaa tcccttcagc acgcttgcgg ctttgaccga   32880
taacgatctg ggaattctga tctgcttctc caaaatgact gcagaagaag tgtaaaggaa   32940
aacatgagac acgcacagaa agacaaagca ttttgaaac gttcatgctg ccagtcatgt    33000
accttggaaa agataatcct ctgtgttttg gtcagggtta tcagagctgc cgactatgtc   33060
gaagggagat cttccagcca tcatctcaaa catcaggacg cccagagccc accagtccac   33120
actaaaacct ggacacaaat aacatgcatc attctaaggc ttcatactgg tataaatgta   33180
atcgtcagtg ggggttatga agcaatcgct aactataata aaggtttcaa aggtgcagta   33240
tgtaggattg attgaactag gtattgcagt ccaaattcaa atattgaag tttgtttttt    33300 ctcacttagc ccttccgctg acacaaaggt tgccagattg attacaacaa caggagaaag   33360
agtgccttca gtttagcctt tcactgtaaa cggatcagct aatgtttatg tttgtagttt   33420
tttgctaaat aaaaactagc tcatgtagat atacaggtca tattttggca gctcagagag   33480
ccaaaatata atgagtaaac ttgcagtggg gggagttaca gagaccaaaa cattgacaca   33540
aaactcccat tttcaaaagg agaataactg actctagcat cattttttcag ataaacaagt   33600 atgttcatta agtattcatc ttaaatgtct gcatatataa catatggtat ttttaagact   33660
cagaagagcc ataaacttac atgcagcacc ttcatgcata agcaaatttg tgattacagc   33720
gttagcaaac atagttgcta actgaaaatc ttcataaaga gtctctgctg tgtgtgaatt   33780
gagtttacca tagtcttctc ctctcagaat ctctggtgca atgtaattgg gagttccaca   33840
gaaagtgctg gttgtatctc ctggtctcag tccctcctgt gtaacagata acaataatga   33900
aaccaaaaaa acttataaca cacattagct atgtttccat gcacctattt ttatgcacat   33960
tttggataca agcaaaaaaa aattttgatt aatggaaatg tcaagaagcg catcaatttt   34020
aaaacgagta ggacaaactt tttattttat aataaaacta aactaggatg gaaacacttt   34080
taccgaacaa attccaggtt gcgcattaaa actggtcatg tgattttgtt atgagatcat   34140
gtaatgaaaa aaatatgtgc gaatggaaaa accagcaggc tgagctcact ataaaacatc   34200
tgaaatgttg tttagtcat tctaaaacgc cttaaccgtt tcagcattag tgtcattata    34260
tcattaatct tcgcgtttca cgcctttaaa cgccaccaca tgttcactgc gagtcagttt   34320
ttatgatcat ttgtgttttt gttttgggt agattaaaag ctttcattat ttttaatata    34380
gatgcttttt aatacatcaa tgcactatat tatctaaatg atactttatt tcattttaaa   34440
ttattaattt aatttaattt ataaatgtac aggtttatac ttcctaaaat catatcattt   34500
ttttcattaa acaaaaaggt tgcagtaata agaagtttat taccagcagt gcaccagtat   34560
tttattcaaa agcaggtgag gtttgtgaca ttaaatgtta ttagatgtca gacagtacat   34620 cttttttctaa aactttgagt tgtttccac tgctgaaaaa agaaaagcag tgcccagtat    34680
aaacgaatgc actctttaaa gatttctctt aaaaatgaat accatctcag acccccctagt  34740 ttttcaaga tttcacgatc gctaaatcca acacaaaatc aagaaaaatt cgtaaatttt    34800
agtgatcctg caaaactctt aattaaacgc aaaatgattg caaataaat aaataaataa    34860 ataaatatat atatatatat atatatatat atatatatat atatatatat atatatatat   34920
```

```
atacatatac atatatatat atatatatat atacatatat acatatctac atatatatat   34980
atacacatat atatatatat atacatctta aaacatcaaa ttccanacca tataatcaca   35040
ttatatttat tttcagttta ttattaattg tattacgtga ctaatagatg ttgttgcatg   35100
cgcagcgcac atcatgtatt tgaggttctc ttgaaaaatg acgtttcacc tgcgtcctta   35160
caatcattac attatatgag agtaggcaga attgttttgc agcctgtgca gtaagcagac   35220
acggatgaag cgccagtgat ttacatttga agtcaatgca aagactagat taggcatcct   35280
gtggcacgaa ttagtctgtg catttaatgc acttcagact gaaaaaaaaa aaaaaagag   35340
caaacatcta acaaacagag caatggaaca gacagaagaa caagcagctt acaaagatgg   35400
aggttgattc aaggatgacg gccgctggac gtgactgaat tgaaggacat tatttgtgct   35460
ttacatctat ggctggtaat acgatgtgaa taaaatcgat aaatgttttt gtttgactct   35520
tttcctgcag gtaccgagag aaaacgcttc cttgccattg atgagtttta cgttaatctg   35580
tttttaaggt gtattacagt aggggaaacc ctaatgtatg tcctgagtga ggtacacaat   35640
gtcagatgct ccggagagta aaatctgaga gaaagtaaga tcatggataa aaataagagt   35700
tatacaacct tcctttgact taatccttac tgttttagat cttgtcttga caagagacca   35760
aaataaagaa gctttatttt tatgatttgt gtcattcttg tgtcaatcat tgtcagattg   35820
cacacctaac aaagtaggca acctaatatg gtaaatatat ataaatttat aaaaataact   35880
atttttttat tgacaaattt ttcctaaaat ttctgggaat taccaccaca aaatatatat   35940
attttctaaa aaaagtgaaa actaggggggt ctgctattga aaaggattct atacaataag   36000
atatttgtgt ccatacatta cagtagtcag tactaaagcc aaaacttact taagaaaata   36060
ccttaagatt gatgggcaaa aataagtacc aactaatgaa tatcttaagg aaaatgtaaa   36120
ataaatcttt aatacagaaa aatcaagaga accacaaaaa tatagaaaat tgtattgaaa   36180
tttttcagtt tgtcatttt ttgacaacat taaatttaaa tgcattttt attcctaaaa   36240
atgtcaggtg atcacactct tattttaata aatatttaat aactgtatta aatatttaac   36300
tgttttgttt aaatggacca aaatacatac attttcaata tccacaagga catgtataaa   36360
aattcatttt ctaaaggtgt tgtactcatt caaaggttac catcaaaatt ttggtaccca   36420
acttttttca caattacttt ctgtttggag caagtggaaa atttaaccaa tgaccacatt   36480
cagacttacc ttacacatgc cgtaatcggt gagtttgatg tgtccctctg aatccagcag   36540
aacattgtcc agtttcaggt ccctgtaaat aatgccacgc tcatggaggt agttcaaggc   36600
aagactgatc tctgcagagt aaaacctgcg agcggaaaga acaagacaca cagtaagtga   36660
cctcattttt gtttctgttc ctgtggcgag gcgttcagac aacgttaaaa gtgttatgca   36720
ttggatgtcc tcagacctgg cgtgctcttc cggaagtttc ctctgccgct gcatgtggaa   36780
catgagatcc cctccattca catactcgat tacaaagaac agtctgtgaa agaacagcat   36840
taaataatca ttagccccta ttatcagaca aagacacagt tcacacttaa ctaaaaggct   36900
caacaataaa tggcctaaag ggcacttata ttgaattttg ggtgtncact ttaaaaaaaa   36960
aaaatttttac ttttttattct cactacatct tacacttttt atacatgtat tttaatgatg   37020
tcttatgact aggctcacat ggaatctgcg tacgcagaac tctgcagatt ttccgcagat   37080
ttttagccca tcattaattc tgttcattta cccgagtaaa tgtgtgtaaa tctatattta   37140
tttagttttt taattaaata aagtaatatt attgactaat gtaaaaatgt tcatcttatt   37200
tatgtacaat gcagttcgta aagtattatt ttctgtcttt tagtagatat attagatgag   37260
agacttgctt tgtttaccaa ataaagtgaa tctaattgga tttgcatttt aaacattaaa   37320
```

```
tcaaaggtaa aaagatataa ttttttattt tcacattaag gttttagtta taatactccc    37380
aaaatcattc cgcagaaatc cgtagatttt taccaaaatt ctctgcaaaa atagcagaaa    37440
atgttagcag attcagtgtg gcccttctta tgactaaatg aacattgatg tggcaaaaaa    37500
aaaacactct tcaaggctgc atttatttca gttgtagtaa tagtattttt tcatctttaa    37560
tgcatttgta aatgtcattt tttcctatga tgacaaggca gaatttccaa cagccattaa    37620
atccagtatt aagtgtcaca aggagtttca caaataatcc tattatgctg aaccatatcc    37680
tatggtgcag cacaagtgta tttcttattt tcaacaataa aaaccgttta gttgcttaat    37740
attttagaga aagctgggat gaacttatga ccatgaatgt tgttctaaaa tatgcttgtg    37800
aaaaatatta taaaaagatt ttcagaagta taaatctgta aaattgacta aaaataggaa    37860
taaattaatt tgaataaaaa tatttttttg ctaattagta atattcacaa tattatattc    37920
gtttttacaa tgacaatcaa gaaacaaaaa cacagtttac acgaatttca taatataaaa    37980
ggaaatgaaa tacaatctgt atcatatcat cagtaaatac aaatacacaa attataatta    38040
aatacattac aatactttga aaaatataaa ggcgggtaaa acaatctaac ttaaacataa    38100
tataaactaa ttctaaatta acttactgac tttaactaaa ttattagctc ttttttaatg    38160
gaatgctttt aattaactat agctaattat taatttaatg accatggaat gactacaccc    38220
cagtcgaaaa ttatttttga acatgtctca ttgcttttag ctatatattt tggtacattt    38280
aaacaaaacc attttattaa ataataattt aaaaaaagag tgtgcttacc taacatcttt    38340
aggaataaaa tatgcttgtg aaaaatatga tattaatatt cacaagtata aatatatata    38400
agtgtaaatt aataaattaa tgtcaataaa actattattt tgctgattta gtaatattca    38460
caatattaat gagtttaacg atgacaatct agaaatgaaa atacagttta caaacgtatt    38520
caattaattt agtgtcatat tataagatga aattaaatat tatgcattta aatacatctg    38580
tattacaaaa ctataaaaac ttttgatcta cacaaataca aaaacacata ataataaaat    38640
acgttacaat actttgaaaa atatgaagac gggtaaaaca atctaactaa aacatagtat    38700
aaaataattc agttcaaata tatagcatct catttaaaaa aaaaaaagtg ttaataaatc    38760
aataattatt cagtcatagt taaagatgct gtttgtaagt tgttgactca ttttgaagca    38820
taaaaaaaaa taaaatgttt gcagatattt aagaaaatgc caagtaaaca ttcttgttta    38880
tctgaaaaac aatgctgaag tcagatattc tgcttaaaaa tgtgagttac gtgccggaac    38940
gcctgtcttt gttttgctcc tataacccgc ccaatgccag atgagccaat aacattccag    39000
caccctgggt tgccttggtg gaaaaccgca tatttcattc attcattcag aaaggatctc    39060
aaagcatgcg cccgtgaccg aaatgcgacc tccggtggac agtagaagac tccgaaatga    39120
gacgcagatt cagagttcta tatgaggtgg ttattaatta gcaaataata taaacactac    39180
gaccataaac attaggtgag cagattacat tgtaaccta tggtccaaca acccactacg    39240
tgaagagatt tgcaaagata agcaatttgg ctctttgcac aagacaaaca cgacagaaat    39300
ttaaatacag ccattcagaa acacagaata tgcactcaca caagaaatgg taaggtttat    39360
catctaatta atacatatta aacctcttta acattattaa atgtagaagc tgagtcattg    39420
acatgtgttg gttttgagtc acagttcaaa gttcaatttc aagcggctta ttttattttc    39480
gagatctgag gtgaacaatc tgctgctgct ttcaatagta tggcaataaa tgtcatttaa    39540
aatggtattc aaattcacat tattagtatt taacactaaa taaagcacat gaggtgtacc    39600
tgaggagatc actgtcagct ttcagttgtt cagctatgag aaatagaagt tgtttctaat    39660
```

```
atatcaattc aaggtttggt taggacaaaa acttttaaca ttgtaaatat tccttctatt    39720
gcgtgccgtt tctttcatat acaacacttg ctcctctttg tctttaatct ggcaacatgc    39780
gtttgcattt gttttgatcc aggaatgcat tacctagttc aaccacttgg tgtcaaactt    39840
acaaactgca cctttaatca aggtgttcc ataaaaaagg gctaataatt tagttaaaga    39900
aaacaattga gagcttaact gcataaattg taaaatagaa ttaatatgaa cccatgttta    39960
aaacaatcgt gaataacata acaatatatt tgatttgatg atctaaaaat gtgtgcagag    40020
atggacagac ctgctctccg tctggaagca ggagtgaagt cccacaagga agggatggtt    40080
tgaagcctgc tcaaacacat gcttttcagt ctgaacccag tcaatatcct gaaaaacaag    40140
aaagaagaac aaacatcaca cacacacaca cacacacaca caaacacaaa cacacaaaat    40200
caatctccca ttgaaaagca gagcattctt tcagtcagta ggggaaacat ttggaaggac    40260
attcaggaca gtattgagca gaggctcctc gcaaggctga aaactgataa aggttttaaa    40320 agacggggc accaggtctt cccgagaagc tgctcctgta tgtgaggaga ctcataatgg    40380
acagatacag agtgaaaaac taagaccttt cattgacagc ttggtaaaaa tccctctgac    40440
cgtgagactt gcataaagaa gcactgaggg gccagtagag cacagctgcc attattgacc    40500
atcggcttct gctgtcagtt catcacacaa gccttaagtg cggctaatca tcgttaaatg    40560
gtcacttcat caagaccctg tctgtttgtg tgcacttcaa cacattctgg aaagcttata    40620
tccaacgacg cctctttgct taatttattc agcatagtca tgacttattt tgcttttgtc    40680
aggagaaata ttttatttag taaatttcat gaagtctgtg tagaatgtgg tttatttgaa    40740
ccaattatga ttcacaatta gagctgtaaa tttcatttaa acggtagggg gccaagaaat    40800
aatacaatgt aaagcaatgc acagctaaac aatatgctaa ttgtggcctt taaaattata    40860
cccagtcgtc acaaatataa caatgcatgg gaaatggctt tggcatgtta gttgcagtgc    40920
actacgcatc acactatagt aaacaagcta atgttaacta gataaataat attttaatcg    40980
ctaatacagt ggattcaggg aaaactacat cagtaatcag cattttttgca accaagttat    41040 gaacgagtct gcatcaactc tattgatgaa aatcgcttta ttttaagtga ctaaaatacc    41100
ctacttactg gagtccaaca taaactaggc cccagccaca aacctgactc gtgtgtgtgt    41160
gtgtggtgtg tgtgtgtgtg tgtgtgtttt tgtgtgtgtg aattagtata gacgaactgg    41220
gaaagcatgc agtggtccaa accactgtga gcaaggggag ggggaactca acggtttata    41280
aacgcactct ttgtgtttgt tttcttactt atgcaattat tttaggtata catacatata    41340
tttttcacaa tagagagtaa gatttaaaaa aaaaatgttt tggggacaac cctcagatgg    41400 aagcatctc tccgtgtttg atttttcttat acatacgatt ttcttatata cggttatgct    41460
gtcggactgt tgtataaacg caacatcaca cttttagcag tgtgatgcgg ctgtatattg    41520
tcacttgtgg gacacaaagg cattcgggct gtggactcgt gccaacgcac gcctcccacc    41580
agtgccgata tacagctaca tcgcactgct actcgtgtga tattgcttaa tataatttca    41640
acagatgact aaagattggc aattatttta gaaacaaatg taagtgtatt tgcttaaaat    41700
ataacaaaca aatttccagt aaagataaaa acaaagatc aaaatttcaa aagaaataaa    41760
cactgctttt ctggttctgt tttccttctg tatagtctga ccatgcaaaa ctaaatgtaa    41820
ataaaatact gcacagtcat cactgtataa attaaataca attaatattt gtaaagctgc    41880
aaatgttggt gtttcttgtg catgaatgct ctcttgttgt gtttaagcct ttggttcaat    41940
ccaactttgg attgattttg cagacacaga caaattttca aattctgaga caaaaccctc    42000
cagattgcag ctaaatgagg aaatcgtaga tctctctctt ggctgtgact gcttcttgac    42060
```

```
caaatgcgct tttcccctgc atggtacatc ttggctcggc ctggttctgt tcggttcagt   42120
gcggcttgaa tcttctcgct tttcttttc actgcagttt gatatcgctt taattggtgc    42180
gattacagtc atatcatcat agctgtgccg tctgcactgc attgccatga cattctgaat   42240
cagcccattc agctctgaca ggcactcatt tatgatgctg tgacaatcat actttcaat    42300
tttacattgt atgtcattat tgttcccctt gtgtgtgagc atgtgtgaat gtaaaaaagc   42360
gagaggaagc tttcgtcttg tgcagaagcg aaatcaccac ttgatttttt cgctgcttgt   42420
tgtctttaca ttttcatata gtttggcatg tatgtgtatt ttaggattat ttcggattaa   42480
agcccaatac tattctattt gtgtaccct acctttggc ccttgaaacg gagtgcaata    42540
tgtcattgcg agctcatatg agatcgatga tcgcactgct gtagttattc cagttgcact   42600
atattttggt atttatcttc aggaaatcgc caaaggcaat aatatcatgt tgtcataaca   42660
atataatgtg gcaataagct cgtaactgta ctgtgcattt acactgtggc catattcatc   42720
tatgcaaaag aaatcaacat taacgttcta ccagacactg taaaaggtc attcccagcc    42780
gttagacttt tctgacaggg tattccgagt gtcatcaagc attagatgtg gaaagtatgc   42840
tgtgggacag ctatacagga gctattatta tggattctag attttatcgt ttattttttt   42900
aaaacatcat aaaacatgaa tgccattatg cttgttttaa cacaaaaaca cactcattta   42960
tgtattatca atgaattaag ccaggaacaa agatggcggc ttgcagttgg aacgtgcaaa   43020
cagtgctaat aatcactgcg ttttatagtt tgctttctcc agttaaggag cccattttac   43080
atttttaata caggacagtg atatggtgaa gagacatttt ggtaggagag caaatattgt   43140
ttaagagtcg tttatatcta ccgtgtacta agaaaaacaa acgtaaaaaa aaaaaaccc    43200
aacaaagctg tgatggatag ggactaagcc gaaaaggaaa ttaatgatta aatatatata   43260
tatgtatttg tgaataattt tgttcctgtt ttaaaatgtg gaggtactgt ttatttata    43320
catcgactgt attttgaagc catactttat ttaccagcga ggcccacaat ggaaacaacc   43380
cctgggcttt attgtgtttt tatcatcaac agtttaatta aaaaatttag gggctacttc   43440
tattttgta cagcttgtct aaaatctgtc aaataaaaat tcaatttaaa attcaattca    43500
attcaatctc ctgacttctg tgtgcagcca tgctgctgtt gtagctggtg tattccttgg   43560
aaattttcgt acccctcggt ttcgagtgtg gtcctggaaa atctctgttt caaggactat   43620
agtccttact cttagtccaa tgccttcaag ctaaagagaa ttgaggcagg aagggaaag    43680
ggctaagggg ttgaattggg attagcctaa gtgcctggag tctttttatc tcacttcaat   43740
atagaagtga tttacaatat agaagacgtt tcacataaag aagtgataag tgagctgtag   43800
caaaccaaac tgtggcataa aattttctat gacaagaaaa aaaacacaa catacaggta    43860
gttcacaagt tctctaatgc ttgcttttaa aggtcaggtg ttattcatta tccaaaatca   43920
tgctaatgat ataacagcgg cattgtttgc aagttcctat ttttatgaaa tgtgaaaagt   43980
cacctcgtca tcgttgacca gctccttctt caccaccttc atggcataga tgcgttctgt   44040
cttttgaga cgcaccagca gaactttggc gtagctgccc ctgccaatca ctcgcagcag    44100
gtcaaagtct attagaccca aactggacac cgcttttcct gattcccgac tgcccacagc   44160
ctgaaggatg catgaacgga gtattaaacc agtatcatac aatcatacat ttctgcttcc   44220
tggtttagat gttcttctct gtcctctctc tttgtttttc ccttgagccg cttgatttcc   44280
tatgactgcc acagagctac agagctcagg cccttaatca gatgctaatg accctgatgg   44340
aaggttactt tattagctgt acgaaaggaa atcaatagag ccgaatggac cttgtgcaca   44400
```

-continued

```
cccccatacc actgcatgag tgacaagtcc agcctaatca tcagtctgag agcgactgct    44460
gaaagctcat ccaatcacac actggtcata atagccacat ttacacctgc aactagcttt    44520
tatttagact gatttcatga gcaggtggag agtgttgaag acaaaccgaa ttttacaaac    44580
cacatttaaa aacattaaat aagcaagcag tcatttaaag aaaaaaaaaa tacaattgta    44640
agtcaacatt aacaactatt gctattatta ttttattgtg gtttaaatta taaacatcca    44700
acttaaaaat aataaataaa aatcattgat attctaatat aaaaatgtct tgatattaat    44760
acaaatgtat tcttacaata ctaatattta tacaaacatt atattttccc aaaaactcat    44820
tttttatgat atatttccaa ataaatcttt atccaaaggg aagcattgaa gattagttgg    44880
tgttgtatac agaaatatac atacaagttg acattttaca aatctaaatg acatctttta    44940
cattctactg accccaagt ttgaatgcga ggaaccctc attttaagct tattataaat    45000
gggtattatt tggaaaagat ttagcttcta ttcagttact ttattaccat ttaacactta    45060
tagtactgca tttatttatt taatcacata tttgtttcct tattatttaa ttttctgtat    45120
tattattgtt aattttatct atatgttaat aatatttagc acatttaact tgatgtgtta    45180
atgaattagt atattaatga tttattattt atatataaaa tctacagata taaataatag    45240 ataaactac tacaacgtat taatataagg gtaacactac aataagggtt gtattttcat    45300
tattgttagc taatccaatt actaacataa aaaattacaa aacactaagc atcacagtat    45360
tttttgtgtt agttaatgtt aaagaaaata catttgttta ttgtgagttt atgttactct    45420
tgcagtgcat taattaatgt taacaagcat gaatttagat tttaataatg cattaataaa    45480
tgctgaacta tggttaataa ataccgtcca agtatactta gttaattta gcaaatacat    45540 taacgaataa atgcttactg taaagtctga ccataattat tatatatatt gtaatcaact    45600
ttaggattat taatttttatt catcttaata aaaggctagg taatttagta gaaacgtgtg    45660
gttttatttg aataattaaa tgaagaattc ttttttaaaca tggacccct ggaaaaccct    45720 tttgacaccc tgagggttca caaaactgag atggacatct taggcagcag tattttactt    45780
gtttactagt aaatgcatta gctgagatga tgtagatgcc aggagcaaag catgtcttac    45840
ctcatgctcc tctccctcat gattgatgct ttctgttgag ttcttttttgc ccagaactga    45900 aacacaacaa agagaaacaa gaaaagtcat tgctcaatgc cctgcagaca ttattcattt    45960
atacacaatt attcgcaagc cgctaaacca aactgggcac tttgataaag cacaaaacaa    46020
caaggaattg aaatgtatct gaccagcact gtaactaaag ccacaagctt gttcccgtca    46080
ttaattccaa caaacaagct taatctagtg agaagactca cgcctgtggg ctgctcaatg    46140
catcactctg tttgagtgcg agcacaccta attactaaga ggaaacatca gcttaaccca    46200
tccagtcatt tcaaatccct caagatgaaa atcagtggcg tcaatgagcc actatagatc    46260
ttactgaatc aatttagcca cttaatgaat gcaataactc agatgagcat tgtttaacac    46320
ctctgcatta caagcttctt ttttagtcaa attgctgaca ataaaacaaa gtctgattga    46380
ctttgtatgt ttgcaaactg atctgttggt aaatgtttat cttaaaaagg ttgcaatcag    46440
aatatgcaca ttttacaatt taggttcagg aaagattgaa cttaagttgc aaaatatgaa    46500
tactgaactg tttaaattac taaacaatct aaaagttgat caaataaata cattgtttat    46560
tttatcagat atacgaaaaa tctgaacaag gtacaagagg ctgattattc attgacccga    46620
ggcagaatag ttagaactgt ttgaaagata aaataaatct caaaaaggca ttctttcaaa    46680
aaaatgatta gtctgcaatt caaattcaag taagaaagaa aaatctgata gacccgatat    46740
agaatacata tatgacaaag gcaaatatag atgagagcct gtcgtacctt gatctgggtg    46800
```

```
ctctggatga gtcgaccctg gatcgattct tccgatcatt gggtcctaga agaatagtaa   46860
gaaggtcaag gacagataga ctgagattca gagtattatt agcagtaata gcatctaatg   46920
taaaggtctt gaactagaaa aggaatgtga attgtgaata ggctctcttt agaaagtgct   46980
taatccaaca tgaattatgg attacttttaa gctttctttt tttaaagtaa taatgtaaat   47040
aatttcagca aaaaatcagc tttaatgaag aaaaaaaagt cacatacata aaatcaaata   47100
tcaatataca taaatcaaat gaacaacaaa ttttaatttt agatgaacaa tttaagtaaa   47160
atgtgaaaac aaaagtgtga aatttgtgaa attgcattta aatctctcgg atgttttgtt   47220
gcaatcctga gctttataac caaccacatt ggttggtttc acttacatgt ttgtttgcca   47280
tttcagattt tttttaaatg cattttttaa agagtcattg agatatacat attactgcta   47340
aaaatactac aggtaaaata aaaccattat ttatgtccgt gcacaactaa aaaataaaca   47400
aatttaagtc catgaatgaa gaaagggcaa tttatagatt ttttttctta tcgcgattac   47460
actactcata aatgttgttt gaatttgcca catacacgca ttgatcgaaa catccatttt   47520
attgtttact gagttcttat tcattttgct gtaaaaaata aacacactaa aaaggaatta   47580
tgattgtatt tttaatagga aactttggat ttctagtgat ggttattatt ttttaaactg   47640
caaaatataa ttgaagctag acacctggag agccacatat ttttggtcaa atagccatat   47700
gtggctagcg agccataggt tccctaccac tgttgaaaac agtttgttaa tcacttttta   47760
ttgttcattt ttaattgcta atagttttaa ccatagaaac cttaaattgt aacttcattg   47820
acactaatta cattattatt tttattttaa gccttaaaag ttaccctagt aatattccac   47880 tcatttttc aatgagcatt acaatgagtg gcctataaag ggttaattaa ttgaaggatt   47940
tgacacaatt gataagatca tgataataaa agctcaatgg aaatcaacag agaaggcaaa   48000
tggtgcaaac tattagaaaa gcaaacttct gaccatgcga atgcctcacc tgtattacct   48060
gtctaccaca ttctactgtg accagcttat ggcatttctt atgcaccaga agcttacagt   48120
tgatacactt gtatccctgc ctgcccagac cccagatacg atctgtgcag atggcacaat   48180
gagcacgctg tacaaaacaa agtgacaggc aaattaaagc aaaacacaaca tactacagag   48240 aaataaaaaa ataaaaataa aaaaaataaa tatatatata tatatatata tatatatata   48300
tatatatata tatatatata tatatatata tatataataa gagcatatac cctgttaaag   48360
cgtttggcct gaaacgcatg tccagtggca tagtagagtt tcctccaacg tcgagctccc   48420
cgccggtata tagactctga gtacaacaag tcaataaaat ctatgcacca cttacacaga   48480
atcaatgcag ccacaaaatg tatttttttt ttaaatatga tataaatatc agaaaacaca   48540
catactgtct tctccaggac agggcatgcc aggttttca gggacacaag gaaacactgt   48600
ggagagagag agagattgtg aaaaaacagc tcctgcatga cccctctgtg acctctcctc   48660
gtctgacagc ggataaggac tttgggtcaa caaacagagt ctgtccaggc ctacaaggtc   48720
agccggtgtg gacagtgtct attgacggac agtcggtggg ggtgttttc tgaaagccct   48780 tgtggccagc cgtcgtctcc tcagcataac taatgaactc acccagcagg cagaagaaca   48840
atgcatctct gtcaattagg cttgcatgat acttgtgata ttgtaaaatg tgatattgtt   48900
gagttttgcg ataacaatat ttcctgtgat ataacattta ccaagagaaa ttttatttta   48960
ttagctatta tttaaaatca tttatgtaat gatcctagta catatctatt tgtaattcct   49020
gtttaaagca aataactatc tgtatattct gttcatatct atctgcatgt accgaattat   49080
taatgaaaac ctgttcagta tgttaatcta taagtaaatc tcttattata gttaagaaaa   49140
```

```
cttatatatt atgttcacag tggatccatc tgtaaaaatt acccatagtt ttctatagtt   49200
gcactcataa tgtctaccta tatcctggac tcctggatgg acctaaaccg catttcgttg   49260
ccttgtactt gtgtaatgac aataaagttg aatataatct aatcaaatct acgaatataa   49320
acaggtataa ttaacctagt ttaggggaaa aaaacaagct atgaacattt agactttaaa   49380
acaatgtgaa gactataaac cttaacatga cattttttc ttattgccat ttccctgctt   49440
ctgatattag tatttatttt tcaaatctct gctctgaggc actagattca cctttggtaa   49500
taatagcatc tactgggtac aaaaataatt acaggtataa aaaagataaa ccctatataa   49560
ataacctttg catgcaacac aaatgcttgg aacataaaat aaagtgaatt taagtcgcac   49620
ctctgtgcaa tacagatatt gcacatacga ttatcgcaat aacaataatt tttcagtata   49680
agcagcccta ctgtcaaaca ttacccgaat actttctcat ttgtccaata agcatctgaa   49740
gacctgtatg actctgtagg gcttgttatg aataaataaa caaacacata tacccgagcc   49800
ataacatcaa aatgtggagc ttcatcagag ctcatcacta gggtcttgac atgcttgaaa   49860
gaatgcgtgt tattatgact catgtaaaaa taaactgttg atggaaacat taagatgtgc   49920
ataaatggaa atcataaact gagtaaaaaa tgcacaaaaa ctatgatgga aacactttta   49980
ccaaacaaat tccactatac gaataaaaaa aaaaagtca tgtgattttc ttttaagaga   50040
tcatgtgatg gtaaaaatgt gtgtgaatgg ataaaccagc aggttaagca cattgtaaaa   50100
catctgaaat gttgttttgg tcattctaaa acgccttaac catttcagca tccacgtgct   50160
ccatgtctca cgccttcaaa cggcaccaca tgttcactgc aagttgggat tgccttctga   50220
ggtgcaagtc atttattaaa taaagaaaac aattacgcaa aaaattccat ttttactgtt   50280
gatatttggc agcagttaat cagacagtga tgattttgtt ctctttgact ctgcgttatt   50340
tgcatgtact ttatgcaata ttccagtttc gcgcatacat ttaatttgca tctttggatg   50400
taaacatagc taatgacagc aaaagttgcc aattaaaatg cgaagaacac aaataattct   50460
aaagccaaaa ggtcaactag aaaaccttct cattaagatt gtgttacttt tttcacattg   50520
ttcaggttaa ggtgcataca aacaatcaga aaaactatat gcttgttact atatttgata   50580
gtgcattgaa ataatctcag ctttcaaatt atgataataa tgaactataa taagtttat   50640
aaactggtaa aagtacagaa aacaccatta acaataactc caattggttt atttcaatgg   50700
aaccttttca taaacctgtt atgaggcatt aaacagttgg gacaggacag caagtttact   50760
gttattctca cacaattgtt ttttccttt tctgaaagtt tttataccat catcgtggag   50820
ttttctttt attatttgag caaataagat ttttttcca aacttttttt gtattctcct   50880
attctctgcg ctctaagttt ttccaattat gatgacttct gctactgaga aacctggaaa   50940
tgtgaaaagg gtctattgtt tctctctttg atttggtctc tggttaattt cttctgttca   51000
gtctgtcatg atcagacatc cacacagagt tgcttaacag cagaaactga agagtagctc   51060
cacttaaaaa caacaatgat tgtttatcat gtttgttaca gtaaacagt ttgatttgat   51120
aaaatctact ctattaagtg ctatttacta gggctgcaca acattggaaa aatataacaa   51180
aattttgtta ttctccaatt atatattgca atatgaatac aatttctcca gatgacttta   51240
tcattttagt taattgtttg ggataattct gcaggtgcat ttgcaaaaaa cctaagaaag   51300
atctctacaa gcataaaaaa atgcaataaa aaaaattata taaactgtta ttcattgttt   51360
tcctgaatac taacagtaga cataataata ctgcatagtc tttgttgtat aaataataca   51420
ataaaattat tggtatttaa tttaaaattg gttcaaattc ttatgcctga atgttttaa   51480
atcccttaa cggtcacatg cctcaaatat gaatgcaaat tatgaattat aatccaaaat   51540
```

```
caacattgca tatcatgcat tgttattgta tattgtacag ccctactata tacaacaaac   51600
aaaggtaatg taactgatgt atcaaattac atctatgtct attttcttat tgcgaagaaa   51660
accaaactac atatttacat tctgatctaa acagtgtagg atgatgacgg gatgttctct   51720
gctcagttta ctgctgctct gggcatttaa atttttttcc agaacaaaaa aagaactttg   51780
ctgcgagtac atcggggcct taagacctgg tgtaaaactt catccctcat aattctttca   51840
agaatcgaga gagcacaaaa gcaaacgcac tctagctaac ccacatcaaa agccaaatcc   51900
cagcataccg tgaataatga gctccgagtc tttgttgagt tcatatagac gcaaggcctc   51960
ctccagctcc agctgagaag aaacggtgca cggatcccct gaaatgacaa gcacagagaa   52020
cgctcaaaca caactctcca ccaaagacat cagcataact gacattgcga agatacaaac   52080
gaggcgagtg agggagaatt taagcaggcc tgagaaagag aaaagaaacc gagcgctctg   52140
atcatatgga gcgtaaagaa aatatctgtt cgattgacat cataaagccg taacacggcc   52200
catggtgttg tacgaagctg acgtcaatgc tgttgtctga agagtagcct gtggcaccaa   52260
cttcttgcac agacgcacac ggctttcaat caaacatcac agagaaggca atgagcgacg   52320
gcgggcatcg ctgccaaggc ttgcgcagac agacgggatt aacttctcgc catgacggcc   52380
cgctcagatc agctatgcta atgagcagcg tgactctggg ctcagcgtgg cacggtgaag   52440
attttggtat ttaaatgaat tttcttccat ctccatttcc catctcgcat gactaatgca   52500
gcagttaatc atcgcgcgca gtcaatcttt ccagcataaa accccgctcc ctgctgtgtg   52560
ttgcattcag attcgcatta ttcctcatgt aaaagccatc tattttagtt ctgccggtgg   52620
agtccagggt aattcggaga ctttaatgca atctgccaaa agtggcttca tttgtaatat   52680
ataaagtgct ggtgcaaatg aggcaggcgc ttcaacagaa tggcaggagg aagcttgttg   52740
ctacggcgac agttaaagaa acagaaggaa aggccacgtt tacacctggc attaacatct   52800
gtctcaaggg atttgatcaa gcggacagca ctaaatgcag gttcaaataa agtgcaaaag   52860
attttgtgat gactcgaatc ccatttgtgg ttagttaaac acacacactt tatttatatc   52920
atcaatgctg atgcatccag gacatacaac acaaaattac atattgcata agatgcaata   52980
acatattaaa atatgataat aacaacaatt tagtatgttt aatgtctaaa ttgaatgaac   53040
tgtcttgaaa gaattcagac atgatctact gggattttca cacacaacca tttctagggt   53100
ttatagagaa gggtctgaaa agaaaaaaac atctagtgag cagctgtttt gtgggtgcaa   53160
atgccttgtt gatgccagag gagaatggcc agactggttt aagctgatag aaaggcaaca   53220
gaactcaaat gaccagtcat tataactgag gtatgcagaa gaacatctct gaacgcacaa   53280
cacgtcaaat ctgaggcaga tgggctacag cagcagaaga ctacactgag tgccactcct   53340
attagctacg aacaggaaac tgaggctaaa atttgcacag gctcatcaat atagtttgga   53400
aaaatgttgc ctgctctgag ttttgatttc tgctgcaaca ttcagatggt agggtcagaa   53460
tttggtgtca acagcatgaa agcatgtatc catcctgcct tgtatcaacg attcaggctg   53520
gtggtggggg tgtaatgtgt gggggatatt ttcttggcac actttgggcc cattagtacc   53580
aatcgagcat cgtatgaaca ccacagccta tctgagtatt gctatgttta atacctaaat   53640
tgaatcaact aggagcaagc aaaatcatgt cttgaattaa ttctggcact aatatggccg   53700
ttcagcatta gtataacatc gaaaagtgca ttttattgtt aaacagtaaa ataaacatta   53760
aactattcat gaaggtgacc cttattctca agcaactaag acgatagcct ataaaacagc   53820
tcatttagaa aaatgggtca attaagtgta atagccaaaa ttcagtttta acaagtaaaa   53880
```

```
gctctctttg gtttaacaag ctgtgtgtaa tcatgaaaag agagagaggg tctctttagt    53940
gaaacctgat ctaaagaagt cactagagat tcatgttaac caggagtaaa tgtcaatctg    54000
tctcgactga ctgagatcac ctgagacaga tgccaacacc tactgtgaat agagcaaaga    54060
gacacaaaaa tgaaacaaca aaccttcctc atcaatccat ttcatggtga agagctggtc    54120
attgtccatg gagcacatat cacgcacctc attgcagagt ccctcatagg agatcgaagg    54180
ctcaaaatgt gtgatcatga tgtccctaaa acagaaaaaa aagtgacatt cattaaaatc    54240
ctacatttta gggctgcagg atattagaaa aatctgacaa tgcaatgttt tgttttctg    54300
tgatgtgtat ataatttccc cagatgactt taaatacctc gatttggtat gaaccatat    54360
acagaattta atcaaatgta aaatagcagt gcttagattt cattgcataa ataaatcaat    54420
tgaatatttt ttattaaaga ctggtacaat tttcatgcct gaatgcttta aactctcttg    54480
atatgcttta atcacaggcc tgaaaaacac atgcaaataa aaacttttg ctttattatg    54540
gaataaatct tcaataactg tggctcatgg taaactatat tcacaaattc aacattgcag    54600
atcctgcaat ctgactacta cagatgcaca tatttcaata tcaatgttaa acaatatat    54660
tgtgcagccc tactcttgaa aaattaaggt ggggcgagag gaaaaattta tttaatcaat    54720
tcatagttct ctaatatata ttagggatgc tctgatcaat cggctggaga tcagatttga    54780
tcggtcctca cttatctggc tgatcacatg aaccaaactt aatgttagat tacaggttta    54840
caagcagagt aatttacatt ataacttatt atgcataaaa aatgcacttc gaactttttc    54900
ttcattgagg catgttgact tattcttcca tcatttgttt ccaaattgca ttgtcagtca    54960
tggtacccaa ccccacccct aaacacaact gtcattgggg gatgagtaaa ttgtacttaa    55020
ctgtaccagt gagattgtaa gaattcccac cccatccact aaatcaaaaa cttctgaatt    55080
gtctagagat agcattggtt attcatgttt ctatccgcat ccctgtaaca gcatgcaata    55140
ttgtgcttat ataagtatg aaaaagtacg actgtataca atataattta ttaatccaaa    55200
aataaacaat aaagggtaac attttttatt ttatgaccat tcgatatata tctataccat    55260
cataatgcac agccctccta aaaatatgat aaataattta gtgtgggata ataagagaaa    55320
tctaaatact atattagtac attttaagac caaaaacaca gtacatggag tatcagagat    55380
ggcgagtttc aaggaagctg taatactagc atattcccat agcaggaggc acacagcagc    55440
ttcttactct ctgttgtcta ccgagttcac actgttttgg ttaattatta acagcaggga    55500
gtctttcctg tctacgagcc agtgcactga cccacacatg cctgcgagcg gccactgcaa    55560
ccatcccaca catcacctta tgacgaacca aaaaaaaaag tgctgctttt atctgatcca    55620
ggactattac gatcaagcta ctgtacgaga cataaaaggc agttatgcat gtcctgtgac    55680
aaatatctct gagattataa tagctccgca ttactaaact actagtgttt agttcatatt    55740
tacagagaga gacagattta ctcttatcat tgcataaacg atataacaat attctggcat    55800
ataactgaag gttttgtgcc cactatctta gtagtgagag atgcatcctg tgaaagcgca    55860
gcatctctga aaggaagcag caaagccaca ttcctctgta gggcatacct ggatcagtac    55920
acactgcttt tacaacaaca agcatgatga gcaaacattc agtcccatgg tcaaatacga    55980
cttacaagaa actcaaacac gattttctga acctgaattt gtaaggaagg cttacgggga    56040
ctgagtcaa ggcactatac taggaatagc acacaaggaa atatgaccat tcctttaaag    56100
caaacaatag gtgtattaaa gggaaagttc gctgaaatga tgtcatcatt taaggtgctt    56160
tcatactagt ttagctcata ctttgttta acttcaaaca atttatagtt ctgatgagct    56220
ttaagaatgt caggtgacac tacgttaagc aaacaatgat cattaaatga caccacactt    56280
```

```
tttaaaaata actataacac attcaaaata tgaccttaaa ctttccagca tcttttaaaa    56340
aaaaacacaa ttcaatatat aacttccaaa atggtaaata tgcattctgt ggcacttttt    56400
accaatgcta acattgcagc attttcgact ctggtattaa actatacctg caacatcat     56460
gactacaatt aaaaaaacaa gtgtttgctg cacattaaga ctgccagatt ttacattcat    56520
ttaagttata ctgcaccaac agcagtggtg gttcagatga cataatagtt tttgagtcac    56580
ggatcggacc attttcgga tcagcaaaaa aaggaaggag acaaatgtca attgctttca     56640
attcatgcaa aaatataagt gcaaaagcca ctggttttaa aaaacagaac ttagaacctt    56700
taattttcat aaaaatctca atttaaaaac aaccggctga aaaaaaaagg aaaattttga    56760
atacgaaaaa tgatctttgc tactttagct gatgatgcta aatatataaa tctaacatat    56820
tgtacagaaa atcatcttta ttttcaatta atgattcaac aattcacact taaagtttca    56880
tgtttcatta aagttttatc attttgaaa accggatttc agtctttacc ataaacatca     56940
gtgtctttat ctgaactata aactcttctc ctgtgttatt taattgcttg taatgaactg    57000
aaagtgtaaa aactgaatct ctctcggtca aacacagatc tgaatgcagc acttacact     57060
gaatgcatta attcaggcta aacagtgaca gaaaacactt ttaattaata acctaagaaa    57120
gcatttacgt aggtcccacc acaaccgtaa tccataatca ttatatttca caggaagcc     57180
atgatgcttt catacatgtg atttgaatga cactcgaggc aatctgtctg caattgttat    57240
aaatgttgga ttaacctaca agtttaaaaa gttaataatc cgtcattaaa catgtgcgtt    57300
ccgaactgtg ggttgtgatc tgtatggatc acgaacaaac cgtgatcggt tacacccccta   57360
accaacaggg ggacaataaa tatttttta ttttaatttc aaattaaaag gagctgtcaa     57420
aaggtggaaa aaaacatat tgaccaatca atacagattt tttacatttt ttaaatgtcc     57480
aacccatctc attgttagac atgnnnnnnn nnnnnnnnnn nnnnnnnnnn nnnnnnnnnn    57540
nnnnnnnnnn nnnnnnnnnn nnnnnnnnnn nnnnnnnnnn nnnnnnnnnn nnnnnnnnnn    57600
atctctgttt tttattatat atatcctggg gtatcccttc aagcaagaaa aacaggggac    57660
taaaatgtag atctatctgc agaattttca ttatctcaat ctttaccct tgccaaaatg     57720
cacgtatctt cggacattcc caaatatat gtgcgtgatt ataatgagct gtttttaatg     57780
tctaaaaatg aatggaggta ataagacct gaagtctcga gtcaaaaaga ttcaaatggc     57840
tgcaaccgct tgttcatgaa gaataaggta aataaatgca ctcatgcaac atggattttt    57900
tgctttaaat gctattacag tatttaatgt taattcatg aacaaataaa actttacaat     57960
taaagtgtta ctataaacat attaaaattg gaattattaa aattaatatt aacaatttag    58020
tgttctcaca aattagagat tggtaatgca tataaaaaaa tcaagaaaaa gtttaaagaa    58080
aataatttta agtgacaatc taaactattg cagacagaga aggggccacg agccaagcac    58140
atctctactg tggaaaatgt tttagcttaa tagttgcaat ataggtcaaa tctgaaatgc    58200
ttattacaga catactacat gtgaccgaga gaacagaaaa ggatcatgca tgagtgatag    58260
aaagagcaat aaaaggaaga actaaggcaa gaggaggaga ataaagactg aaattcatct    58320
tagccaggct tcagggcctt tttaatcaga atataaaagg tgcagagagt aaaatgtcct    58380
tcaatttatt cagtggtcta cctgcagtgg ttctcaaata gtggtatgca taccaggctt    58440
ccttcgagtg gcacacagac tatcgctgac taattaaagt aaaaaaatga acacacccttt   58500
caaccctttg atgcatatga taacacctga tgtgattagt aaattgatag gctaaacctt    58560
ttattttaat ttttatttta ttatgtttgt tatgtattct atcatctgaa gctaatcttc    58620
```

-continued

```
tcccaatatt tgtaacgctt gttgggggcg tatccgtttt tttaatatcc cattgttgat   58680
tggtatgatt taatgaactg cttttctgac acacaaagct tactctaaca cgcagtcagc   58740
agatctaatt gaaaatttaa atatgcaaat catctatttc aaatatgttt agatttcaaa   58800
gataaacaaa tgcatgcaac atatttcaaa aatgaaagat tttgaaaaaa agagtttata   58860
tacgaatatg atgacatata gcctatattt atgaggccca aggaacattt cctggtttta   58920
atgaataggc ttttatatgt taatacttta catttaagta cagcagtttt cttttaactt   58980
tttaagaaca gtgctgtttt aatctacttt taaaagcaca tttaactcaa acattattta   59040
tttttttaca tgtgagcaca gtgcagtgta atgttccaa cgatttaaaa tgttttaagt    59100
ggctgacaat aataaatact cataatagaa attaatctgc ccgcttttga actgtgcaga   59160
gttgtagctg cttaattagg cctgctacgc tactgtattt taatactgat cataatggtg   59220
gtacttggag atagggctat gcgattaatc caaattgaat cgcaatcaca atttgaaaag   59280
ttgtgattag ttaaatcgca caaggctgca atataaaata tatatgtata tatgtaaaca   59340
aaaataataa ataacatttt caaaaacagt ctgctatgct ttagaaaatt acacatgcta   59400
gacattctgt gatagtgttg tgaggtatcg cagacatggt atcatttttc atgaactacg   59460
ccacattaca caagaagaaa agactgaatc ttgtatcacg aagtccagtt gtcctctatg   59520
gcttcccatg acaccctatg tcaaggaaat cgtgccgaaa tcatgtgatc tgaccggggc   59580
tttataacta gccaactgag tgagcaattt cattcagctc aatcagaaat gcgcaactga   59640
acttcggcca cataaaaaaa agaaaacaaa caggaaagcg ctaacaagtg gaattatagt   59700
gtctgcttct ccagaagcat taatagacaa attaatataa atgaaaaaca gtatttgtta   59760
tatgggaata ttttggtttc aaagtcacag acgccaaaca aaaataggca attttttaaga  59820 gctgttgcag aaatgtttac actgcttaaa gactattaag ctaaaactaa aattaaatta   59880
aaatcaactt gaagcttgta ttaaatttta aatcaagtcg caatatgtca aaaaataaat   59940
aaaaaaataa atagcaacta gatatattgc ccaactggca cagccctact tggagagaca   60000 atttttttctg aggtgatact tgctgaaaaa agtttgagaa ccactgcatt caggcagaaa  60060
cctgccatta aggcctccac acaatccctg attccctcaa tcacatccac agtagaagtt   60120
tatatggaaa gggggttgaa actgattcaa atactgtcta aaatgaccta ctggaaaaac   60180
aacagaaacc agagaaaaca cacattcaga cacaaatggt gggtttcaag atagtccaca   60240
ccctgaaatt ctgaccgtct attttttatac ggcatagacc atcaattcat gctcactcca   60300
gagttttcaa aaggatttca tatcctaaag gatttaactt tattcactga aacacagatt   60360
tccaaactaa aagattgtac agtggcctgt ggcatggtaa acctgtcggt tccttacaat   60420
gatggtaaat aaattcttat caacaaattc acctgaaaca gaaactgact agtgtcaaga   60480
caaatgcaca tatactatag aactgaagag taaaaagagc aatcagtctc caacaggtct   60540
gacaaaagat acttgtcata caagtttttc aggtgcatga caagaggaag cgtcatcacg   60600
aagaaatagc tgactaaaaa tcagttatac ataaatgtgc tttattattt acatcaagta   60660
aaaatatttc ataataacta cacctttttc caacaggtca cttttccccc tagcttacac   60720
tgttatacag aatcttctaa atgtgacaga tagtgagtcg gctttgtgac agggaaagcc   60780
ctaagatgaa acaacacacc atataaacca ctgttatctt aacagtaaat cactgtgttt   60840
atgtgaacaa ctataggtga agacgaaaga cgagatacag agagagtaat gaagaaacag   60900
ctcatttgtt atggttggtt tcagttgaca acttcatcag agtttgtttt tgagcttagc   60960
taacgtagct tgctagctgg cttttcattg gtttctgaaa atttgcaccg ttgagaataa   61020
```

```
gtgagaatgc aattgtatat ttaaacggtc tcactggcta cttaccctct gtagtaggct    61080
tttacccgga cttggtgcgg gttttctccg gggtgggaca tggtgctgtc ccgcagcgtg    61140
ggcattatgg actatccgta ctcctgctag cttagctaat gatgctagcc agctatcgtc    61200
tgacgaggaa aaactaccgg agttttaaaa ctaaacgtat tctttggaca gcaatagtgc    61260
cgtctccggt taaataaaca gcctggctga aatataatta gtgaagttca gacggaaatt    61320
aatcggacta ctagaagttc tgtcagacgg ggaaacactc ccttcttctg tcgcgcaggc    61380
ctcgagacgg actgatccaa acagcggaat gtggaggggg aggatgagag ggggatttcc    61440
agaagaaaaa tattttacag taacagcgat tgattgtcac acaacaacaa caaaaaaaac    61500
ttgtgactgt agttttaaaa agggtacaaa tgctaggcat ctgcaatatt gctgatgata    61560
gagtattatg gcaatatggt tcaatgggtc tagttgaatg ggagagtctg gtaacattcc    61620
gattatacca cacagaaatt gaagagggtg gagaacagta gcctttatag gaagtacatt    61680
acactgcttt ttgtgggtct atgaataatt gaatttggag ggacgcgatt aatgaagaaa    61740
ttaacgcttc tgtttaattc ttaccttcta cttcccagag tgaacgtact aaaaaatcca    61800
gccgcaaaaa cttcatagcc ttttaatact cggacaaggg cagtttctta aactgtgtac    61860
aatattaaca ggggcagttc ttaataatag agggcccata tacctagata aataaaaatt    61920
gtccctgttt ttctttatta ggatgttttt acttttgaac ttgtaaatcg tcacatgttt    61980
ccacatcaga aaaagccttt atatttaacc aataaagcaa aatcttagca atgttaaatg    62040
acatctcctt taaccaataa aacttcaaaa tatttgccat ttgctttata tagcctaatt    62100
ggaaaacaga aactaaatga gacatatcag cacacattat gctctcaagg cacgatggta    62160
tgaaggacga aacctgcaaa aacaataaat aaatacgcca atatataaat aaattagtaa    62220
ataaatctat aagtccctgc ataaataaaa taaataagta ataaataaat aatcaaataa    62280
tcaaataaat gaatattaaa atccacaaat tcctgcataa ataaatattt aaatgaataa    62340
tgcgggtagg caaattatta aataaattac acaaagttg aggaattagg aaaatgctaa    62400
actgaaagtt tatttacccct ctttcaaatg tatattcatc tattttcatt agcatgttga    62460
cttgaggaaa agtaaataca gaactatgtt caagaaatga ataagcgttt gaagggggaa    62520
ataatctttt acttttttccc ccaatatttg tgtaattttta tatacattta tttatttgca    62580
tatttttttt ttataattta ttaacacaat aatttctata gggaaaacac tatctattaa    62640
gctaacatct attaagtctc ttcttcatta agtctcttct gctcaccaaa cctgcattga    62700
ctccaaagta caacaaaaac agtcctatta ttattattat tattattatt attattatta    62760
ttattattaa tattattatt attattatgt ttatcaatgt ttattaacat ttaaattctt    62820 ttttgtttg atgtttaaaa atatcgaaag accagcattt atctgagata aaaatctttt    62880
gtaacatcat attaaaacat tgaatagctg aaagatagtt ttttgtcaa agattattgt    62940 aaaattaata gttttatata ccaaggatac tatgaacaaa agtgaggata aagtcattta    63000
taattttgta cattttaat tctggcaaat gcagttcttt tgaaatttct agtcattaaa    63060
gaaagctgaa aaaactcctc cctgtaagtc tgtccgcttt gcccaccagg atgtagatgt    63120
gtgtctgatg gactgaaatc ccacctgaaa gaagcagagg aacaggatgc taaaatactt    63180
agaaatgcaa atgaatatgg tattagcaag ctatcaaaaa ataagcagct gtgatcattg    63240
taatgtgttt tgtctctgct gtgcagtctg ttgtccagcg gagggttccg gaaactgtgg    63300
gatggcttct gaaggttgtc tgtcgtttca agatggccaa ccattctggc tcaagctcaa    63360
```

```
gcttctcgaa ggagcttcct ccacaatctg caataacaaa acaactgaat ctacttctgg   63420
atctcacttc atactaaaac atgctggatg atggaaacag caggatattc attattgtta   63480
gcctgaaggg acaagcagct tgttattcat tttaaactca tatctatatt ttattcttag   63540
cctttttcac acatttcatt tctgaagcct gtaactgcaa gagatataaa agatttcaca   63600
tcgtcataaa caaacatgca agtcttttac aagtaaatta taatttttta tttaaaataa   63660
cttcaatgac actaagtttc aaatgtggat caaaaaatat tccgtgggca tatacgttat   63720
aacagatata ccgtacactc actggccact agtccaactg ctcgttaagg caaatatttta  63780 atcagccaat caaatggcaa caactcaatc catttaggca tgtagacatg gtgaagacga   63840
tctgctgcag tccacaccga gcatcagaat gggaagaaa ggtgatttaa gtgactttaa    63900
atgtggcaaa gttgtgccag acggcctggt ctgagtattt cagaaactgc tgatctactg   63960
ggatttacag agggttcaca agaacgatc agaaaagag aaatatccag agagcagcag     64020
ttctgtgggc gcaaatgcct tgttgatgcc aaaggacaga ggagaatggc cagactggtt   64080
ccagctgata gaaaggcaac agtaactcaa ataacccctc gtttacaact gaggtatgca   64140
ggagagcatc tctgaacaca caacacgtct aacctagagc tggataggct acagcagcag   64200
aagaccacac cgggtgtcac tcctgtcacc taagagcagg aaactattcg cacaggccca   64260
ccaaaattgg acaatagaag attgggaaaa tgttgcctgg tctcatgaat ctcgatttct   64320
gctgaggcat tcggatggta gggtcagatt ttgctctcaa caagatgaaa gcaaggatcc   64380
atcctgcctt gaatcaacgg tttaggctgg tggtggtgta atggtgtggg ggataatttc   64440
ttggcacact ttaaacccat tagtaccaat tgagcatcat gtctatgcca cagcctacct   64500
gaatactgtt gctgaccatg tccatcccctt tatgaccaca gtgtactaat gttctcccaa  64560
cttccggcag gaaaaagcgg catgtcattc atttattctt tttcttttcg gctaagtccc   64620
tttattaatc catggtcgcc acagtggaat gaaccgccaa cttatccagc ataagtttta   64680
tgcagcggat gccctttccag tggcaaccca tctcagggaa acattcacac actcattcac  64740
actcatacac tacagacaat tcagcctatc caattcaccc gtacctcatg tctttggact   64800
gtgagggaaa ccggagcacc cggtggaaac ccacacaaac agcctacaac agccgacaaa   64860
tcatttgcaa ctttgcaaca tttgcagccg acaaatctgc agcaactgct ttttgatgc    64920 tttcgtgtca atatggacca aaatctctga ggaatatttc cagtaccttg taaatgtatg   64980
ccacgaagaa ttaaggcagt tttgaaagca aaagcgcgtc caacccggta ctagtaaagt   65040
gtacagtgag ttttacaaaa taatatgggc ataactttgc catgatgaca acacataata   65100
ttttactaca tattttcaag atactattca gcttaaagtg ccaattaaag gcttaacaag   65160
gtaaattagg ttaacagggc atgttaaggt aattaggcaa gtcattgtat gactgtggtt   65220
tggtctgtag acaattgaaa aaaaacatag ctttagaaaa ctaataatat tgatcttttt   65280
ttttacccag aagaaacaaa taagtaaaa taaagtaaa taaagtaaaa tagtgtaaaa     65340
aaaaatcctt cttctaataa acatcatttg ggacaaattt gaaaagaaa agaaatttac    65400 aggagggcta atcattttta cttcatatta caatgaatgc catgtagtgt gtgaaacagg   65460
ctcaatccaa gctaaccaaa agctttcgtt tgtcaaaagc acagagtgac agtgaatgag   65520
gactcacctg gtgctgcatc agagttgagt tgagtgcagg tgagcagaga ttcagtatct   65580
ggacttcagg tgttctagaa gctcagcagc agcagcagca gcagggcttc ccaaagtact   65640
gctctccact tcctgtctga ggaacttctt cctgtgcaca agagcatttg tgttgctgta   65700
tactgataaa tggctcacga ataatcatgc agcaggaaga tgactttggg catctacatc   65760
```

```
tggagaaatt cagtgagaat gttttaattt cattagagag gagtctgatg tgcatcaaat   65820
ctattctaat ccagttcctg ggcgaggcag tggcgcagta ggtagtgctg tcgcctcaca   65880
gcaagaagat cactgggtcg ctggttagaa cctcggctca gttggtgttt ctgtgtttct   65940
ccctgccttt gtgtgggttt tcttccaggt gctctggttt cccccacagt ccaaagacat   66000
gtggtacagg tgaattgggt aggctaaatt gtccatagtg gatgagtgcg tgtgtgtgtg   66060
tgaatgtgtg tgtgaatgtt tcccagagat gggttgcggc tggaagggca tctgctgcct   66120
aaaaacttgc tgaataagtt ggcggttcat tccgctgtgg cgaccccgg attaataaag    66180 ggactaagct gacaagaaaa tgaatgaatg aataatccag ttccagctgc ttttaacaaa   66240
acagtaaatc tgactgcttg acactgaaaa ctggatttat aaaatgcatt gcaataatta   66300 taaacacta gatgtcattc actttaaaca aactaggtca aatttaaagt cccctctat     66360 tgcacaataa tggaactgtc caactgttgc tgtccaactt attattatta tttttttaa    66420 atgggcttaa tttaaattta ttaatttaaa tgggcctcat tgcaaagtaa atgattttag   66480
attctctgct ttttttgca atttatttat ttatttattt aaaaatgagg attggatagt    66540
aaaaattgtt acacgttaaa tcaattactt tcacagagta taaatataag aaactagtta   66600
ttatacactt agtttaagag taggcactaa ggcccaaccc tatttcacca aggtccactt   66660
attttaaaat gtctggcctc tcccctcact aatagtagtt atatagtatt aatctctagg   66720
tcaggtggtt ctcaaactgt ggtaacgcgg gcttcctgat agtggtacgc ggagatatca   66780
aatgtgtcat atgtacatgc tacatatatt tcaaaaatga tttatatatg aatatgacat   66840
atcatttatt ttattacata ttgcctatat ttctgaggtc caggcaacat ttccaggtgt   66900
tgatgaattg gctactatat gttaatactt tacatttaag tacaacactt ttcttactac   66960
tttttaaaaa cattaaccta acattttaa cttttaaaag cacattttaa tttaaatgtt    67020
gatgttctta gttttatgt ttgcttgttt ttttgtttt tttacatat aaacacagta      67080 cagtgttaac attcagacaa ttcataatgt ttaaagtggc tgacaataat aaatattccc   67140
aataatagaa attaatctga tacgttttag aactgtgcag agctgtagct gctttactgg   67200
gcttactacg ctactgtatt tcagtactgc tcattatggt ggtacttgga gagacaattt   67260
ttttctgagg tgttacgtta tgaaaaaagt ttgagaacca ctgctctagg tcaataatat   67320
ttatttaatt aaaactatga actcagagct ttatcttatg ctcatggtta cgagattaca   67380
gaaattcacg taaattaggt caaattgtct ttttactta tttaaaaatg ttaaaagaa     67440 ctgagaatta aacatgacct taataactcc aaaagatata ctttatactt tgtgaatgaa   67500
tccgtgtttt aaatagtcca gacagcgctt tacttctttg ttgaatgatt cagttgtttg   67560
acctaatctt ctcactcatt agacattact accacctact ggaagattta gattcttatt   67620
ttgaggatta tttatttt ttaaaaatat atttttttca tattaaaatg caataaagta     67680
caataaacgt tatttgaaat aaagagatag ttcacacgca caaattatt ttgtcatcat    67740 atacacactt ttgtgccatt taaatctgta acaattttctt gttattgtgt gttcagtaaa  67800
tgtttacttg attaattctt tttacattta actcaataat gacttgaaat cttctgttag   67860 tggtaattc tgagtcaatt ttataacatt taacacagaa ttttcccaat agtttgcatt    67920
aattgacttc aggataacta ataatagctt taaagtggcc acctatcttt attttacccc   67980
aggaccataa aaaataaaat tacaatttaa acacacacaa acacacacac acacacacac   68040
acacacacac acacacacac atatatataa agtgtgtgtg tgtgtgtgtg tgtgtgtgtg   68100
```

```
tgtgtgtgtg tataaattgt aattttataa ttaatttatt atgtatattt attttattat    68160
atatatatgt gtgtgtgtgt gtgtaaattg taattttata attaatttat tatgtatata    68220
tattttttaa ttatatatat atatatatat atatatatat atatatatat atatatatat    68280
atatatatat atatatatat atatatatat atatatatat atacacacac acacacacac    68340
acacacacac acacannnnn nnnnnnnnnn nnnnnnnnnn nnnnnnnnnn nnnnnnnnnn    68400
nnnnnnnnnn nnnnnnnnnn nnnnnnnnnn nnnnnnnnnn nnnnnnnnnn nnnnnnnnnn    68460
atatatatat atatatatat atatatatat atatatatat atatatatat atatatatat    68520
atatatatat atatatatat atatatatat atatatatat atatntatat atatatatat    68580
atatatatat atatatatat atatatatat atatatatat atatatatat atatagtgta    68640
tatatgtata tatatatata tatatatata tatatatata tntatatata tatatatata    68700
tatatatata tatatatata tatatatata tatatatata tatatatata tatatagana    68760
tttttttttt tttttttttt tttttttttt ttcgcttttt ttcgcttttt taagaaggtg    68820
gtttgtcttg gtcgggcatc tcagttgaga cctgtccact atgggtgacc ctaccggtag    68880
ctgtgaagta ccagtggcgt agctctcagc atcactgatg cacacaagcc ctcacagcac    68940
gtcaagctgc aaaccgtgtg agggaccota acctaccota acccaacagc caacactaac    69000
aactctaaca acaaccacta atgtgccaaa aaccactcag aggagaccag caacacgcaa    69060
gaaaccgcct aaacgcatgt caacctacag caaagcatcc aaaagaaccc aagagccgaa    69120
taccaacagc actgacaatc accaaaacac ccagcaatgt gatgaaaagt tgaattgaaa    69180
gtgaaatttg atgtattgta aacttattct ataactattt acaatatata cagtatgtac    69240
atacgtgccc atgatcctcc atctggcact aggatggctc agtgcctggg cttcttcctc    69300
cggggctcct tgggcagcgg ctccttgctg atgtccacca cgatatgagg ggggacactg    69360
gacccggatc tgacctccgt gatgaacaca cgtccatcag gctgctcagt ctctagcagt    69420
gcgggccggt ccagcttctc ccacagccgc tgctttagct ccaatccttg ctgaagagtg    69480
taccggcctg cacgcttctt cacagtggtg tccatcacac tccggtagat ctgctgatat    69540
tcctccacac tccgaccgtg gatggagagg ggctcctcct gtggcctctc acccactggg    69600
gagactgaag ctgcaggacg gagggcagga aggacagccg cgttccgcag gtgtcgctgc    69660
tccacggagg tgtcgcgctc cagcaagaag tccttgaggt gtccaggaag agtcctggtc    69720
cttcttgaac gtcgcagagg catgttgaac aacttcccaa actgatgaaa gtcagccaac    69780
aggagattag ttcagagttt agtagcgcgc tgatcgggat tgataacttt atagacagtt    69840
gtgtagattt gtaaaccaac tcaggttgcc gtggtgacag aatgacgagg aacatttaaa    69900
tttaaacaat aattgatttc agcgttaagt caattagagc agcacgagct gtgtgtttgt    69960
acagtctttg ttattaaata cagaaaatat tttaataatt attaggtata gtaataaagg    70020
gcccatatac ctaaaaaaat aaatattgtc cccgttttac tttaggatag ttttacattg    70080
taaatcgtca tacgtttcca cgtcagaaaa aaacattaat aatgtttaac caataaagta    70140
aaattttagc aatgttacat gacatcttct ttaaccaact aaatgagaca catcagcaca    70200
cattatgctc tcaaggcacg atggtatgaa ggacgaaaac tgcaaaaaca ataaataaat    70260
acgcaaatat ataacaaat aagtaaataa atccataaat ccctgcataa attaaataat     70320
aaataaataa atatgctaat aaataaataa attgaaaatt ccacaaattc ttgtataaat    70380
aattatttaa ataataaata gtgcgggcag gtaaataatt aaatagccta atttacacga    70440
atgttggggg caataagaaa atgctaaact gatgtttatg tttattcatt tattcacatc    70500
```

```
agcatgttga cttgaggaaa agtaaatacg taattatgtt caagaaatga attaacgttt   70560
gaagggggaa ataaactttt acttttcccc ttaacatttg tgtaattta tatacatttt    70620 atacacattt atttatttgc atatttattt atttattatt ttatttatac agggatttat   70680
gaattattta ctcatttatt tatatatttg cgtatttatt tatttgttgt ttttgcaggt   70740
ttcgtcctcc atacgatggt gagctcattt ttaacaatct ttttaaaatg ttatctaaaa   70800
aatataatgt aaatttcagg atgttttcca gagatttgtg taattttcat ccatattta    70860 gaaaaaccaa aactgaaaaa cacaaaaacc tgtgcatgta agaatgacaa tttgctttta   70920
gggatacatt tttttctgtg tagctgtcag tgtcgttcag gactatgagg cagtgttgag   70980
agtctttata tctgtgttct aggttgatgt ttgtaagttt tatggaggac agagaagaaa   71040
acctgtacct attcctgaag gcagtgatag tgacagcatt gatcagacaa taaggtaagt   71100
gaggaagaaa ttaatcaggg acagttcact gtaacaggtc gtagtttgtt atggaggtca   71160
ggcaattata ttaatttcct acaccatgtt ttggagatgc gtcttgccat agcagtcaga   71220
ggaggtgcat tctccaggtt actacaagca aatgatttcc tctaagtgtc tctaacacat   71280
tgtccagcaa acaaacgttt actcacttca acaagagatg aactcaccac tgaactgcac   71340
agaaaaagaa atgtggtata gtatccacag ctagtgtttt tcagcctgtg aaagcttgat   71400
gtgactattt ttaattttat aaatcgatgt tgtaatgtaa ttactataca cataagttaa   71460
atagacttaa ccattgtttg aattgtctaa gtgtaaaccg agataaaaga ctgtgtaact   71520
gcaagccccg tcagaatcag taattttaaa gacatggcgg aggaaaatgg aatttaatgc   71580
agcgcttctt gcctggtctg agacccattt caacacttta gaccttagaa attgagattt   71640
acctccagat ccactcttca aaatcagctg tgatgtgacc caaggggat gttcatataa    71700 ttatttacgt ttttgaggaa ctaatttaat gtataattcc taagaaaaac attgccattc   71760
agttccaaaa cactgcccta aaatagccac agccagtgat gggctgggtt gggttttgt    71820 taacctgaga atgttctaag ctt                                           71843
```

```
<210> SEQ ID NO 4
<211> LENGTH: 2261
<212> TYPE: DNA
<213> ORGANISM: Homo sapiens
<220> FEATURE:
<221> NAME/KEY: CDS
<222> LOCATION: (205)...(1965)

<400> SEQUENCE: 4
```

```
ccgcggttcc ggctgctccg gcgaggcgac ccttgggtcg gcgctgcggg cgaggtgggc    60
aggtaggtgg gcggacggcc gcggttctcc ggcaagcgca ggcggcggag tcccccacgg   120
cgcccgaagc gccccccgca cccccggcct ccagcgttga ggcggggag tgaggagatg    180 ccgacccaga gggacagcag cacc atg tcc cac acg gtc gca ggc ggc ggc      231
                             Met Ser His Thr Val Ala Gly Gly Gly
                              1               5 agc ggg gac cat tcc cac cag gtc cgg gtg aaa gcc tac tac cgc ggg     279
Ser Gly Asp His Ser His Gln Val Arg Val Lys Ala Tyr Tyr Arg Gly
 10              15                  20                  25 gat atc atg ata aca cat ttt gaa cct tcc atc tcc ttt gag ggc ctt     327
Asp Ile Met Ile Thr His Phe Glu Pro Ser Ile Ser Phe Glu Gly Leu
             30                  35                  40 tgc aat gag gtt cga gac atg tgt tct ttt gac aac gaa cag ctc ttc     375
Cys Asn Glu Val Arg Asp Met Cys Ser Phe Asp Asn Glu Gln Leu Phe
 45                  50                  55
```

-continued

```
acc atg aaa tgg ata gat gag gaa gga gac ccg tgt aca gta tca tct       423
Thr Met Lys Trp Ile Asp Glu Glu Gly Asp Pro Cys Thr Val Ser Ser
         60                  65                  70 cag ttg gag tta gaa gaa gcc ttt aga ctt tat gag cta aac aag gat       471
Gln Leu Glu Leu Glu Glu Ala Phe Arg Leu Tyr Glu Leu Asn Lys Asp
     75                  80                  85 tct gaa ctc ttg att cat gtg ttc cct tgt gta cca gaa cgt cct ggg       519
Ser Glu Leu Leu Ile His Val Phe Pro Cys Val Pro Glu Arg Pro Gly
 90                  95                 100                 105 atg cct tgt cca gga gaa gat aaa tcc atc tac cgt aga ggt gca cgc       567
Met Pro Cys Pro Gly Glu Asp Lys Ser Ile Tyr Arg Arg Gly Ala Arg
                110                 115                 120 cgc tgg aga aag ctt tat tgt gcc aat ggc cac act ttc caa gcc aag       615
Arg Trp Arg Lys Leu Tyr Cys Ala Asn Gly His Thr Phe Gln Ala Lys
            125                 130                 135 cgt ttc aac agg cgt gct cac tgt gcc atc tgc aca gac cga ata tgg       663
Arg Phe Asn Arg Arg Ala His Cys Ala Ile Cys Thr Asp Arg Ile Trp
        140                 145                 150 gga ctt gga cgc caa gga tat aag tgc atc aac tgc aaa ctc ttg gtt       711
Gly Leu Gly Arg Gln Gly Tyr Lys Cys Ile Asn Cys Lys Leu Leu Val
    155                 160                 165 cat aag aag tgc cat aaa ctc gtc aca att gaa tgt ggg cgg cat tct       759
His Lys Lys Cys His Lys Leu Val Thr Ile Glu Cys Gly Arg His Ser
170                 175                 180                 185 ttg cca cag gaa cca gtg atg ccc atg gat cag tca tcc atg cat tct       807
Leu Pro Gln Glu Pro Val Met Pro Met Asp Gln Ser Ser Met His Ser
                190                 195                 200 gac cat gca cag aca gta att cca tat aat cct tca agt cat gag agt       855
Asp His Ala Gln Thr Val Ile Pro Tyr Asn Pro Ser Ser His Glu Ser
            205                 210                 215 ttg gat caa gtt ggt gaa gaa aaa gag gca atg aac acc agg gaa agt       903
Leu Asp Gln Val Gly Glu Glu Lys Glu Ala Met Asn Thr Arg Glu Ser
        220                 225                 230 ggc aaa gct tca tcc agt cta ggt ctt cag gat ttt gat ttg ctc cgg       951
Gly Lys Ala Ser Ser Ser Leu Gly Leu Gln Asp Phe Asp Leu Leu Arg
    235                 240                 245 gta ata gga aga gga agt tat gcc aaa gta ctg ttg gtt cga tta aaa       999
Val Ile Gly Arg Gly Ser Tyr Ala Lys Val Leu Leu Val Arg Leu Lys
250                 255                 260                 265 aaa aca gat cgt att tat gca atg aaa gtt gtg aaa aaa gag ctt gtt      1047
Lys Thr Asp Arg Ile Tyr Ala Met Lys Val Val Lys Lys Glu Leu Val
                270                 275                 280 aat gat gat gag gat att gat tgg gta cag aca gag aag cat gtg ttt      1095
Asn Asp Asp Glu Asp Ile Asp Trp Val Gln Thr Glu Lys His Val Phe
            285                 290                 295 gag cag gca tcc aat cat cct ttc ctt gtt ggg ctg cat tct tgc ttt      1143
Glu Gln Ala Ser Asn His Pro Phe Leu Val Gly Leu His Ser Cys Phe
        300                 305                 310 cag aca gaa agc aga ttg ttc ttt gtt ata gag tat gta aat gga gga      1191
Gln Thr Glu Ser Arg Leu Phe Phe Val Ile Glu Tyr Val Asn Gly Gly
    315                 320                 325 gac cta atg ttt cat atg cag cga caa aga aaa ctt cct gaa gaa cat      1239
Asp Leu Met Phe His Met Gln Arg Gln Arg Lys Leu Pro Glu Glu His
330                 335                 340                 345 gcc aga ttt tac tct gca gaa atc agt cta gca tta aat tat ctt cat      1287
Ala Arg Phe Tyr Ser Ala Glu Ile Ser Leu Ala Leu Asn Tyr Leu His
                350                 355                 360 gag cga ggg ata att tat aga gat ttg aaa ctg gac aat gta tta ctg      1335
Glu Arg Gly Ile Ile Tyr Arg Asp Leu Lys Leu Asp Asn Val Leu Leu
```

```
                  365                 370                 375
gac tct gaa ggc cac att aaa ctc act gac tac ggc atg tgt aag gaa    1383
Asp Ser Glu Gly His Ile Lys Leu Thr Asp Tyr Gly Met Cys Lys Glu
        380                 385                 390 gga tta cgg cca gga gat aca acc agc act ttc tgt ggt act cct aat    1431
Gly Leu Arg Pro Gly Asp Thr Thr Ser Thr Phe Cys Gly Thr Pro Asn
    395                 400                 405 tac att gct cct gaa att tta aga gga gaa gat tat ggt ttc agt gtt    1479
Tyr Ile Ala Pro Glu Ile Leu Arg Gly Glu Asp Tyr Gly Phe Ser Val
410                 415                 420                 425 gac tgg tgg gct ctt gga gtg ctc atg ttt gag atg atg gca gga agg    1527
Asp Trp Trp Ala Leu Gly Val Leu Met Phe Glu Met Met Ala Gly Arg
                430                 435                 440 tct cca ttt gat att gtt ggg agc tcc gat aac cct gac cag aac aca    1575
Ser Pro Phe Asp Ile Val Gly Ser Ser Asp Asn Pro Asp Gln Asn Thr
            445                 450                 455 gag gat tat ctc ttc caa gtt att ttg gaa aaa caa att cgc ata cca    1623
Glu Asp Tyr Leu Phe Gln Val Ile Leu Glu Lys Gln Ile Arg Ile Pro
        460                 465                 470 cgt tct ctg tct gta aaa gct gca agt gtt ctg aag agt ttt ctt aat    1671
Arg Ser Leu Ser Val Lys Ala Ala Ser Val Leu Lys Ser Phe Leu Asn
    475                 480                 485 aag gac cct aag gaa cga ttg ggt tgt cat cct caa aca gga ttt gct    1719
Lys Asp Pro Lys Glu Arg Leu Gly Cys His Pro Gln Thr Gly Phe Ala
490                 495                 500                 505 gat att cag gga cac ccg ttc ttc cga aat gtt gat tgg gat atg atg    1767
Asp Ile Gln Gly His Pro Phe Phe Arg Asn Val Asp Trp Asp Met Met
                510                 515                 520 gag caa aaa cag gtg gta cct ccc ttt aaa cca aat att tct ggg gaa    1815
Glu Gln Lys Gln Val Val Pro Pro Phe Lys Pro Asn Ile Ser Gly Glu
            525                 530                 535 ttt ggt ttg gac aac ttt gat tct cag ttt act aat gaa cct gtc cag    1863
Phe Gly Leu Asp Asn Phe Asp Ser Gln Phe Thr Asn Glu Pro Val Gln
        540                 545                 550 ctc act cca gat gac gat gac att gtg agg aag att gat cag tct gaa    1911
Leu Thr Pro Asp Asp Asp Asp Ile Val Arg Lys Ile Asp Gln Ser Glu
    555                 560                 565 ttt gaa ggt ttt gag tat atc aat cct ctt ttg atg tct gca gaa gaa    1959
Phe Glu Gly Phe Glu Tyr Ile Asn Pro Leu Leu Met Ser Ala Glu Glu
570                 575                 580                 585 tgt gtc tgatcctcat ttttcaacca tgtattctac tcatgttgcc atttaatgca    2015
Cys Val tggataaact tgctgcaagc ctggatacaa ttaaccattt tatatttgcc acctacaaaa    2075
aaacacccaa tatcttctct tgtagactat atgaatcaat tattacatct gttttactat    2135
gaaaaaaaaa ttaatactac tagcttccag acaatcatgt caaaatttag ttgaactggt    2195
ttttcagttt ttaaaaggcc tacagatgag taatgaagtt accttttttg tttaaaaaaa    2255
aaaaag                                                              2261

<210> SEQ ID NO 5
<211> LENGTH: 587
<212> TYPE: PRT
<213> ORGANISM: Homo sapiens

<400> SEQUENCE: 5

Met Ser His Thr Val Ala Gly Gly Ser Gly Asp His Ser His Gln
  1               5                  10                  15

Val Arg Val Lys Ala Tyr Tyr Arg Gly Asp Ile Met Ile Thr His Phe
```

```
                20                  25                  30
Glu Pro Ser Ile Ser Phe Glu Gly Leu Cys Asn Glu Val Arg Asp Met
            35                  40                  45

Cys Ser Phe Asp Asn Glu Gln Leu Phe Thr Met Lys Trp Ile Asp Glu
        50                  55                  60

Glu Gly Asp Pro Cys Thr Val Ser Ser Gln Leu Glu Leu Glu Glu Ala
65                  70                  75                  80

Phe Arg Leu Tyr Glu Leu Asn Lys Asp Ser Glu Leu Leu Ile His Val
                85                  90                  95

Phe Pro Cys Val Pro Glu Arg Pro Gly Met Pro Cys Pro Gly Glu Asp
            100                 105                 110

Lys Ser Ile Tyr Arg Arg Gly Ala Arg Arg Trp Arg Lys Leu Tyr Cys
        115                 120                 125

Ala Asn Gly His Thr Phe Gln Ala Lys Arg Phe Asn Arg Arg Ala His
        130                 135                 140

Cys Ala Ile Cys Thr Asp Arg Ile Trp Gly Leu Gly Arg Gln Gly Tyr
145                 150                 155                 160

Lys Cys Ile Asn Cys Lys Leu Leu Val His Lys Lys Cys His Lys Leu
                165                 170                 175

Val Thr Ile Glu Cys Gly Arg His Ser Leu Pro Gln Glu Pro Val Met
            180                 185                 190

Pro Met Asp Gln Ser Ser Met His Ser Asp His Ala Gln Thr Val Ile
        195                 200                 205

Pro Tyr Asn Pro Ser Ser His Glu Ser Leu Asp Gln Val Gly Glu Glu
        210                 215                 220

Lys Glu Ala Met Asn Thr Arg Glu Ser Gly Lys Ala Ser Ser Ser Leu
225                 230                 235                 240

Gly Leu Gln Asp Phe Asp Leu Leu Arg Val Ile Gly Arg Gly Ser Tyr
                245                 250                 255

Ala Lys Val Leu Leu Val Arg Leu Lys Lys Thr Asp Arg Ile Tyr Ala
            260                 265                 270

Met Lys Val Val Lys Lys Glu Leu Val Asn Asp Asp Glu Asp Ile Asp
        275                 280                 285

Trp Val Gln Thr Glu Lys His Val Phe Glu Gln Ala Ser Asn His Pro
        290                 295                 300

Phe Leu Val Gly Leu His Ser Cys Phe Gln Thr Glu Ser Arg Leu Phe
305                 310                 315                 320

Phe Val Ile Glu Tyr Val Asn Gly Gly Asp Leu Met Phe His Met Gln
                325                 330                 335

Arg Gln Arg Lys Leu Pro Glu Glu His Ala Arg Phe Tyr Ser Ala Glu
            340                 345                 350

Ile Ser Leu Ala Leu Asn Tyr Leu His Glu Arg Gly Ile Ile Tyr Arg
        355                 360                 365

Asp Leu Lys Leu Asp Asn Val Leu Leu Asp Ser Glu Gly His Ile Lys
        370                 375                 380

Leu Thr Asp Tyr Gly Met Cys Lys Glu Gly Leu Arg Pro Gly Asp Thr
385                 390                 395                 400

Thr Ser Thr Phe Cys Gly Thr Pro Asn Tyr Ile Ala Pro Glu Ile Leu
                405                 410                 415

Arg Gly Glu Asp Tyr Gly Phe Ser Val Asp Trp Trp Ala Leu Gly Val
            420                 425                 430

Leu Met Phe Glu Met Met Ala Gly Arg Ser Pro Phe Asp Ile Val Gly
        435                 440                 445
```

```
Ser Ser Asp Asn Pro Asp Gln Asn Thr Glu Asp Tyr Leu Phe Gln Val
    450             455             460

Ile Leu Glu Lys Gln Ile Arg Ile Pro Arg Ser Leu Ser Val Lys Ala
465             470             475             480

Ala Ser Val Leu Lys Ser Phe Leu Asn Lys Asp Pro Lys Glu Arg Leu
            485             490             495

Gly Cys His Pro Gln Thr Gly Phe Ala Asp Ile Gln Gly His Pro Phe
            500             505             510

Phe Arg Asn Val Asp Trp Asp Met Met Glu Gln Lys Gln Val Val Pro
            515             520             525

Pro Phe Lys Pro Asn Ile Ser Gly Glu Phe Gly Leu Asp Asn Phe Asp
    530             535             540

Ser Gln Phe Thr Asn Glu Pro Val Gln Leu Thr Pro Asp Asp Asp Asp
545             550             555             560

Ile Val Arg Lys Ile Asp Gln Ser Glu Phe Glu Gly Phe Glu Tyr Ile
                565             570             575

Asn Pro Leu Leu Met Ser Ala Glu Glu Cys Val
            580             585

<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6
ctgtcccgca gcgtgggcat tatgg                                    25
```

US 7,771,931 B2

METHODS FOR DIAGNOSING AND TREATING DISEASES AND CONDITIONS ASSOCIATED WITH PROTEIN KINASE Cλ

This application is a U.S. National Stage application of, and claims priority under 35 U.S.C. §371 from, International Application No. PCT/US02/28410, filed on Sep. 6, 2002, and claims priority from U.S. Ser. No. 60/317,653, filed on Sep. 6, 2001.

FIELD OF THE INVENTION

This invention relates to methods for diagnosing and treating diseases and conditions associated with Protein Kinase C λ.

BACKGROUND OF THE INVENTION

The processes by which organs acquire global structures and patterns during development are highly complex, and likely involve multiple, overlapping biochemical pathways. In the vertebrate heart, for example, the first key visible step in this process is chamber morphogenesis, involving the fashioning of the atrium and the ventricle. Proper orientation of these two functionally distinct contractile units is required for unidirectional blood flow, which begins with the first heartbeat of an organism. Properly formed chambers thereafter are the substrates upon which further heart development is superimposed.

Over recent years, much has been learned about the molecular mechanisms that are responsible for the acquisition of characteristic atrial and ventricular cell fates (Fishman et al., Development 124:2099-2117, 1997; Srivastava et al., Nature 407:221-226, 2000). However, both embryological and molecular steps that fashion the higher order structures of these chambers have proven to be more elusive because, in part, unlike cell fate decisions, these steps can be studied meaningfully only in living organisms. The zebrafish, *Danio rerio*, is a convenient organism to use in genetic and biochemical analyses of development. It has an accessible and transparent embryo, allowing direct observation of organ function from the earliest stages of development, has a short generation time, and is fecund.

SUMMARY OF THE INVENTION

The invention provides diagnostic, drug screening, and therapeutic methods that are based on the observation that a mutation, designated the "heart and soul (has)" mutation, in the zebrafish Protein Kinase C λ (PKCλ) gene, as well as a small molecule identified in a chemical screen in zebrafish, concentramide, cause abnormal heart growth and development.

In a first aspect, the invention provides a method of determining whether a test subject (e.g., a mammal, such as a human) has or is at risk of developing a disease or condition related to PKCλ (e.g., a disease or condition of the heart; also see below). This method involves analyzing a nucleic acid molecule of a sample from the test subject to determine whether the test subject has a mutation (e.g., the has mutation; see below) in a gene encoding PKCλ. The presence of such a mutation indicates that the test subject has or is at risk of developing a disease related to PKCλ. This method can also involve the step of using nucleic acid molecule primers specific for a gene encoding PKCλ for nucleic acid molecule amplification of the gene by the polymerase chain reaction. It can further involve sequencing a nucleic acid molecule encoding PKCλ from a test subject.

In a second aspect, the invention provides a method for identifying compounds that can be used to treat or prevent a disease or condition associated with PKCλ, or in the preparation of a medicament for use in such methods. This method involves contacting an organism (e.g., a zebrafish) having a mutation in a PKCλ gene (e.g., the heart and soul mutation), and having a phenotype characteristic of such a disease or condition, with the compound, and determining the effect of the compound on the phenotype. Detection of an improvement in the phenotype indicates the identification of a compound that can be used to treat or prevent the disease or condition. In a variation of this method, the organism, with or without a mutation in the PKCλ gene (e.g., the has mutation), is contacted with a candidate compound in the presence of concentramide.

In a third aspect, the invention provides a method of treating or preventing a disease or condition related to PKCλ in a patient (e.g., a patient having a mutation (e.g., the heart and soul mutation) in a PKCλ gene), involving administering to the patient a compound identified using the method described above. Also included in the invention is the use of such compounds in the treatment or prevention of such diseases or conditions, as well as the use of these compounds in the preparation of medicaments for such treatment or prevention.

In a fourth aspect, the invention provides an additional method of treating or preventing a disease or condition related to PKCλ in a patient. This method involves administering to the patient a functional PKCλ protein or a nucleic acid molecule (in, e.g., an expression vector) encoding the protein. Also included in the invention is the use of such proteins or nucleic acid molecules in the treatment or prevention of such diseases or conditions, as well as the use of these proteins or nucleic acid molecules in the preparation of medicaments for such treatment or prevention.

In a fifth aspect, the invention includes a substantially pure zebrafish PKCλ polypeptide. This polypeptide can include or consist essentially of, for example, an amino acid sequence that is substantially identical to the amino acid sequence of SEQ ID NO:2. The invention also includes variants of these polypeptides that include sequences that are at least 75%, 85%, or 95% identical to the sequences of these polypeptides, and which have PKCλ activity or otherwise are characteristic of the diseases and conditions mentioned elsewhere herein. Fragments of these polypeptides are also included in the invention. For example, fragments that include any of the different domains of PKCλ, in varying combinations, are included.

In a sixth aspect, the invention provides an isolated nucleic acid molecule (e.g., a DNA molecule) including a sequence encoding a zebrafish PKCλ polypeptide. This nucleic acid molecule can encode a polypeptide including or consisting essentially of an amino sequence that is substantially identical to the amino acid sequence of SEQ ID NO:2. The invention also includes nucleic acid molecules that hybridize to the complement of SEQ ID NO:1 under highly stringent conditions and encode polypeptides that have PKCλ activity or otherwise are characteristic of the diseases and conditions mentioned elsewhere herein.

In a seventh aspect, the invention provides a vector including the nucleic acid molecule described above.

In an eighth aspect, the invention includes a cell including the vector described above.

In a ninth aspect, the invention provides a non-human transgenic animal (e.g., a zebrafish or a mouse) including the nucleic acid molecule described above.

In a tenth aspect, the invention provides a non-human animal having a knockout mutation in one or both alleles encoding a PKCλ polypeptide.

In an eleventh aspect the invention includes a cell from the non-human knockout animal described above.

In a twelfth aspect, the invention includes a non-human transgenic animal (e.g., a zebrafish) including a nucleic acid molecule encoding a mutant PKCλ polypeptide, e.g., a polypeptide having the heart and soul mutation.

In a thirteenth aspect, the invention provides an antibody that specifically binds to a PKCλ polypeptide.

By "polypeptide" or "polypeptide fragment" is meant a chain of two or more (e.g., 10, 15, 20, 30, 50, 100, or 200, or more) amino acids, regardless of any post-translational modification (e.g., glycosylation or phosphorylation), constituting all or part of a naturally or non-naturally occurring polypeptide. By "post-translational modification" is meant any change to a polypeptide or polypeptide fragment during or after synthesis. Post-translational modifications can be produced naturally (such as during synthesis within a cell) or generated artificially (such as by recombinant or chemical means). A "protein" can be made up of one or more polypeptides.

By "Protein Kinase C λ protein," "Protein Kinase C λ polypeptide," "PKCλ protein," or "PKCλ polypeptide" is meant a polypeptide that has at least 45%, preferably at least 60%, more preferably at least 75%, and most preferably at least 90% amino acid sequence identity to the sequence of a human (SEQ ID NO:5) or a zebrafish (SEQ ID NO:2) PKCλ polypeptide. Polypeptide products from splice variants of PKCλ gene sequences and PKCλ genes containing mutations are also included in this definition. A PKCλ polypeptide as defined herein plays a role in heart development, modeling, and function. It can be used as a marker of diseases and conditions associated with PKCλ, such as heart disease (also see below).

By a "Protein Kinase C λ nucleic acid molecule" or "PKCλ nucleic acid molecule" is meant a nucleic acid molecule, such as a genomic DNA, cDNA, or RNA (e.g., mRNA) molecule, that encodes a PKCλ protein (e.g., a human (encoded by SEQ ID NO:4) or a zebrafish (encoded by SEQ ID NOs:1 or 3) PKCλ protein), a PKCλ polypeptide, or a portion thereof, as defined above. A mutation in a PKCλ nucleic acid molecule can be characterized, for example, by the insertion of a premature stop codon anywhere in the PKCλ gene. For example, codon R515 can be changed to a stop codon (CGA to TGA), or codon W519 can be changed to a stop codon (TGG to TAG). In addition to this zebrafish Protein Kinase C λ mutation (hereinafter referred to as "the heart and soul mutation"), the invention includes any mutation that results in aberrant PKCλ protein production or function, including, only as examples, null mutations and additional mutations causing truncations. The truncations can be carboxyl terminal truncations in which the carboxyl terminal half of the protein (or a portion thereof) is not produced. For example, at least 10, 25, 50, 70, 75, 100, 150, 200, or 250 amino acids of the carboxyl terminal half of the protein can be absent.

The term "identity" is used herein to describe the relationship of the sequence of a particular nucleic acid molecule or polypeptide to the sequence of a reference molecule of the same type. For example, if a polypeptide or a nucleic acid molecule has the same amino acid or nucleotide residue at a given position, compared to a reference molecule to which it is aligned, there is said to be "identity" at that position. The level of sequence identity of a nucleic acid molecule or a polypeptide to a reference molecule is typically measured using sequence analysis software with the default parameters specified therein, such as the introduction of gaps to achieve an optimal alignment (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). These software programs match identical or similar sequences by assigning degrees of identity to various substitutions, deletions, or other modifications. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine.

A nucleic acid molecule or polypeptide is said to be "substantially identical" to a reference molecule if it exhibits, over its entire length, at least 51%, preferably at least 55%, 60%, or 65%, and most preferably 75%, 85%, 90%, or 95% identity to the sequence of the reference molecule. For polypeptides, the length of comparison sequences is at least 16 amino acids, preferably at least 20 amino acids, more preferably at least 25 amino acids, and most preferably at least 35 amino acids. For nucleic acid molecules, the length of comparison sequences is at least 50 nucleotides, preferably at least 60 nucleotides, more preferably at least 75 nucleotides, and most preferably at least 110 nucleotides. Of course, the length of comparison can be any length up to and including full length.

A PKCλ nucleic acid molecule or a PKCλ polypeptide is "analyzed" or subject to "analysis" if a test procedure is carried out on it that allows the determination of its biological activity or whether it is wild type or mutated. For example, one can analyze the PKCλ genes of an animal (e.g., a human or a zebrafish) by amplifying genomic DNA of the animal using the polymerase chain reaction, and then determining whether the amplified DNA contains a mutation, for example, the heart and soul mutation, by, e.g., nucleotide sequence or restriction fragment analysis.

By "probe" or "primer" is meant a single-stranded DNA or RNA molecule of defined sequence that can base pair to a second DNA or RNA molecule that contains a complementary sequence (a "target"). The stability of the resulting hybrid depends upon the extent of the base pairing that occurs. This stability is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are well known to those skilled in the art. Probes or primers specific for PKCλ nucleic acid molecules, preferably, have greater than 45% sequence identity, more preferably at least 55-75% sequence identity, still more preferably at least 75-85% sequence identity, yet more preferably at least 85-99% sequence identity, and most preferably 100% sequence identity to the sequences of human (SEQ ID NO:4) or zebrafish (SEQ ID NOs:1 and 3) PKCλ genes.

Probes can be detectably labeled, either radioactively or non-radioactively, by methods that are well known to those skilled in the art. Probes can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are well known to those skilled in the art.

A molecule, e.g., an oligonucleotide probe or primer, a gene or fragment thereof, a cDNA molecule, a polypeptide, or an antibody, can be said to be "detectably-labeled" if it is marked in such a way that its presence can be directly identified in a sample. Methods for detectably labeling molecules are well known in the art and include, without limitation, radioactive labeling (e.g., with an isotope, such as $^{32}P$ or $^{35}S$) and nonradioactive labeling (e.g., with a fluorescent label, such as fluorescein).

By a "substantially pure polypeptide" is meant a polypeptide (or a fragment thereof) that has been separated from proteins and organic molecules that naturally accompany it. Typically, a polypeptide is substantially pure when it is at least 60%, by weight, free from the proteins and naturally occurring organic molecules with which it is naturally associated. Preferably, the polypeptide is a PKCλ polypeptide that is at least 75%, more preferably at least 90%, and most preferably at least 99%, by weight, pure. A substantially pure PKCλ polypeptide can be obtained, for example, by extraction from a natural source, by expression of a recombinant nucleic acid molecule encoding a PKCλ polypeptide, or by chemical synthesis. Purity can be measured by any appropriate method, e.g., by column chromatography, polyacrylamide gel electrophoresis, or HPLC analysis.

A polypeptide is substantially free of naturally associated components when it is separated from those proteins and organic molecules that accompany it in its natural state. Thus, a protein that is chemically synthesized or produced in a cellular system that is different from the cell in which it is naturally produced is substantially free from its naturally associated components. Accordingly, substantially pure polypeptides not only include those that are derived from eukaryotic organisms, but also those synthesized in *E. coli*, other prokaryotes, or in other such systems.

By "isolated nucleic acid molecule" is meant a nucleic acid molecule that is removed from the environment in which it naturally occurs. For example, a naturally-occurring nucleic acid molecule present in the genome of cell or as part of a gene bank is not isolated, but the same molecule, separated from the remaining part of the genome, as a result of, e.g., a cloning event (amplification), is "isolated." Typically, an isolated nucleic acid molecule is free from nucleic acid regions (e.g., coding regions) with which it is immediately contiguous, at the 5' or 3' ends, in the naturally occurring genome. Such isolated nucleic acid molecules can be part of a vector or a composition and still be isolated, as such a vector or composition is not part of its natural environment.

An antibody is said to "specifically bind" to a polypeptide if it recognizes and binds to the polypeptide (e.g., a PKCλ polypeptide), but does not substantially recognize and bind to other molecules (e.g., non-PKCλ-related polypeptides) in a sample, e.g., a biological sample, which naturally includes the polypeptide.

By "high stringency conditions" is meant conditions that allow hybridization comparable with the hybridization that occurs using a DNA probe of at least 100, e.g., 200, 350, or 500, nucleotides in length, in a buffer containing 0.5 M NaHPO$_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. (These are typical conditions for high stringency northern or Southern hybridizations.) High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually 16 nucleotides or longer for PCR or sequencing, and 40 nucleotides or longer for in situ hybridization). The high stringency conditions used in these techniques are well known to those skilled in the art of molecular biology, and examples of them can be found, for example, in Ausubel et al., Current Protocols in Molecular Biology, John Wiley & Sons, New York, N.Y., 1998, which is hereby incorporated by reference.

By "sample" is meant a tissue biopsy, amniotic fluid, cell, blood, serum, urine, stool, or other specimen obtained from a patient or a test subject. The sample can be analyzed to detect a mutation in a PKCλ gene, or expression levels of a PKCλ gene, by methods that are known in the art. For example, methods such as sequencing, single-strand conformational polymorphism (SSCP) analysis, or restriction fragment length polymorphism (RFLP) analysis of PCR products derived from a patient sample can be used to detect a mutation in a PKCλ gene; ELISA and other immunoassays can be used to measure levels of a PKCλ polypeptide; and PCR can be used to measure the level of a PKCλ nucleic acid molecule.

By "Protein Kinase C λ-related disease," "PKCλ-related disease," "Protein Kinase C λ-related condition," or "PKCλ-related condition" is meant a disease or condition that results from inappropriately high or low expression of a PKCλ gene, or a mutation in a PKCλ gene (including control sequences, such as promoters) that alters the biological activity of a PKCλ nucleic acid molecule or polypeptide. PKCλ-related diseases and conditions can arise in any tissue in which PKCλ is expressed during prenatal or post-natal life. PKCλ-related diseases and conditions can include diseases or conditions of the heart or cancer (also see below).

The invention provides several advantages. For example, using the diagnostic methods of the invention it is possible to detect an increased likelihood of diseases or conditions associated with PKCλ, such as diseases of the heart or cancer, in a patient, so that appropriate intervention can be instituted before any symptoms occur. This may be useful, for example, with patients in high-risk groups for such diseases or conditions. Also, the diagnostic methods of the invention facilitate determination of the etiology of such an existing disease or condition in a patient, so that an appropriate approach to treatment can be selected. In addition, the screening methods of the invention can be used to identify compounds that can be used to treat or to prevent these diseases or conditions. The invention can also be used to treat diseases or conditions (e.g., organ failure, such as heart or kidney failure) for which, prior to the invention, the only treatment was organ transplantation, which is limited by the availability of donor organs and the possibility of organ rejection.

Other features and advantages of the invention will be apparent from the following detailed description, the drawings, and the claims.

BRIEF DESCRIPTION OF THE DRAWINGS

FIGS. 5D and 5E, C. elegans strain KK871, a stable expresser of a par2:GFP fusion protein, was treated with 34 µM concentramide and allowed to develop at room temperature. Nomarsid (FIG. 5D) and fluorescence (FIG. 5E) microscopy were used to visualize the asymmetry of division and par2:GFP localization after the first cell division. Posterior is to the left.

FIGS. 6A-6C, In situ hybridization was used to show Pax2.1 expression in untreated (FIG. 6A) and concentramide-treated (FIG. 6B) 18-somite embryos. The expression patterns have been false-colored blue for untreated embryos and red for concentramide-treated embryos. FIG. 6C shows an overlay of the images from FIGS. 6A and 6B. Arrowheads indicate areas of Pax2.1 expression at the midbrain-hindbrain boundary and in the otic placodes. The view is lateral, anterior to the left in FIGS. 6A-6C. FIG. 6D, The distance between the anterior edge of the heart field, as defined by cmlc2 in situ staining, and the rostral extreme of the zebrafish embryo was measured in wild-type (WT), concentramide-treated (conc.), and has embryos at the 18-somite stage. Error bars represent standard error.

DETAILED DESCRIPTION

Figure 1:
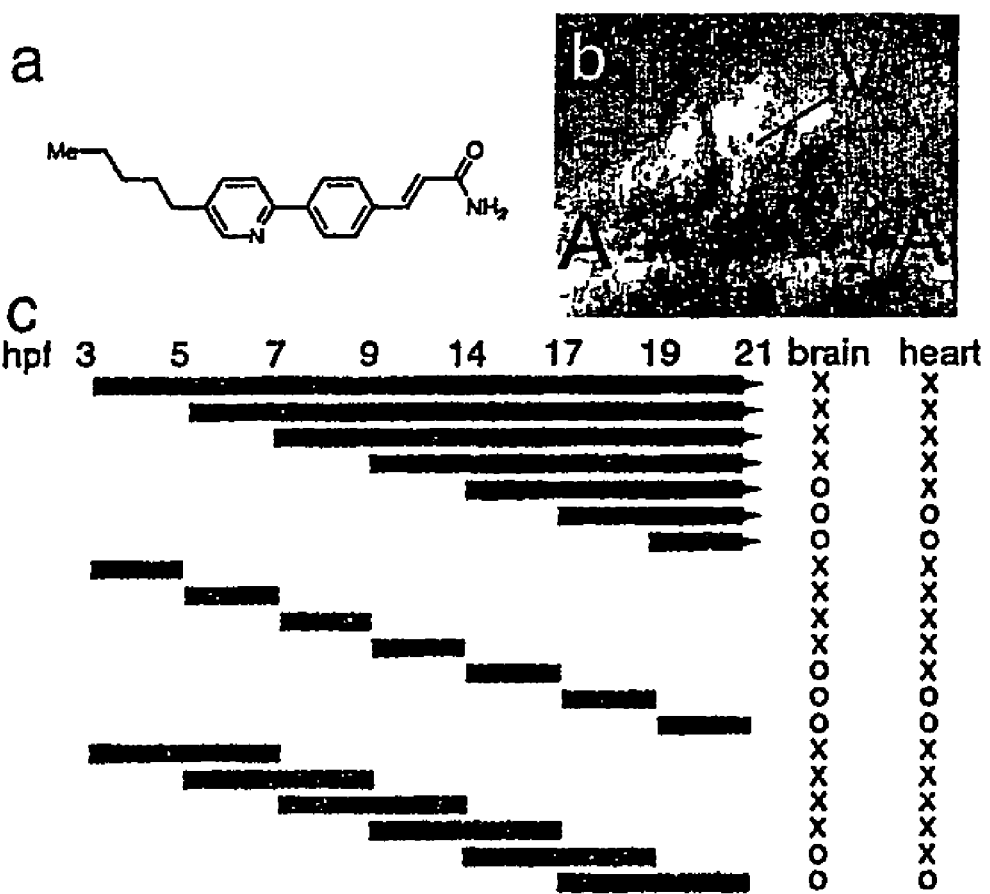
FIG. 1A is a schematic representation of the structure of a small molecule, concentramide, that alters heart patterning.
FIG. 1B is a lateral view of the mushroom-shaped heart of a live, concentramide-treated embryo 30 hpf. The atrium is indicated with A, and the ventricle with V.
FIG. 1C is a schematic representation of a timecourse of concentramide effectiveness. Black bars indicate the developmental time periods during which groups of embryos were immersed in water containing concentramide. An "x" indicates that treatment during the indicated time period alters the wild-type brain or heart phenotypes. An "o" indicates that the wild-type phenotype was observed. Blue and pink boxes mark the critical periods for development of the brain and heart phenotypes, respectively.

The invention provides methods of diagnosing, preventing, and treating diseases and conditions associated with PKCλ, such as diseases or conditions of the heart (also see below), and screening methods for identifying compounds that can be used to treat or to prevent such diseases and conditions. In particular, we have identified a small molecule, concentramide, and a genetic mutation, heart-and-soul (has), which disrupt the earliest heart. Both cause the ventricle to form within the atrium. We show here that the has gene encodes an atypical Protein Kinase C, Protein Kinase C λ (PKCλ). The has mutation results in the disruption of epithelial cell-cell interactions in a broad range of tissues. Concentramide does not disrupt epithelial cell interactions but, rather, shifts the converging heart field of developing embryos rostrally. What is shared between the effects of concentramide and has is a reversal of the order of fusion of the anterior and posterior ends of the heart field.

The diagnostic methods of the invention thus involve detection of mutations in genes encoding PKCλ proteins, while the compound identification methods involve screening for compounds that affect the phenotype of organisms having mutations in genes encoding PKCλ or other models of appropriate diseases and conditions. The compound identification methods can also involve screening of candidate compounds in the presence of concentramide, using organisms with or without a PKCλ mutation (e.g., the has mutation). Compounds identified in this manner, as well as PKCλ genes and proteins themselves, can be used in methods to treat or prevent diseases and conditions associated with PKCλ. Compounds, antisense molecules, and antibodies that are found to inhibit PKCλ function can also be used to prevent or treat cancer.

The invention also provides animal model systems (e.g., zebrafish having mutations (e.g., the heart and soul mutation) in PKCλ genes, or mice (or other animals) having such mutations) that can be used in the screening methods mentioned above, as well as the PKCλ protein, and genes encoding this protein. Also included in the invention are genes encoding mutant zebrafish PKCλ proteins (e.g., genes having the heart and soul mutation) and proteins encoded by these genes. Antibodies that specifically bind to these proteins (wild type or mutant) are also included in the invention.

The diagnostic, screening, and therapeutic methods of the invention, as well as the animal model systems, proteins, and genes of the invention, are described further, as follows, after a brief description of diseases and conditions associated with PKCλ, which can be diagnosed, prevented, or treated according to the invention.

PKCλ-Associated Diseases or Conditions

Abnormalities in PKCλ genes or proteins can be associated with any of a wide variety of diseases or conditions, all of which can thus be diagnosed, prevented, or treated using the methods of the invention. For example, as discussed above, the heart and soul mutation in zebrafish is characterized by abnormal heart growth and development. Thus, detection of abnormalities in PKCλ genes or their expression can be used in methods to diagnose, or to monitor the treatment or development of, diseases or conditions of heart. In addition, compounds that are identified in the screening methods described herein, as well as PKCλ nucleic acid molecules, proteins, and antibodies themselves, can be used in methods to prevent or treat such diseases or conditions.

Specific examples of diseases or conditions of the heart that can be diagnosed, prevented, or treated according to the invention include congenital defects that result in heart malformation. These include congenital defects, such as Ebstein anomaly, which results in abnormalities of the tricuspid valve, as well as isomerism defects, which are characterized by a wide variety of abnormalities in the asymmetrical arrangement of particular organs, such as the heart, organs of the digestive tract, and the spleen, that normally occurs during development.

In right isomerism sequence, for example, which is also known as asplenia syndrome, Ivemark syndrome, and right atrial isomerism, the right side structures of the heart are duplicated on the left side of the heart, and the spleen is absent. This condition can lead to very complex and severe heart defects, such as atrioventricular septal defect (AVSD). In contrast, in left isomerism sequence, which is also known as polysplenia syndrome, the left side heart structures are duplicated and multiple small spleens may be present. This condition can lead to heart defects as well, such as heart block, which results in a slow heart beat, atrial septal defect, which is characterized by a hole between the top two heart chambers, and AVSD. With both types of isomerisms, twisting of the bowel or intestinal obstruction may result, due to the incorrect positioning of the intestines. Related defects may occur in other organs, such as the kidney.

Other diseases and conditions related to PKCλ that can be diagnosed, prevented, or treated according to the invention include those that are characterized by abnormalities in tight junctions. As is noted above, we have found that abnormalities in PKCλ (caused, e.g., by the has mutation) can lead to defects in epithelial cell-cell interactions. This is due to abnormalities in the formation of tight junctions, which play critical roles in the sealing of spaces between the individual epithelial or endothelial cells that make up sheets of these cells that line the cavities of the body (e.g., the gastrointestinal tract, blood vessels, the respiratory tract, and the urinary tract), as well as enclose and protect certain organs (e.g., the brain). These sheets of cells function as selective permeability barriers, and alteration of the permeability of these barriers, due to, e.g., a PKCλ defect, can lead to any of a number of diseases or conditions that are well known in the art. For example, increased permeability of the lining of the gastrointestinal tract can lead to Crohn's disease, acute gastroenteritis, and diarrhea. Also, defects in tight junctions can interfere with the critical functions of the blood/brain barrier or the blood/retina barrier. As an additional example, vascular permeability defects in diabetic patients can lead to conditions such as diabetic retinopathy. Additional diseases and conditions that can be diagnosed, prevented, or treated, according to the invention, include those that are associated with abnormalities in epithelial cell polarity, such as polycystic kidney disease (e.g., autosomal dominant polycystic kidney disease). Also, because we have found that abnormalities in PKCλ lead to defects in cell growth control, a role for PKCλ in cancer is indicated. Compounds that are found to modulate PKCλ activity, thus, can be used in the prevention and treatment of cancer, such as, for example, carcinomas (e.g., renal cell carcinoma), which are cancers derived from epithelial cells.

Diagnostic Methods

Nucleic acid molecules encoding PKCλ proteins, as well as polypeptides encoded by these nucleic acid molecules and antibodies specific for these polypeptides, can be used in methods to diagnose or to monitor diseases and conditions involving mutations in, or inappropriate expression of, genes encoding this protein.

The diagnostic methods of the invention can be used, for example, with patients that have a disease or condition associated with PKCλ, in an effort to determine its etiology and, thus, to facilitate selection of an appropriate course of treatment The diagnostic methods can also be used with patients who have not yet developed, but who are at risk of developing, such a disease or condition, or with patients that are at an early stage of developing such a disease or condition. Also, the diagnostic methods of the invention can be used in prenatal genetic screening, for example, to identify parents who may be carriers of a recessive mutation in a gene encoding a PKCλ protein. The methods of the invention can be used to diagnose (or to treat) the disorders described herein in any mammal, for example, in humans, domestic pets, or livestock.

Abnormalities in PKCλ that can be detected using the diagnostic methods of the invention include those characterized by, for example, (i) a gene encoding a PKCλ protein containing a mutation that results in the production of an abnormal PKCλ protein, (ii) an abnormal PKCλ polypeptide itself (e.g., a truncated protein), and (iii) a mutation in a PKCλ gene that results in production of an abnormal amount of this protein. Detection of such abnormalities can be used to diagnose human diseases or conditions related to PKCλ, such as those affecting the heart. Exemplary of the mutations in PKCλ genes is the heart and soul mutation, which is described further below.

A mutation in a PKCλ gene can be detected in any tissue of a subject, even one in which this protein is not expressed. Because of the possibly limited number of tissues in which these proteins may be expressed, for limited time periods, and because of the possible undesirability of sampling such tissues (e.g., heart tissue) for assays, it may be preferable to detect mutant genes in other, more easily obtained sample types, such as in blood or amniotic fluid samples.

Detection of a mutation in a gene encoding a PKCλ protein can be carried out using any standard diagnostic technique. For example, a biological sample obtained from a patient can be analyzed for one or more mutations (e.g., a heart and soul mutation) in nucleic acid molecules encoding a PKCλ protein using a mismatch detection approach. Generally, this approach involves polyrnerase chain reaction (PCR) amplification of nucleic acid molecules from a patient sample, followed by identification of a mutation (i.e., a mismatch) by detection of altered hybridization, aberrant electrophoretic gel migration, binding, or cleavage mediated by mismatch binding proteins, or by direct nucleic acid molecule sequencing. Any of these techniques can be used to facilitate detection of a mutant gene encoding a PKCλ protein, and each is well known in the art. For instance, examples of these techniques are described by Orita et al. (Proc. Natl. Acad. Sci. U.S.A. 86:2766-2770, 1989) and Sheffield et al. (Proc. Natl. Acad. Sci. U.S.A. 86:232-236, 1989).

As noted above, in addition to facilitating diagnosis of an existing disease or condition, mutation detection assays also provide an opportunity to diagnose a predisposition to disease related to a mutation in a PKCλ gene before the onset of symptoms. For example, a patient who is heterozygous for a gene encoding an abnormal PKCλ protein (or an abnormal amount thereof) that suppresses normal PKCλ biological activity or expression may show no clinical symptoms of a disease related to such proteins, and yet possess a higher than normal probability of developing such disease. Given such a diagnosis, a patient can take precautions to minimize exposure to adverse environmental factors, and can carefully monitor their medical condition, for example, through frequent physical examinations. As mentioned above, this type of diagnostic approach can also be used to detect a mutation in a gene encoding the PKCλ protein in prenatal screens.

While it may be preferable to carry out diagnostic methods for detecting a mutation in a PKCλ gene using genomic DNA from readily accessible tissues, as noted above, mRNA encoding this protein, or the protein itself, can also be assayed from tissue samples in which it is expressed. Expression levels of a gene encoding PKCλ in such a tissue sample from a patient can be determined by using any of a number of standard techniques that are well known in the art, including northern blot analysis and quantitative PCR (see, e.g., Ausubel et al., supra; PCR Technology: Principles and Applications for DNA Amplification, H. A. Ehrlich, Ed., Stockton Press, NY; Yap et al. Nucl. Acids. Res. 19:4294, 1991).

In another diagnostic approach of the invention, an immunoassay is used to detect or to monitor the level of a PKCλ protein in a biological sample. Polyclonal or monoclonal antibodies specific for the PKCλ protein can be used in any standard immunoassay format (e.g., ELISA, Western blot, or RIA; see, e.g., Ausubel et al., supra) to measure polypeptide the levels of PKCλ. These levels can be compared to levels of PKCλ in a sample from an unaffected individual. Detection of a decrease in production of PKCλ using this method, for example, may be indicative of a condition or a predisposition to a condition involving insufficient biological activity of the PKCλ protein.

Immunohistochemical techniques can also be utilized for detection of PKCλ protein in patient samples. For example, a tissue sample can be obtained from a patient, sectioned, and stained for the presence of PKCλ using an anti-PKCλ antibody and any standard detection system (e.g., one that includes a secondary antibody conjugated to an enzyme, such as horseradish peroxidase). General guidance regarding such techniques can be found in, e.g., Bancroft et al., Theory and Practice of Histological Techniques, Churchill Livingstone, 1982, and Ausubel et al., supra.

Identification of Molecules that can be Used to Treat or to Prevent Diseases or Conditions Associated with PKCλ

Identification of a mutation in the gene encoding PKCλ as resulting in a phenotype that results in abnormal heart growth and development facilitates the identification of molecules (e.g., small organic or inorganic molecules, antibodies, peptides, or nucleic acid molecules) that can be used to treat or to prevent diseases or conditions associated with PKCλ, as discussed above. The effects of candidate compounds on such diseases or conditions can be investigated using, for example, the zebrafish system. As is mentioned above, the zebrafish, *Danio rerio*, is a convenient organism to use in the genetic analysis of development. It has an accessible and transparent embryo, allowing direct observation of organ function from the earliest stages of development, has a short generation time, and is fecund. As discussed further below, zebrafish and other animals having a PKCλ mutation, such as the heart and soul mutation, which can be used in these methods, are also included in the invention.

In one example of the screening methods of the invention, a zebrafish having a mutation in a gene encoding the PKCλ protein (e.g., a zebrafish having the heart and soul mutation) is contacted with a candidate compound, and the effect of the compound on the development of a heart abnormality, or on the status of such an existing abnormality, is monitored relative to an untreated, identically mutant control. In a variation of this method, a zebrafish, with or without a mutation in the PKCλ gene (e.g., the has mutation), is contacted with a candidate compound in the presence of concentramide.

After a compound has been shown to have a desired effect in the zebrafish system, it can be tested in other models of heart disease, for example, in mice or other animals having a mutation in a gene encoding PKCλ. Alternatively, testing in such animal model systems can be carried out in the absence of zebrafish testing. Compounds of the invention can also be tested in animal models of cancer.

Cell culture-based assays can also be used in the identification of molecules that increase or decrease PKCλ levels or biological activity. According to one approach, candidate molecules are added at varying concentrations to the culture medium of cells expressing PKCλ mRNA. PKCλ biological activity is then measured using standard techniques. The measurement of biological activity can include the measurement of PKCλ protein and nucleic acid molecule levels.

In general, novel drugs for the prevention or treatment of diseases related to mutations in genes encoding PKCλ can be identified from large libraries of natural products, synthetic (or semi-synthetic) extracts, and chemical libraries using methods that are well known in the art. Those skilled in the field of drug discovery and development will understand that the precise source of test extracts or compounds is not critical to the screening methods of the invention and that dereplication, or the elimination of replicates or repeats of materials already known for their therapeutic activities for PKCλ, can be employed whenever possible.

Candidate compounds to be tested include purified (or substantially purified) molecules or one or more components of a mixture of compounds (e.g., an extract or supernatant obtained from cells; Ausubel et al., supra), and such compounds further include both naturally occurring or artificially derived chemicals and modifications of existing compounds. For example, candidate compounds can be polypeptides, synthesized organic or inorganic molecules, naturally occurring organic or inorganic molecules, nucleic acid molecules, and components thereof.

Numerous sources of naturally occurring candidate compounds are readily available to those skilled in the art. For example, naturally occurring compounds can be found in cell (including plant, fungal, prokaryotic, and animal) extracts, mammalian serum, growth medium in which mammalian cells have been cultured, protein expression libraries, or fermentation broths. In addition, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, FL), and PharmaMar, U.S.A. (Cambridge, Mass.). Furthermore, libraries of natural compounds can be produced, if desired, according to methods that are known in the art, e.g., by standard extraction and fractionation.

Artificially derived candidate compounds are also readily available to those skilled in the art. Numerous methods are available for generating random or directed synthesis (e.g., semi-synthesis or total synthesis) of any number of chemical compounds, including, for example, saccharide-, lipid-, peptide-, and nucleic acid molecule-based compounds. In addition, synthetic compound libraries are commercially available from Brandon Associates (Merrimack, N.H.) and Aldrich Chemicals (Milwaukee, Wis.). Libraries of synthetic compounds can also be produced, if desired, according to methods known in the art, e.g., by standard extraction and fractionation. Furthermore, if desired, any library or compound can be readily modified using standard chemical, physical, or biochemical methods. The techniques of modem synthetic chemistry, including combinatorial chemistry, can also be used (reviewed in Schreiber, Bioorganic and Medicinal Chemistry 6:1172-1152, 1998; Schreiber, Science 287: 1964-1969, 2000).

When a crude extract is found to have an effect on the development or persistence of a PKCλ-associated disease, further fractionation of the positive lead extract can be carried out to isolate chemical constituents responsible for the observed effect. Thus, the goal of the extraction, fractionation, and purification process is the careful characterization and identification of a chemical entity within the crude extract having a desired activity. The same assays described herein for the detection of activities in mixtures of compounds can be used to purify the active component and to test derivatives of these compounds. Methods of fractionation and purification of such heterogeneous extracts are well known in the art. If desired, compounds shown to be useful agents for treatment can be chemically modified according to methods known in the art.

In general, compounds that are found to activate PKCλ expression or activity may be used in the prevention or treatment of diseases or conditions of heart, such as those that are characterized by abnormal growth or development, or heart failure (also see above). Compounds that are found to modulate, e.g., block PKCλ expression or activity may be used to prevent or to treat cancer.

Animal Model Systems

The invention also provides animal model systems for use in carrying out the screening methods described above. Examples of these model systems include zebrafish and other animals, such as mice, that have a mutation (e.g., the heart and soul mutation) in a PKCλ gene. For example, a zebrafish model that can be used in the invention can include a mutation that results in a lack of PKCλ protein production or production of a truncated (e.g., by introduction of a stop codon) or otherwise altered PKCλ gene product. As a specific example, a zebrafish having the heart and soul mutation can be used (see below).

Treatment or Prevention of PKCλ-Associated Diseases or Conditions

Compounds identified using the screening methods described above can be used to treat patients that have or are at risk of developing diseases or conditions of the heart or cancer. Nucleic acid molecules encoding the PKCλ protein, as well as these proteins themselves, can also be used in such methods. Treatment may be required only for a short period of time or may, in some form, be required throughout a patient's lifetime. Any continued need for treatment, however, can be determined using, for example, the diagnostic methods described above. In considering various therapies, it is to be understood that such therapies are, preferably, targeted to the affected or potentially affected organ (e.g., the heart). Such targeting can be achieved using standard methods.

Treatment or prevention of diseases resulting from a mutated PKCλ gene can be accomplished, for example, by modulating the function of a mutant PKCλ protein. Treatment can also be accomplished by delivering normal PKCλ protein to appropriate cells, altering the levels of normal or mutant PKCλ protein, replacing a mutant gene encoding a PKCλ protein with a normal gene encoding a PKCλ protein, or administering a normal gene encoding a PKCλ protein. It is also possible to correct the effects of a defect in a gene encoding a PKCλ protein by modifying the physiological pathway (e.g., a signal transduction pathway) in which a PKCλ protein participates. in a patient diagnosed as being heterozygous for a gene encoding a mutant PKCλ protein, or as susceptible to such mutations or aberrant PKCλ expression (even if those mutations or expression patterns do not yet result in alterations in expression or biological activity of PKCλ), any of the therapies described herein can be administered before the occurrence of the disease phenotype. In particular, compounds shown to have an effect on the phenotype of mutants, or to modulate expression of PKCλ proteins, can be administered to patients diagnosed with potential or actual disease by any standard dosage and route of administration.

Any appropriate route of administration can be employed to administer a compound identified as described above, a PKCλ gene, or a PKCλ protein, according to the invention. For example, administration can be parenteral, intravenous, intra-arterial, subcutaneous, intramuscular, intraventricular, intracapsular, intraspinal, intracisternal, intraperitoneal, intranasal, by aerosol, by suppository, or oral.

A therapeutic compound of the invention can be administered within a pharmaceutically acceptable diluent, carrier, or excipient, in unit dosage form. Administration can begin before or after the patient is symptomatic. Methods that are well known in the art for making formulations are found, for example, in Remington's Pharmaceutical Sciences (18$^{th}$ edition), ed. A. Gennaro, 1990, Mack Publishing Company, Easton, Pa. Therapeutic formulations can be in the form of liquid solutions or suspensions. Formulations for parenteral administration can contain, for example, excipients, sterile water, or saline; polyalkylene glycols, such as polyethylene glycol; oils of vegetable origin; or hydrogenated napthalenes. Biocompatible, biodegradable lactide polymer, lactide/glycolide copolymer, or polyoxyethylene-polyoxypropylene copolymers can be used to control the release of the compounds. Other potentially useful parenteral delivery systems include ethylene-vinyl acetate copolymer particles, osmotic pumps, implantable infusion systems, and liposomes. For oral administration, formulations can be in the form of tablets or capsules. Formulations for inhalation can contain excipients, for example, lactose, or can be aqueous solutions containing, for example, polyoxyethylene-9-lauryl ether, glycocholate, and deoxycholate, or can be oily solutions for administration in the form of nasal drops or as a gel. Alternatively, intranasal formulations can be in the form of powders or aerosols.

To replace a mutant protein with normal protein, or to add protein to cells that do not express a sufficient amount of PKCλ or normal PKCλ, it may be necessary to obtain large amounts of pure PKCλ protein from cell culture systems in which the protein is expressed (see, e.g., below). Delivery of the protein to the affected tissue can then be accomplished using appropriate packaging or administration systems.

Gene therapy is another therapeutic approach for preventing or ameliorating diseases caused by PKCλ gene defects. Nucleic acid molecules encoding wild type PKCλ protein can be delivered to cells that lack sufficient, normal PKCλ protein biological activity (e.g., cells carrying mutations (e.g., the heart and soul mutation) in PKCλ genes). The nucleic acid molecules must be delivered to those cells in a form in which they can be taken up by the cells and so that sufficient levels of protein, to provide effective PKCλ protein function, can be produced. Alternatively, for some PKCλ mutations, it may be possible to slow the progression of the resulting disease or to modulate PKCλ protein activity by introducing another copy of a homologous gene bearing a second mutation in that gene, to alter the mutation, or to use another gene to block any negative effect.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, the full length PKCλ gene, or a portion thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107: 77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the introduction of therapeutic DNA into cells predicted to be subject to diseases involving the PKCλ protein. For example, a PKCλ nucleic acid molecule or an antisense nucleic acid molecule can be introduced into a cell by lipofection (Felgner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263: 14621, 1988; Wu et al., Journal of Biological Chemistry 264:16985, 1989), or by micro-injection under surgical conditions (Wolff et al., Science 247:1465, 1990).

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal PKCλ protein into a cultivatable cell type ex vivo (e.g., an autologous or heterologous primary cell or progeny thereof), after which the cell (or its descendants) are injected into a targeted tissue.

PKCλ cDNA expression for use in gene therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct PKCλ expression. The enhancers used can include, without limitation, those that are characterized as tissue- or cell-specific enhancers. Alternatively, if a PKCλ genomic clone is used as a therapeutic construct (such clones can be identified by hybridization with PKCλ cDNA, as described herein), regulation can be mediated by the cognate regulatory sequences or, if desired, by regulatory sequences derived from a heterologous source, including any of the promoters or regulatory elements described above.

Molecules for effecting antisense-based strategies can be employed to explore PKCλ protein gene function, as a basis for therapeutic drug design, as well as to treat PKCλ-associated diseases, such as cancer. These strategies are based on the principle that sequence-specific suppression of gene expression (via transcription or translation) can be achieved by intracellular hybridization between genomic DNA or MRNA and a complementary antisense species. The formation of a hybrid RNA duplex interferes with transcription of the target PKCλ-encoding genomic DNA molecule, or processing, transport, translation, or stability of the target PKCλ mRNA molecule.

Antisense strategies can be delivered by a variety of approaches. For example, antisense oligonucleotides or antisense RNA can be directly administered (e.g., by intravenous injection) to a subject in a form that allows uptake into cells. Alternatively, viral or plasmid vectors that encode antisense RNA (or antisense RNA fragments) can be introduced into a cell in vivo or ex vivo. Antisense effects can be induced by control (sense) sequences; however, the extent of phenotypic changes is highly variable. Phenotypic effects induced by antisense molecules are based on changes in criteria such as protein levels, protein activity measurement, and target mRNA levels.

PKCλ gene therapy can also be accomplished by direct administration of antisense PKCλ MRNA to a cell that is expected to be adversely affected by the expression of wild type or mutant PKCλ protein. The antisense PKCλ mRNA can be produced and isolated by any standard technique, but is most readily produced by in vitro transcription using an antisense PKCλ cDNA under the control of a high efficiency promoter (e.g., the T7 promoter). Administration of antisense PKCλ MRNA to cells can be carried out by any of the methods for direct nucleic acid molecule administration described above.

An alternative strategy for inhibiting PKCλ protein function using gene therapy involves intracellular expression of an anti-PKCλ protein antibody or a portion of an anti-PKCλ protein antibody. For example, the gene (or gene fragment) encoding a monoclonal antibody that specifically binds to a PKCλ protein and inhibits its biological activity can be placed under the transcriptional control of a tissue-specific gene regulatory sequence.

Another therapeutic approach included in the invention involves administration of a recombinant PKCλ polypeptide, either directly to the site of a potential or actual disease-affected tissue (for example, by injection) or systemically (for example, by any conventional recombinant protein administration technique). The dosage of the PKCλ protein depends on a number of factors, including the size and health of the individual patient but, generally, between 0.1 mg and 100 mg, inclusive, is administered per day to an adult in any pharmaceutically acceptable formulation.

In addition to the therapeutic methods described herein, involving administration of PKCλ-modulating compounds, PKCλ proteins, or PKCλ nucleic acids to patients, the invention provides methods of culturing organs in the presence of such molecules. In particular, as is noted above, a PKCλ mutation is associated with abnormal heart growth and development. Thus, culturing heart tissue in the presence of these molecules can be used to promote its growth and development. This tissue can be that which is being prepared for transplant from, e.g., an allogeneic or xenogeneic donor, as well as synthetic tissue or organs.

Synthesis of PKCλ Proteins, Polypeptides, and Polypeptide Fragments

Those skilled in the art of molecular biology will understand that a wide variety of expression systems can be used to produce recombinant PKCλ proteins. As discussed further below, the precise host cell used is not critical to the invention. The PKCλ proteins can be produced in a prokaryotic host (e.g., *E. coli*) or in a eukaryotic host (e.g., *S. cerevisiae*, insect cells, such as Sf9 cells, or mammalian cells, such as COS-1, NIH 3T3, or HeLa cells). These cells are commercially available from, for example, the American Type Culture Collection, Manassas, Va. (see also Ausubel et al., supra). The method of transformation and the choice of expression vehicle (e.g., expression vector) will depend on the host system selected. Transformation and transfection methods are described, e.g., in Ausubel et al., supra, and expression vehicles can be chosen from those provided, e.g., in Pouwels et al., Cloning Vectors: A Laboratory Manual, 1985, Supp. 1987. Specific examples of expression systems that can be used in the invention are described further as follows.

For protein expression, eukaryotic or prokaryotic expression systems can be generated in which PKCλ gene sequences are introduced into a plasmid or other vector, which is then used to transform living cells. Constructs in which full-length PKCλ cDNAs, containing the entire open reading frame, inserted in the correct orientation into an expression plasmid, can be used for protein expression. Alternatively, portions of PKCλ gene sequences, including wild type or mutant PKCλ sequences, can be inserted. Prokaryotic and eukaryotic expression systems allow various important functional domains of PKCλ proteins to be recovered, if desired, as fusion proteins, and then used for binding, structural, and functional studies, and also for the generation of antibodies.

Typical expression vectors contain promoters that direct synthesis of large amounts of mRNA corresponding to a nucleic acid molecule that has been inserted into the vector. They can also include a eukaryotic or prokaryotic origin of replication, allowing for autonomous replication within a host cell, sequences that confer resistance to an otherwise toxic drug, thus allowing vector-containing cells to be selected in the presence of the drug, and sequences that increase the efficiency with which the synthesized mRNA is translated. Stable, long-term vectors can be maintained as freely replicating entities by using regulatory elements of, for example, viruses (e.g., the OriP sequences from the Epstein Barr Virus genome). Cell lines can also be produced that have the vector integrated into genomic DNA of the cells and, in this manner, the gene product can be produced in the cells on a continuous basis.

Expression of foreign molecules in bacteria, such as *Escherichia coli*, requires the insertion of a foreign nucleic acid molecule, e.g., a PKCλ nucleic acid molecule, into a bacterial expression vector. Such plasmid vectors include several elements required for the propagation of the plasmid in bacteria, and for expression of foreign DNA contained within the plasmid. Propagation of only plasmid-bearing bacteria is achieved by introducing, into the plasmid, a selectable marker-encoding gene that allows plasmid-bearing bacteria to grow in the presence of an otherwise toxic drug. The plasmid also contains a transcriptional promoter capable of directing synthesis of large amounts of mRNA from the foreign DNA. Such promoters can be, but are not necessarily, inducible promoters that initiate transcription upon induction by culture under appropriate conditions (e.g., in the presence of a drug that activates the promoter). The plasmid also, preferably, contains a polylinker to simplify insertion of the gene in the correct orientation within the vector.

Once an appropriate expression vector containing a PKCλ gene, or a fragment, fusion, or mutant thereof, is constructed, it can be introduced into an appropriate host cell using a transformation technique, such as, for example, calcium phosphate transfection, DEAE-dextran transfection, electroporation, microinjection, protoplast fusion, or liposome-mediated transfection. Host cells that can be transfected with the vectors of the invention can include, but are not limited to, *E. coli* or other bacteria, yeast, fungi, insect cells (using, for example, baculoviral vectors for expression), or cells derived from mice, humans, or other animals. Mammalian cells can also be used to express PKCλ proteins using a virus expression system (e.g., a vaccinia virus expression system) described, for example, in Ausubel et al., supra.

In vitro expression of PKCλ proteins, fusions, polypeptide fragments, or mutants encoded by cloned DNA can also be carried out using the T7 late-promoter expression system. This system depends on the regulated expression of T7 RNA polymerase, an enzyme encoded in the DNA of bacteriophage T7. The T7 RNA polymerase initiates transcription at a specific 23 base pair promoter sequence called the T7 late promoter. Copies of the T7 late promoter are located at several sites on the T7 genome, but none are present in *E. coli* chromosomal DNA. As a result, in T7-infected *E. coli*, T7 RNA polymerase catalyzes transcription of viral genes, but not *E. coli* genes. In this expression system, recombinant *E. coli* cells are first engineered to carry the gene encoding T7 RNA polymerase next to the lac promoter. In the presence of IPTG, these cells transcribe the T7 polymerase gene at a high rate and synthesize abundant amounts of T7 RNA polymerase. These cells are then transformed with plasmid vectors that carry a copy of the T7 late promoter protein. When IPTG is added to the culture medium containing these transformed *E. coli* cells, large amounts of T7 RNA polymerase are produced. The polymerase then binds to the T7 late promoter on the plasmid expression vectors, catalyzing transcription of the inserted cDNA at a high rate. Since each *E. coli* cell contains many copies of the expression vector, large amounts of mRNA corresponding to the cloned cDNA can be produced in this system and the resulting protein can be radioactively labeled.

Plasmid vectors containing late promoters and the corresponding RNA polymerases from related bacteriophages, such as T3, T5, and SP6, can also be used for in vitro production of proteins from cloned DNA. *E. coli* can also be used for expression using an M13 phage, such as mGPl-2. Furthermore, vectors that contain phage lambda regulatory sequences, or vectors that direct the expression of fusion proteins, for example, a maltose-binding protein fusion protein or a glutathione-S-transferase fusion protein, also can be used for expression in *E. coli*.

Eukaryotic expression systems are useful for obtaining appropriate post-translational modification of expressed proteins. Transient transfection of a eukaryotic expression plasmid containing a PKCλ gene into a eukaryotic host cell allows the transient production of a PKCλ protein by the transfected host cell. PKCλ proteins can also be produced by a stably-transfected eukaryotic (e.g., mammalian) cell line. A number of vectors suitable for stable transfection of mammalian cells are available to the public (see, e.g., Pouwels et al., supra), as are methods for constructing lines including such cells (see, e.g., Ausubel et al., supra).

In one example, cDNA encoding a PKCλ protein, fusion, mutant, or polypeptide fragment is cloned into an expression vector that includes the dihydrofolate reductase (DHFR) gene. Integration of the plasmid and, therefore, integration of the heart and soul protein-encoding gene, into the host cell chromosome is selected for by inclusion of 0.01-300 µM methotrexate in the cell culture medium (Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al., supra. These methods generally involve extended culture in medium containing gradually increasing levels of methotrexate. The most commonly used DHFR-containing expression vectors are pCVSEII-DHFR and pAdD26SV(A) (described, for example, in Ausubel et al., supra). The host cells described above or, preferably, a DHFR-deficient CHO cell line (e.g., CHO DHFR-cells, ATCC Accession No. CRL 9096) are among those that are most preferred for DHFR selection of a stably transfected cell line or DHFR-mediated gene amplification.

Another preferred eukaryotic expression system is the baculovirus system using, for example, the vector pBac-PAK9, which is available from Clontech (Palo Alto, Calif.). If desired, this system can be used in conjunction with other protein expression techniques, for example, the myc tag approach described by Evan et al. (Molecular and Cellular Biology 5:3610-3616, 1985).

Once a recombinant protein is expressed, it can be isolated from the expressing cells by cell lysis followed by protein purification techniques, such as affinity chromatography. In this example, an anti-PKCλ antibody, which can be produced by the methods described herein, can be attached to a column and used to isolate the recombinant PKCλ. Lysis and fractionation of PKCλ-harboring cells prior to affinity chromatography can be performed by standard methods (see, e.g., Ausubel et al., supra). Once isolated, the recombinant protein can, if desired, be purified further by, e.g., high performance liquid chromatography (HPLC; e.g., see Fisher, *Laboratory Techniques In Biochemistry and Molecular Biology*, Work and Burdon, Eds., Elsevier, 1980).

Polypeptides of the invention, particularly short PKCλ fragments and longer fragments of the N-terminus and C-terminus of PKCλ, can also be produced by chemical synthesis (e.g., by the methods described in *Solid Phase Peptide Synthesis*, 2$^{nd}$ ed., 1984, The Pierce Chemical Co., Rockford, Ill.). These general techniques of polypeptide expression and purification can also be used to produce and isolate useful PKCλ fragments or analogs, as described herein.

PKCλ Protein Fragments

Polypeptide fragments that include various portions of PKCλ proteins are useful in identifying the domains of PKCλ that are important for its biological activities. Methods for generating such fragments are well known in the art (see, for example, Ausubel et al., supra), using the nucleotide sequences provided herein. For example, a PKCλ protein fragment can be generated by PCR amplifying a desired PKCλ nucleic acid molecule fragment using oligonucleotide primers designed based upon PKCλ nucleic acid sequences. Preferably, the oligonucleotide primers include unique restriction enzyme sites that facilitate insertion of the amplified fragment into the cloning site of an expression vector (e.g., a mammalian expression vector, see above). This vector can then be introduced into a cell (e.g., a mammalian cell; see above) by artifice, using any of the various techniques that are known in the art, such as those described herein, resulting in the production of a PKCλ protein fragment in the cell containing the expression vector. PKCλ protein fragments (e.g., chimeric fusion proteins) can also be used to raise antibodies specific for various regions of the PKCλ protein using, for example, the methods described below.

PKCλ Protein Antibodies

To prepare polyclonal antibodies, PKCλ proteins, fragments of PKCλ proteins, or fusion proteins containing defined portions of PKCλ proteins can be synthesized in, e.g., bacteria by expression of corresponding DNA sequences contained in a suitable cloning vehicle. Fusion proteins are commonly used as a source of antigen for producing antibodies. Two widely used expression systems for *E. coli* are lacZ fusions using the pUR series of vectors and trpE fusions using the pATH vectors. The proteins can be purified, coupled to a carrier protein, mixed with Freund's adjuvant to enhance stimulation of the antigenic response in an inoculated animal, and injected into rabbits or other laboratory animals. Alternatively, protein can be isolated from PKCλ-expressing cultured cells. Following booster injections at bi-weekly intervals, the rabbits or other laboratory animals are then bled and the sera isolated. The sera can be used directly or can be purified prior to use by various methods, including affinity chromatography employing reagents such as Protein A-Sepharose, antigen-Sepharose, and anti-mouse-Ig-Sepharose. The sera can then be used to probe protein extracts from PKCλ-expressing tissue fractionated by polyacrylamide gel electrophoresis to identify PKCλ proteins. Alternatively, synthetic peptides can be made that correspond to antigenic portions of the protein and used to inoculate the animals.

To generate peptide or full-length protein for use in making, for example, PKCλ-specific antibodies, a PKCλ coding sequence can be expressed as a C-terminal or N-terminal fusion with glutathione S-transferase (GST; Smith et al., Gene 67:31-40, 1988). The fusion protein can be purified on glutathione-Sepharose beads, eluted with glutathione, cleaved with a protease, such as thrombin or Factor-Xa (at the engineered cleavage site), and purified to the degree required to successfully immunize rabbits. Primary immunizations can be carried out with Freund's complete adjuvant and subsequent immunizations performed with Freund's incomplete adjuvant. Antibody titers can be monitored by Western blot and immunoprecipitation analyses using the protease-cleaved PKCλ fragment of the GST-PKCλ protein. Immune sera can be affinity purified using CNBr-Sepharose-coupled PKCλ. Antiserum specificity can be determined using a panel of unrelated GST fusion proteins.

Alternatively, monoclonal PKCλ antibodies can be produced by using, as an antigen, PKCλ isolated from PKCλ-expressing cultured cells or PKCλ protein isolated from tissues. The cell extracts, or recombinant protein extracts containing PKCλ, can, for example, be injected with Freund's adjuvant into mice. Several days after being injected, the mouse spleens can be removed, the tissues disaggregated, and the spleen cells suspended in phosphate buffered saline (PBS). The spleen cells serve as a source of lymphocytes, some of which would be producing antibody of the appropriate specificity. These can then be fused with permanently growing myeloma partner cells, and the products of the fusion plated into a number of tissue culture wells in the presence of selective agents, such as hypoxanthine, aminopterine, and thymidine (HAT). The wells can then be screened by ELISA to identify those containing cells making antibodies capable of binding to PKCλ, polypeptide fragment, or mutant thereof. These cells can then be re-plated and, after a period of growth, the wells containing these cells can be screened again to identify antibody-producing cells. Several cloning procedures can be carried out until over 90% of the wells contain single clones that are positive for specific antibody production. From this procedure, a stable line of clones that produce the antibody can be established. The monoclonal antibody can then be purified by affinity chromatography using Protein A Sepharose and ion exchange chromatography, as well as variations and combinations of these techniques. Once produced, monoclonal antibodies are also tested for specific PKCλ recognition by Western blot or immunoprecipitation analysis (see, e.g., Kohler et al., Nature 256:495, 1975; Kohler et al., European Journal of Immunology 6:511, 1976; Kohler et al., European Journal of Immunology 6:292, 1976; Hammerling et al., In Monoclonal Antibodies and T Cell Hybridomas, Elsevier, New York, N.Y., 1981; Ausubel et al., supra).

As an alternate or adjunct immunogen to GST fusion proteins, peptides corresponding to relatively unique hydrophilic regions of PKCλ can be generated and coupled to keyhole limpet hemocyanin (KLH) through an introduced C-terminal lysine. Antiserum to each of these peptides can be similarly affinity-purified on peptides conjugated to BSA, and specificity tested by ELISA and Western blotting using peptide conjugates, and by Western blotting and immunoprecipitation using PKCλ, for example, expressed as a GST fusion protein.

Antibodies of the invention can be produced using PKCλ amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson et al., CABIOS 4:181, 1988. These fragments can be generated by standard techniques, e.g., by PCR, and cloned into the pGEX expression vector. GST fusion proteins can be expressed in *E. coli* and purified using a glutathione-agarose affinity matrix (Ausubel et al., supra). To generate rabbit polyclonal antibodies, and to minimize the potential for obtaining antisera that is non-specific, or exhibits low-affinity binding to PKCλ, two or three fusions are generated for each protein, and each fusion is injected into at least two rabbits. Antisera are raised by injections in series, preferably including at least three booster injections.

In addition to intact monoclonal and polyclonal anti-PKCλ antibodies, the invention features various genetically engineered antibodies, humanized antibodies, and antibody fragments, including F(ab')2, Fab', Fab, Fv, and sFv fragments. Truncated versions of monoclonal antibodies, for example, can be produced by recombinant methods in which plasmids are generated that express the desired monoclonal antibody fragment(s) in a suitable host. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also included in the invention (Green et al., Nature Genetics 7:13-21, 1994).

Ladner (U.S. Pat. Nos. 4,946,778 and 4,704,692) describes methods for preparing single polypeptide chain antibodies. Ward et al., Nature 341:544-546, 1989, describes the preparation of heavy chain variable domains, which they term "single domain antibodies," and which have high antigen-binding affinities. McCafferty et al., Nature 348:552-554, 1990, shows that complete antibody V domains can be displayed on the surface of fd bacteriophage, that the phage bind specifically to antigen, and that rare phage (one in a million) can be isolated after affinity chromatography. Boss et al., U.S. Pat. No. 4,816,397, describes various methods for producing immunoglobulins, and immunologically functional fragments thereof, that include at least the variable domains of the heavy and light chains in a single host cell. Cabilly et al., U.S. Pat. No. 4,816,567, describes methods for preparing chimeric antibodies.

Use of PKCλ Antibodies

Antibodies to PKCλ can be used, as noted above, to detect PKCλ or to inhibit the biological activities of PKCλ. For example, a nucleic acid molecule encoding an antibody or portion of an antibody can be expressed within a cell to inhibit PKCλ function. In addition, the antibodies can be coupled to compounds, such as radionuclides and liposomes, for diagnostic or therapeutic uses. Antibodies that inhibit the activity of a PKCλ polypeptide described herein can also be useful in preventing or slowing the development of a disease caused by inappropriate expression of a wild type or mutant PKCλ gene.

Detection of PKCλ Gene Expression

As noted, the antibodies described above can be used to monitor PKCλ gene expression. In situ hybridization of RNA can be used to detect the expression of PKCλ genes. RNA in situ hybridization techniques rely upon the hybridization of a specifically labeled nucleic acid probe to the cellular RNA in individual cells or tissues. Therefore, RNA in situ hybridization is a powerful approach for studying tissue- and temporal-specific gene expression. In this method, oligonucleotides, cloned DNA fragments, or antisense RNA transcripts of cloned DNA fragments corresponding to unique portions of PKCλ genes are used to detect specific mRNA species, e.g., in the tissues of animals, such as mice, at various developmental stages. Other gene expression detection techniques are known to those of skill in the art and can be employed for detection of PKCλ gene expression.

Identification of Additional PKCλ Genes

Standard techniques, such as the polymerase chain reaction (PCR) and DNA hybridization, can be used to clone PKCλ gene homologues in other species and PKCλ-related genes in humans. PKCλ-related genes and homologues can be readily identified using low-stringency DNA hybridization or low-stringency PCR with human PKCλ probes or primers. Degenerate primers encoding human PKCλ or human PKCλ-related amino acid sequences can be used to clone additional PKCλ-related genes and homologues by RT-PCR.

Construction of Transgenic Animals and Knockout Animals

Characterization of PKCλ genes provides information that allows PKCλ knockout animal models to be developed by homologous recombination. Preferably, a PKCλ knockout animal is a mammal, most preferably a mouse. Similarly, animal models of PKCλ overproduction can be generated by integrating one or more PKCλ sequences into the genome of an animal, according to standard transgenic techniques. Moreover, the effect of PKCλ mutations (e.g., dominant gene mutations) can be studied using transgenic mice carrying mutated PKCλ transgenes or by introducing such mutations into the endogenous PKCλ gene, using standard homologous recombination techniques.

A replacement-type targeting vector, which can be used to create a knockout model, can be constructed using an isogenic genomic clone, for example, from a mouse strain such as 129/Sv (Stratagene Inc., LaJolla, Calif.). The targeting vector can be introduced into a suitably derived line of embryonic stem (ES) cells by electroporation to generate ES cell lines that carry a profoundly truncated form of a PKCλ gene. To generate chimeric founder mice, the targeted cell lines are injected into a mouse blastula-stage embryo. Heterozygous offspring can be interbred to homozygosity. PKCλ knockout mice provide a tool for studying the role of PKCλ in embryonic development and in disease. Moreover, such mice provide the means, in vivo, for testing therapeutic compounds for amelioration of diseases or conditions involving PKCλ-dependent or a PKCλ-effected pathway.

Use of PKCλ as a Marker for Stem Cells of the Heart

As PKCλ is expressed in cells that give rise to the heart during the course of development, it can be used as a marker for stem cells of the heart. For example, PKCλ can be used to identify, sort, or target such stem cells. A pool of candidate cells, for example, can be analyzed for PKCλ expression, to facilitate the identification of heart stem cells, which, based on this identification can be separated from the pool. The isolated stem cells can be used for many purposes that are known to those of skill in this art. For example, the stem cells can be used in the production of new organs, in organ culture, or to fortify damaged or transplanted organs.

Experimental Results

Concentramide Specifically Modulates a Biological Pathway Involved in Heart Patterning Zebrafish embryos have recently been shown to be amenable to high-throughput screening to identify small molecules that perturb developmental processes (Peterson et al., Proc. Natl. Acad. Sci. U.S.A. 97:12965-12969, 2000). In one such screen, we exposed developing zebrafish embryos to small molecules from a large, diverse chemical library. Visual inspection of the transparent embryos was used to identify small molecules that affect the global patterning of the heart. One of these small molecules is a biaryl compound containing an acrylamide moiety that we call concentramide (FIG. 1A), originally identified as library number 32P6 (Peterson et al., supra).

Figure 2:
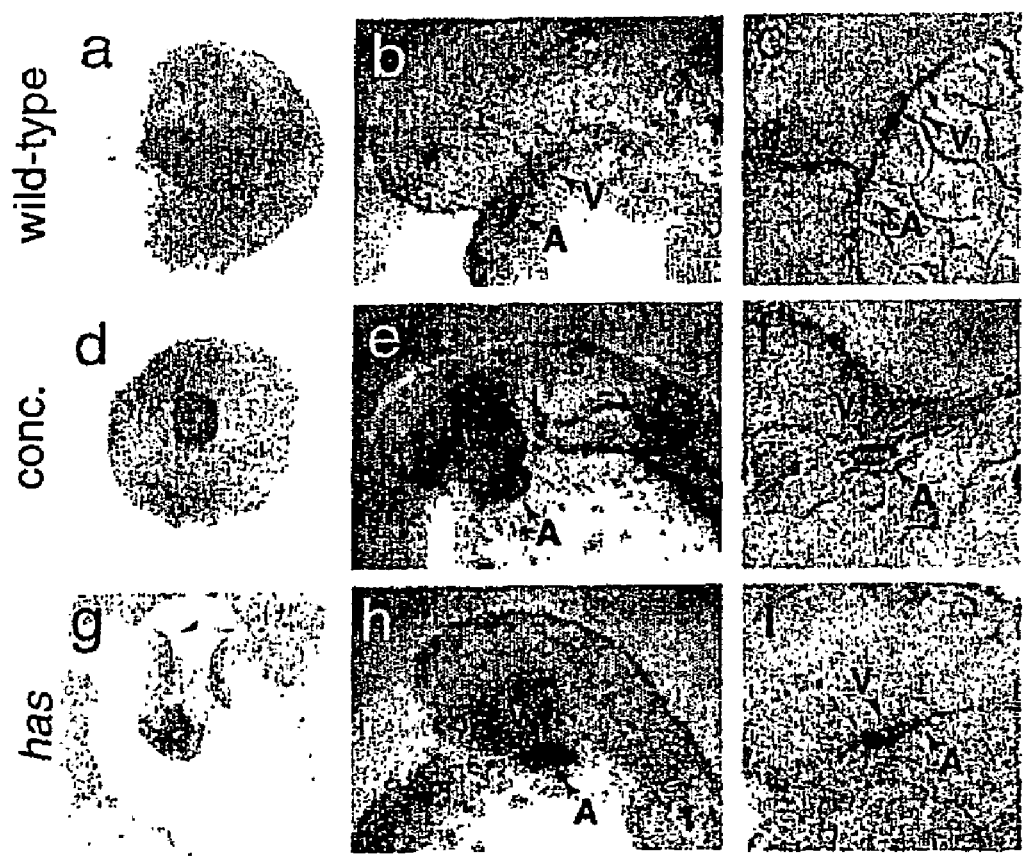
FIG. 2 shows that hearts from has mutant embryos phenocopy hearts from concentramide-treated embryos. In situ hybridization was performed with wild-type (FIGS. 2A-2C), concentramide-treated (FIGS. 2D-2F), and has (FIGS. 2G-2I) embryos. The expression pattern of cardiac myosin light chain 2 (cmlc2) is shown for embryos 24 hpf (FIGS. 2A, 2D, and 2G) and 30 hpf (FIGS. 2B, 2E, and 2H). The relative locations of atrium (A) and ventricle (V) were confirmed by 7 µm sagital sections of embryos in which the ventricle was prestained blue by in situ hybridization to ventricle-specific myosin heavy chain (vmhc), followed by staining of the atrium brown with the atrium-specific antibody S46 (FIGS. 2C, 2F, and 2I). The view is dorsal, anterior up in FIGS. 2A, 2D, and 2G. The view is lateral, anterior to the left in all other frames.

Normally, by 24 hours post-fertilization (hpf) the heart tube assembles in the midline, with the atrium anterior to the ventricle and slightly displaced towards the left (FIG. 2A), and blood flow is driven from atrial to ventricular end, first by persistalsis and then by sequential chamber contractions. By 30 hpf, the chambers are clearly demarcated (FIG. 2B, using cardiac myosin light chain 2, cmlc2, to label both chambers) and express different genes, as shown in FIG. 2C (ventricle-specific myosin heavy chain and atrial-specific antibody S46).

Embryos exposed to concentramide develop compact hearts that do not sustain a circulation. It appears that both the atrium and ventricle form and beat in a coordinated manner in these fish, but that the ventricle forms in the center of the atrium, as shown in FIGS. 2E and 2F. The result is a heart in which the atrium and ventricle form two concentric rings, the inner ring composed of the ventricle and the outer ring composed of the atrium. From the dorsal view, the heart looks like a bullseye (FIG. 2D), and from the lateral view, it looks like an inverted mushroom, in which the ventricle forms the stalk of the mushroom and the atrium surrounds and covers the ventricle like a mushroom cap (FIG. 1B).

Several observations suggest that concentramide is a highly specific modulator of a particular molecular pathway critical to heart patterning. Concentramide is very potent, with an $ED_{50}$ of about 2 nM. More importantly, higher doses of concentramide do not appear to cause additional side effects. Concentramide causes virtually the same phenotype when used at a concentration of 6 μM as it does when used at a concentration of 6 nM, suggesting that it modulates a specific molecular target at least 1,000 times more potently than it modulates other proteins affecting visible developmental processes. The effect of concentramide on cardiovascular development does not appear to be a result of general cytotoxicity. Development of concentramide-treated embryos is not delayed relative to untreated siblings, and no increase in cell death is apparent. Concentramide also has no effect on the rate of proliferation of yeast or bromodeoxyuridine incorporation in mammalian cells. Given the potency of concentramide, its phenotypic reproducibility over a broad concentration range, and the rarity of the phenotype it produces (none of the >2000 other small molecules screened generates a similar phenotype), we conclude that concentramide is a specific modulator of a biological pathway responsible for heart patterning.

A Time Window for Concentramide Effects

One advantage of small molecules over genetic mutations in studying a developmental process is that small molecules allow the process to be modulated with much greater temporal control. Small molecules can be added or washed away at any time during development, whereas genetic mutations are generally present throughout development. This temporal control afforded by small molecules facilitates the identification of critical periods for developmental processes.

To identify the developmental stage at which concentramide disrupts heart patterning decisions, we added concentramide to the water of developing embryos at various times. As shown in FIG. 1C, embryos treated at any time prior to 14 hpf exhibit the concentric chamber morphology at 24 hpf, while embryos treated after 17 hpf exhibit wild-type heart morphology at 24 hpf. Repeating the experiment with more precise staging revealed that concentramide must be present before the 14-somite stage (approximately 15 hpf) to induce the concentric chamber morphology. Therefore, a developmental event occurring at the 14-somite stage is critical for heart patterning and is disrupted by the small molecule concentramide.

The Hearts of Concentramide-treated Embryos Phenocopy Heart-and-soul Mutants

Heart-and-soul (has) is a mutation isolated in our large-scale genetic screen. The hearts of homozygous has mutant embryos are small. We find here that, like those of concentramide-treated embryos, the hearts of has mutant embryos have ventricular tissue within the atrium (FIGS. 2G and 2H). They manifest radial sequential contractions of the atrium, then the ventricle. The has mutant embryos, however, also manifest defects in many tissues including the retina, kidney, gut, and brain. These defects are not present in concentramide-treated embryos. The brains of concentramide-treated embryos develop abnormally, but treating embryos between 9 and 14 hpf eliminates this brain defect, while preserving the concentric heart chamber phenotype (FIG. 1C). Therefore, the heart phenotypes of concentramide-treated and has mutant embryos are very similar, but concentramide-treated embryos appear to have fewer developmental defects elsewhere, and the cardiac specificity of the phenotype can be increased further by controlling the timing of concentramide treatment.

Heart-and-soul Encodes an Atypical PKCλ

Figure 3:
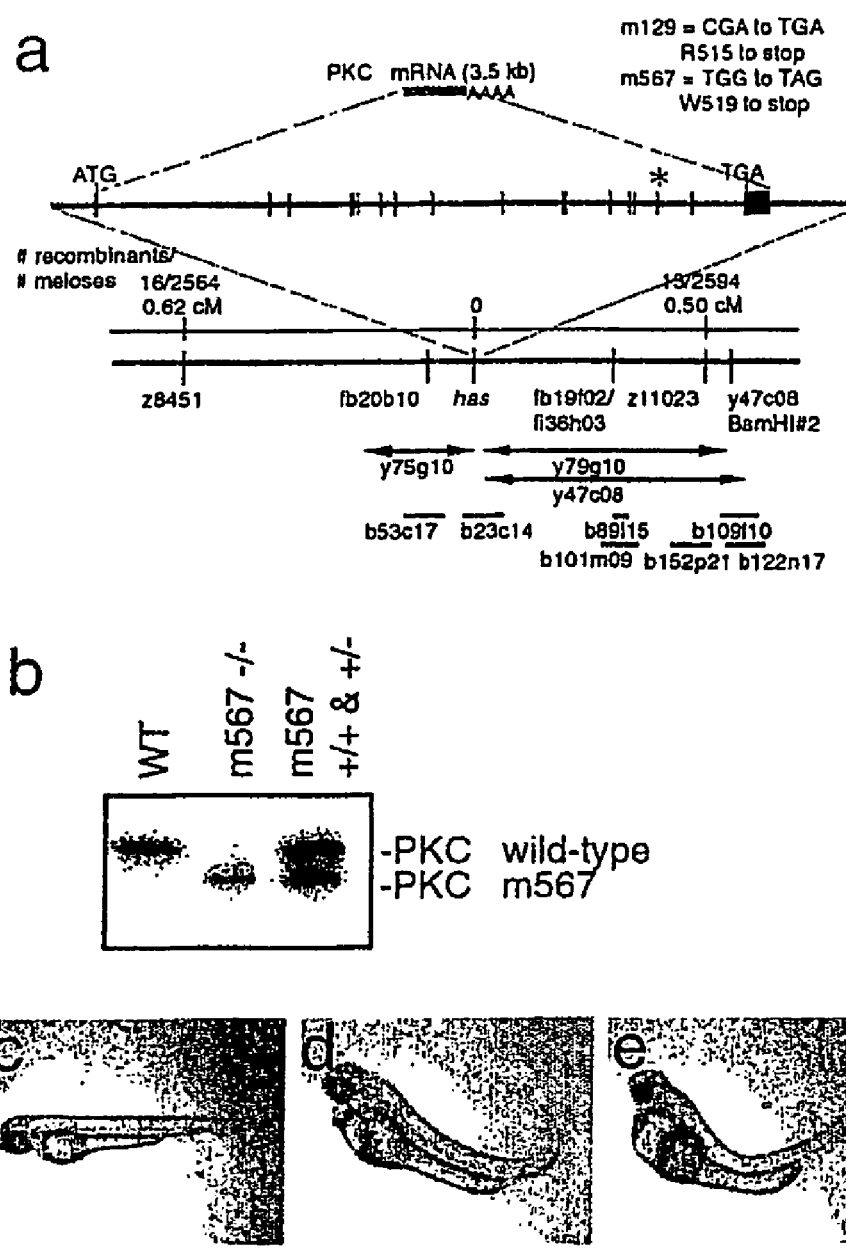
FIG. 3A is a map of the has interval with genomic structure of the zebrafish PKCλ gene. YAC and BAC clones are indicated by addresses beginning with "y" and "b." The BAC clone 23c14 was sequenced to determine the entire genomic structure of the has gene. From the partial sequence of the BACs listed, a preliminary transcript map of the region was determined (see Table 1). The zebrafish PKCλ gene comprises 18 exons represented by vertical lines. The site of the mutations associated with the m129 and m567 alleles is indicated with an asterisk.
FIG. 3B is an anti-PKCλ western blot of protein extracts from wild-type embryos (WT), has mutant embryos (m567 −/−), and siblings of has mutant embryos (m567 +/+ and +/−).
FIGS. 3C-3E show that antisense disruption of PKCλ expression phenocopies the has mutation. Wild-type embryos (3C), has embryos (3D), and wild-type embryos injected with a PKCλ antisense morpholino oligomer (3E) were photographed live 2 days postfertilization.

Given the phenotypic similarities between hearts from has and concentramide-treated embryos, we reasoned that cloning the has gene might provide molecular insight about the process of heart patterning. Furthermore, cloning of has might allow us to determine whether has and concentramide influence heart patterning through similar or distinct mechanisms. We mapped has by linkage analysis with zebrafish SSR markers (Michelmore et al., Proc. Natl. Acad. Sci. U.S.A. 88:9828-9832, 1991; Knapik et al., Nat. Genet. 18:338-343, 1998; Shimoda et al., Genomics 58:219-232, 1999) and AFLP (Vos et al., Nucleic Acids Res. 23:4407-4414, 1995) to an interval flanked by markers z8451 and z11023 of approximately 1.1 cM (FIG. 3A). These were used to initiate a walk using YACs and BACs, which proceeded by end-cloning, refined mapping, and ultimately sequencing. Genes identified as candidates for the mutation were assayed by in situ analysis and for cDNA polymorphism by RT-PCR of wild-type and mutant RNA pools. The genes contained within the BACs are shown in Table 1. The gene assignments are based on BLASTX alignments.

TABLE 1

Candidate genes identified within the heart-and-soul interval

| BAC address | identified genes (GenBank accession#) |
|---|---|
| 109f10/122n17 | KIAA0670 protein/acinus (NP_055792) |
| | membrane-type 1 metalloproteinase precursor (AAD13803) adaptin, gamma (NP_001119) |
| | KIAA1416 protein, novel Helicase C-terminal domain and SNF2 N-termina domains containing protein, similar to KIAA0308 (CAB57836) ZPC domain containing protein 2 (AAD38907) zinc finger protein sal (AAB51127) cerebellin 1 precursor (NP_004343) RING finger protein (AAB05873) |
| 152p21 | unknown (NP_056541) |
| 89i15 | precerebellin-like protein (AAF04305) |
| 23c14 | PKCλ |
| | transforming protein sno-N - chicken (I51298) |
| 53c17 | no genes detected by BLASTX (mostly repetitive) |

By sequencing PKCλ from wild type and mutant embryos, we confirmed that both has alleles harbor mutations in the PKCλ coding sequence. The mutation in the m567 allele causes a premature stop codon after amino acid 518, and the mutation in the m129 allele causes a premature stop codon after amino acid 514 (FIG. 3A). We determined the complete genomic structure of the zebrafish PKCλ gene by shotgun sequencing of BAC 23c14. It is comprised of 18 exons spanning approximately 45 kb. We find PKCλ mRNA to be expressed in a broad range of tissues.

The C-terminal truncation of PKCλ does not appear to destabilize the protein, as truncated protein is detected by western blot analysis of mutant embryos (FIG. 3B). However, truncation might be predicted to eliminate a domain essential for PKCλ function, given that C-terminal truncation of PKCα or PKCβ renders these related kinases catalytically inactive (Riedel et al., J. Cell. Biochem. 52:320-329, 1993; Riedel et al., Mol. Cell. Biol. 13:4728-4735, 1993). In order to confirm the role of PKCλ 20 mutation in the phenotype, we injected antisense morpholino oligomers complementary to the PKCλ translational start site. These injections phenocopy the mutation entirely.

The injected embryos are indistinguishable at the gross morphological level from the genetic mutants (FIG. 3C), supporting the idea that loss of the C-terminal 70 amino acids is sufficient to eliminate gene function.

The Integrity of Epithelia is Affected by PKCλ Mutation, but not by Treatment with Concentramide PKCλ belongs to the large PKC family of kinases and, with PKCζ, is classified as an 'atypical' PKC (Mellor et al., Biochem. J. 332:281-292, 1998). The presumptive ortholog of PKCλ in *C. elegans*, PKC-3, colocalizes with Par3 and Par6 at the anterior pole of the one-cell embryo (Tabuse et al., supra; Hung et al., Development 126:127-135, 1999). PKC-3 is necessary for establishment of embryonic polarity, and inactivation of PKC-3 leads to mislocalization of the Par genes and a symmetrical first cell division. *Drosophila* possesses only one atypical PKC (DaPKC), which also associates with a Par3-like protein (Bazooka) and is implicated in control of cell polarity (Wordarz et al., supra). DaPKC mutants exhibit disordered epithelial layering, irregular cell shapes, and loss of epithelial cell polarity, believed to be due to defects in cell adhesion. In vertebrate cells, PKCλ and PKCζ both localize to epithelial tight junctions and associate with a Par3-like protein (ASIP) (Joberty et al., Nat. Cell Biol. 2:531-539, 2000; Suzuki et al., J. Cell Biol. 152:1183-1196, 2001; Lin et al., Nat. Cell Biol. 2:540-547, 2000; Izumi et al., J. Cell Biol. 143:95-106, 1998). We therefore examined whether the has mutation and concentramide treatment perturb epithelial patterning and tight junctions, focusing upon the retina and the kidney.

The neural retina arises from an epithelial sheet that is bordered by the lens on the basal surface and by a second epithelial sheet (the retinal pigmented epithelium, RPE) on the apical surface (Schmitt et al., J. Comp. Neurol. 344:532-542, 1994). Prior to cell differentiation, the nuclei of the neuroepithelial cells migrate between the apical and basal surfaces of the epithelium. During M-phase, cell nuclei localize to the apical surface, adjacent to the neighboring RPE (Sauer, J. Comp. Neurol. 62:377-405, 1935). Beginning at about 30 hpf, these neuroepithelial cells exit the cell cycle and differentiate into one of seven distinct cell types (Altshuler et al., "Specification of Cell Type in the Vertebrate Retina," In Development of the Visual System, Lam et al. (Eds.), The MIT Press, Cambridge, Mass. 37-58, 1991; Dowling, "The Retina," Belknap Press, Cambridge, Mass., 1987). Each cell type then migrates to a specific layer in the retina, resulting in a highly organized, laminar pattern (see FIG. 4A).

Figure 4:
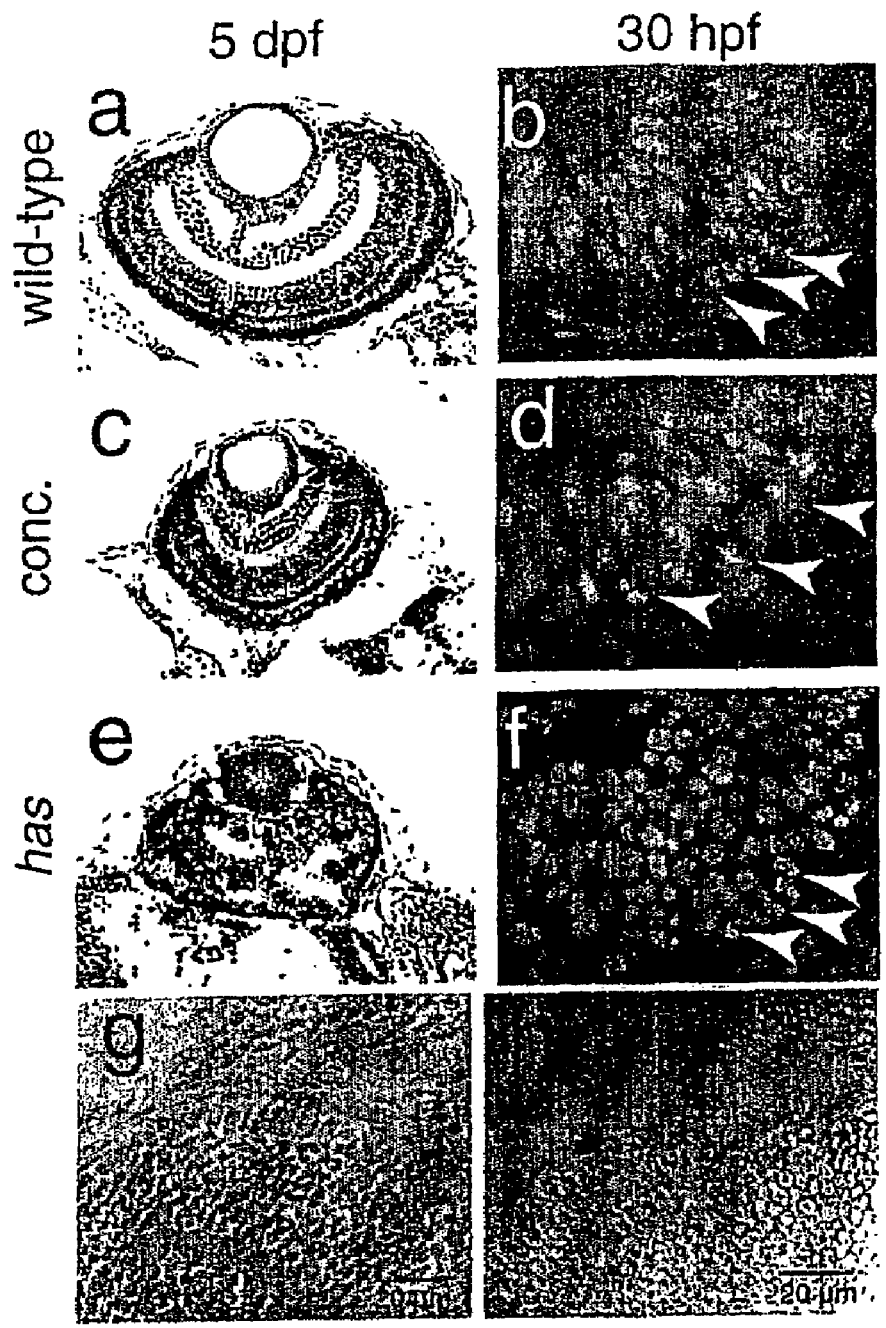
FIG. 4 shows that PKCλ is required for lamination, cell polarity, and epithelial cell-cell interaction in the retina. Transverse 5 µm sections of wild-type (FIGS. 4A-4B), concentramide-treated (FIGS. 4C-4D), and has (FIGS. 4E-4F) embryos were stained with hematoxylin-eosin 5 days postfertilization (FIGS. 4A, 4C, and 4E) or with dapi 30 hpf (FIGS. 4B, 4D, and 4F). Arrowheads indicate mitotic nuclei. Zonula occludens-1 localization in the retina is shown by 5 µm transverse sections following staining of wild-type (FIG. 4G) or has (FIG. 4H) embryos with an anti-ZO-1 antibody.

The has mutation causes disruption of the layering of the neural retina and patchy loss of the RPE (FIG. 4E). These defects resemble those noted previously in zebrafish bearing the mutations oko meduzy (ome) and mosaic eyes (moe) (Jensen et al., Development 128:95-105, 2001; Malicki et al., Development 126:1235-1246, 1999). In has mutants, the severity of laminar disruption correlates with the position and degree of RPE discontinuity, suggesting that the RPE epithelial defect causes or exacerbates that of the neural retina. This would be concordant with the evidence that a normal RPE is critical to lamination (Raymond et al., Curr. Biol. 5:1286-1295, 1995; Vollmer et al., Neurosci. Lett. 48:191-196, 1984) and the fact that the retinal epithelium of has mutants manifests at least one attribute of proper apical-basal polarity in that the majority of the mitotic nuclei localize correctly to the apical surface of the neuroepithelium (FIGS. 4B, 4D, and 4F; 89% of M-phase nuclei from has embryos localize to the apical surface versus 97% of nuclei from wild-type embryos). As a marker of tight junctions, we examined immunoreactive zonula occludens (ZO-1), an integral tight junction protein, and find it to be mislocalized (FIGS. 4G and 4H). Therefore, loss of adhesion between RPE cells may be a cause of retinal mispatterning in has mutants. Notably, retinas from concentramide-treated embryos do not exhibit defects in cell polarity (FIG. 4D), RPE continuity, or lamination (FIG. 4C)

Figure 5:
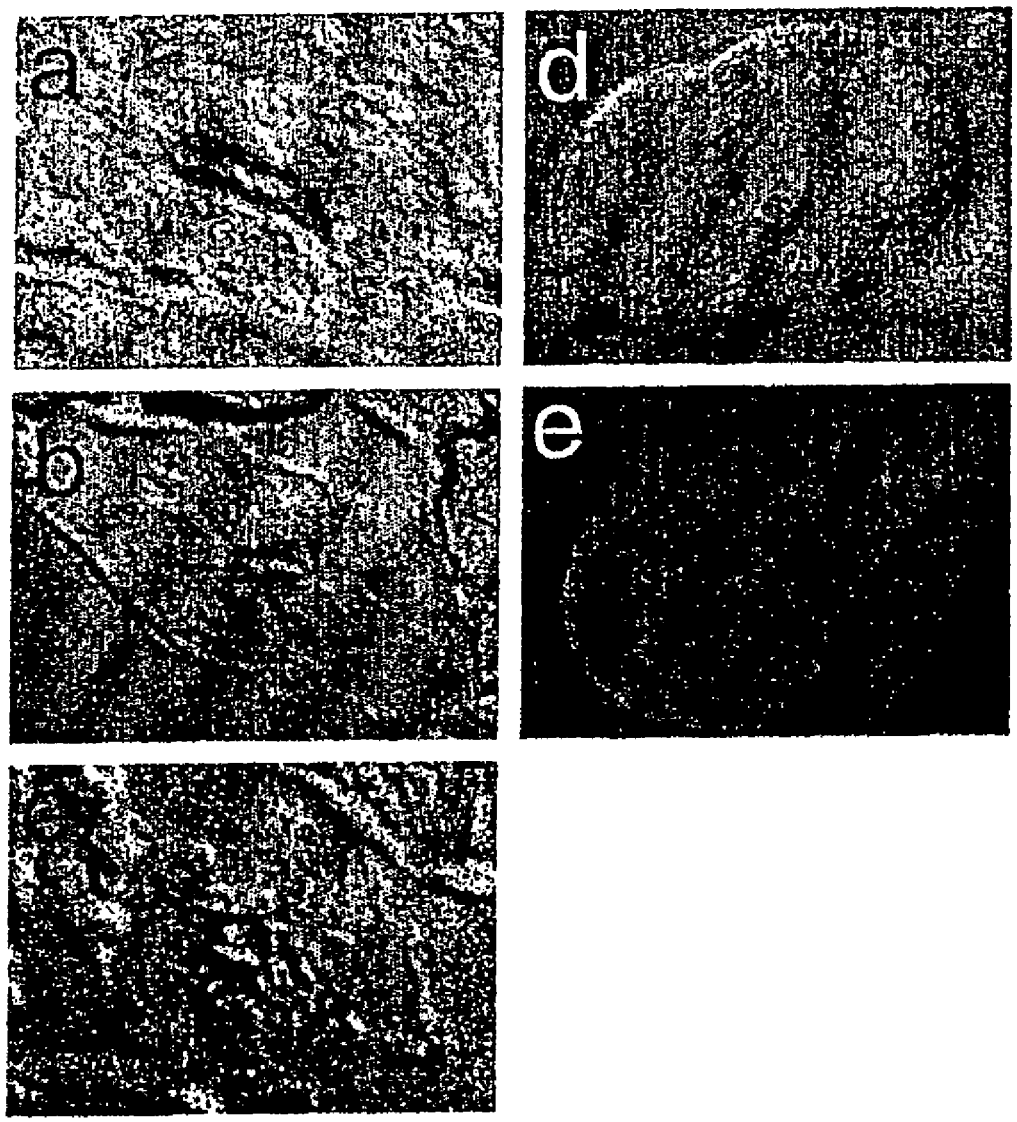
FIG. 5 shows the effects of PKCλ inactivation and concentramide treatment on polarity of the zebrafish kidney and the C. elegans embryo. An apical kidney marker (3G8) was used to stain kidneys of wild-type (FIG. 5A), concentramide-treated (FIG. 5B), and has (FIG. 5C) embryos. Transverse 2 µm sections of the pronephric duct are shown.

The developing kidney is another structure composed of highly polarized epithelial cells. We examined the distribution of apical and basolateral proteins in the kidneys of wild-type, has, and concentramide-treated embryos. As in the retina, cell polarity appeared to be largely conserved in has kidneys (FIGS. 5A-5C). The has kidneys did, however, exhibit irregularities in the shapes of epithelial cells and occasional gaps between cells, consistent with a defect in epithelial cell adhesion. We did not observe these defects in embryos exposed to concentramide.

Given the differences between has and concentramide-treated embryos with regard to epithelial sheet integrity in the retina and the kidney, it is unlikely that concentramide functions through the same mechanism as the has mutation, namely the inactivation of PKCλ. To examine this further, we tested the effect of concentramide on early development of the *C. elegans* embryo. In *C. elegans*, inactivation of the PKCλ ortholog PKC-3 via RNA interference (RNAi) results in the loss of polarized localization of the Par proteins and loss of asymmetry during the first cell division (Tabuse et al., supra). Embryos treated with high concentrations of concentramide retain proper localization of Par2 to the posterior pole and undergo a normally asymmetric first cell division (FIGS. 5D and 5E). Treated embryos exhibit cytolinetic defects and fail to complete development, suggesting that the absence of an asymmetry defect is not due to problems with compound penetration. Therefore, although concentramide treatment and PKCλ inactivation both result in similar heart patterning phenotypes, concentramide does not appear to inactivate zebrafish PKCλ or its nematode ortholog.

The Molecular Target of Concentramide is Involved in AP Patterning

Figure 6:
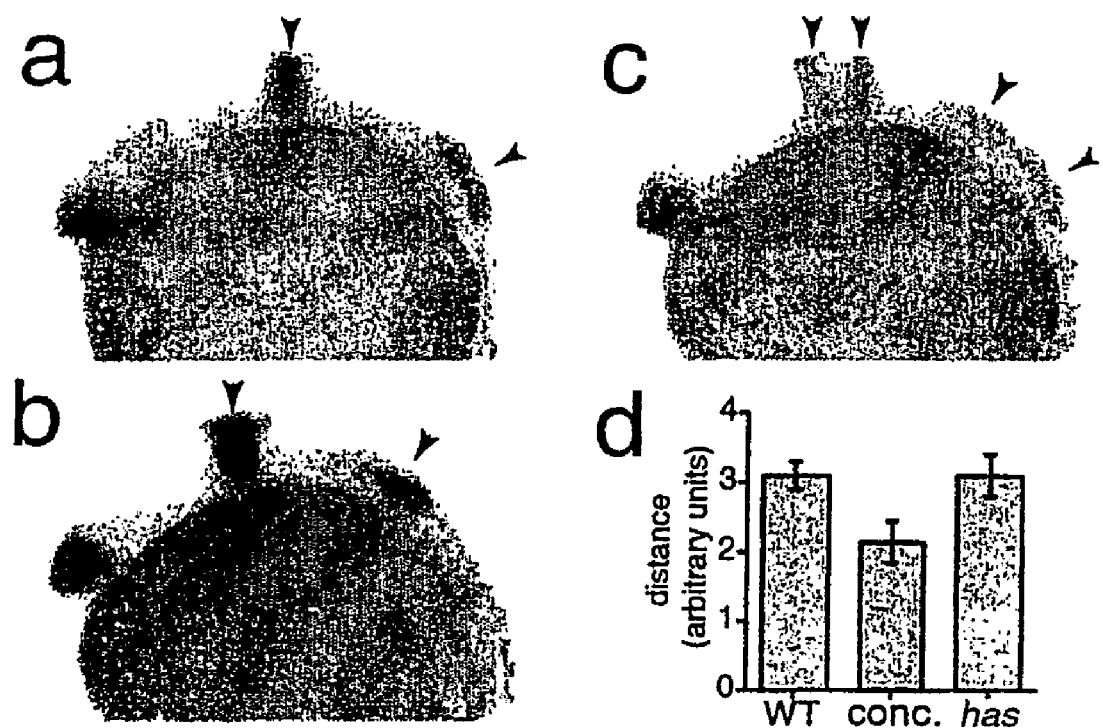
FIG. 6 shows alterations in anterior-posterior patterning after treatment with concentramide.

If the molecular target of concentramide does not affect the continuity of epithelial sheets as PKCλ does, by what sort of process might it influence heart patterning? Treatment with concentramide appears to affect the relative positions of several anatomical structures along the anterior-posterior (AP) axis. For example, the distance between Pax2.1-expressing cells in the eyes and at the midbrain/hindbrain boundary is reduced in concentramide-treated embryos (FIGS. 6A-6C). Perhaps more significantly, the cardiac myosin light chain 2 (cmlc2)-expressing cells of the heart field are shifted rostrally in concentramide-treated embryos at the 18-somite stage (FIG. 6D). The distance between the anterior edge of the cmlc2-expressing field and the anterior extreme of the embryo is about 40 percent greater in wild-type embryos (3.1+/−0.2 arbitrary units, n=8) than in concentramide-treated embryos (2.2+/−0.3 arbitrary units, n=12). The position of the heart field in has mutants (3.1+/−0.3 arbitrary units, n=12) does not differ significantly from the wild-type position. Therefore, the molecular target of concentramide appears to play a role in AP patterning.

PKCλ and the Target of Concentramide Both Influence the Fusion Order of Heart Primordia PKCλ and the molecular target of concentramide appear to act via distinct cellular mechanisms, but modulation of either results in a very similar change in the patterning of the heart. To identify the commonalties between the two mechanisms that allow such similar mispatterning of the heart, we took advantage of the temporal control with which small molecules can modulate biological processes. As described above, we determined that embryos must be treated with concentramide at or prior to the 14-somite stage to cause formation of the ventricle within the atrium. From this observation, we conclude that a critical heart patterning process is initiated shortly after the 14-somite stage, and perturbation of this process results in the concentric chamber phenotype observed in both has and concentramide-treated embryos. This allowed us to focus our search for commonalties between has and concentramide-treated embryos to this critical time period.

The generation of the primitive heart tube is accomplished by midline coalescence of the bilateral cardiac primordial sheets. In the zebrafish, this coalescence first generates a single midline cone, with its base on the yolk (Fishman et al., supra; Yelon et al., Dev. Biol. 214:23-37, 1999). Subsequently, the cone tilts to assume a midline A-P orientation with the pre-ventricular end posterior, later to swing anteriorly as yolk is resorbed.

Figure 7:
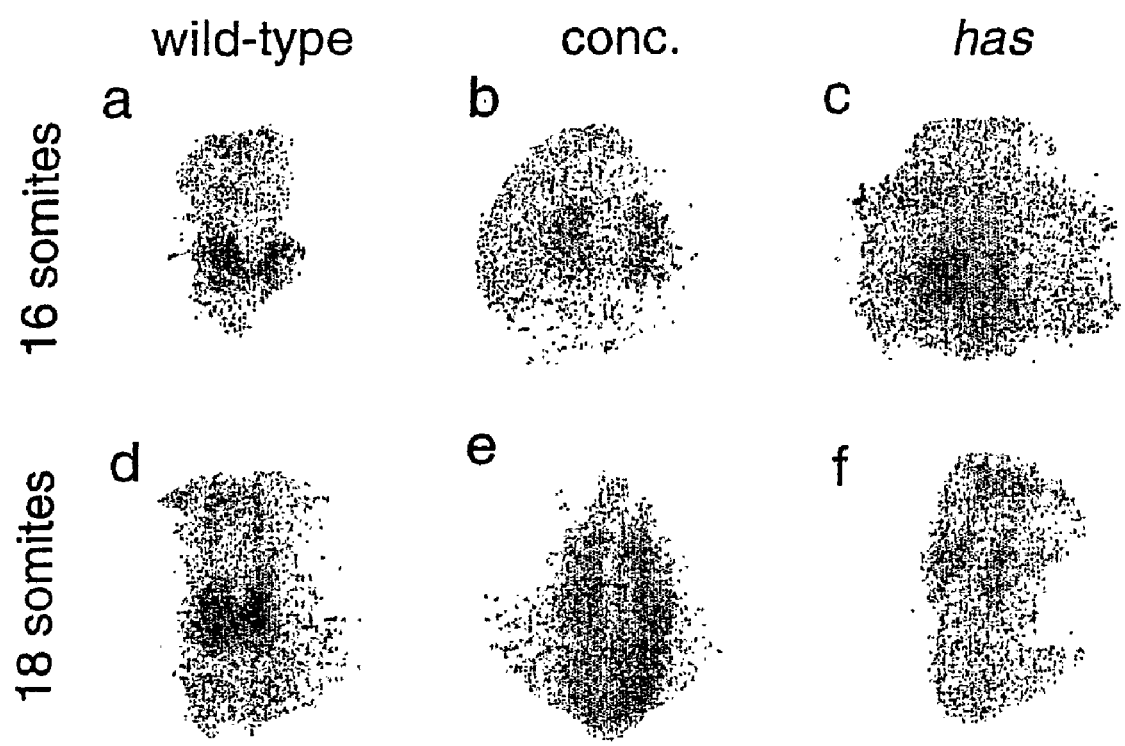
FIG. 7 shows the order of anterior and posterior heart field fusion. Dorsal views of cmlc2 expression at the 16-somite (FIGS. 7A-7C) and 18-somite (FIGS. 7D-7F) stages. Expression patterns for wild-type (FIG. 7A and FIG. 7D), concentramide-treated (FIG. 7B and FIG. 7E), and has (FIGS. 7C and 7F) embryos are shown. Anterior is up.
Figure 8:
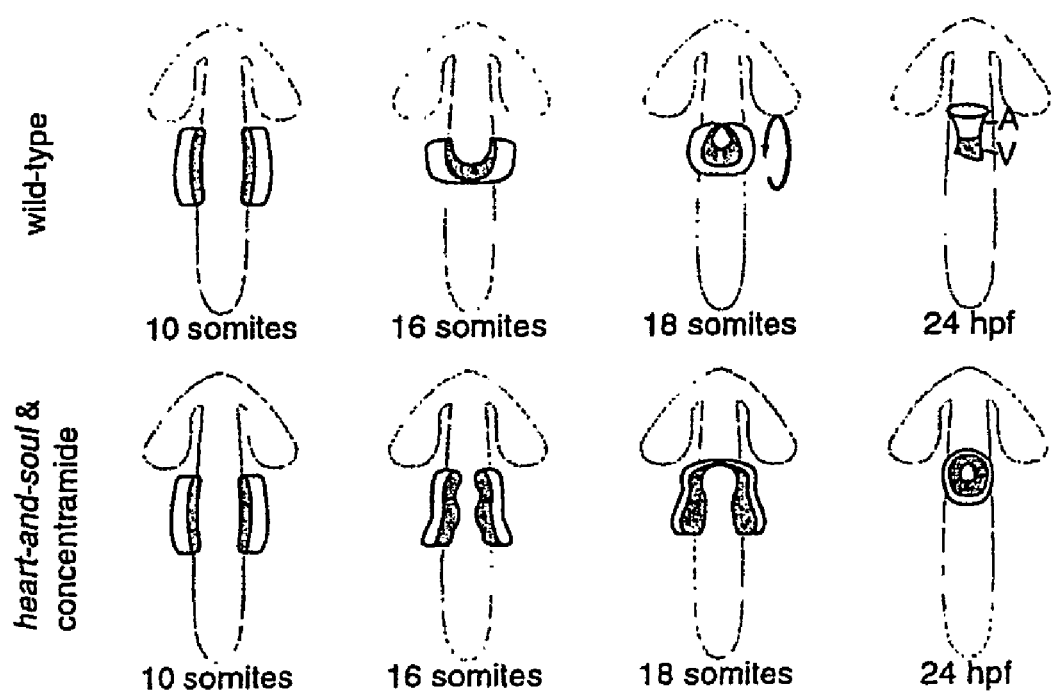
FIG. 8 is a schematic representation of a model for chamber patterning in the zebrafish heart. Normally, the bilateral primordia of the heart field converge and fuse first at the posterior end, followed by the anterior end to form a cone. The cone then rotates to orient atrial precursors toward the anterior and ventricular precursors toward the posterior in an extended heart tube. In concentramide-treated and has mutant embryos, the fusion order of the ends of the heart field is reversed, proceeding from the anterior to the posterior end. Rotation of the cone is blocked, preventing formation of the heart tube and causing the concentric heart chamber phenotype. Presumptive atrial precursor cells are colored red, ventricular precursor cells are colored blue. Views are dorsal; anterior is up.

We find that normally the generation of the midline cone does not occur uniformly around the cone's circumference, but rather progresses from posterior to anterior, with posterior regions merging at the 16-somite stage and anterior at the 18-somite stage. This step is perturbed by both concentramide and the has mutation. In both has mutant embryos and concentramide-treated embryos, there is a failure to merge the posterior ends (FIGS. 7A-7C). Even by the 18-somite stage, when the anterior ends of the primordia begin to fuse normally, the posterior ends remain separated in the has and concentramide-treated embryos (FIGS. 7D-7F). Eventually, the posterior ends do fuse in has and concentramide-treated embryos, just before emergence of the concentric chambered heart. Thus, a critical patterning decision occurs at about the 16-somite stage that regulates the fusion order of the anterior and posterior ends of the heart field. This process can be blocked either by inactivation of PKCλ or by modulating the target of concentramide.

Thus, in summary, we have defined a key step in heart formation by its perturbation with a small molecule and a mutation. This step involves the proper alignment of the two cardiac chambers, just as the primitive heart tube assembles. Two perturbants—the small molecule concentramide and the has mutation—both elicit a previously undescribed chamber malalignment, in which the ventricle forms inside of the atrium. This means that establishment of the cardiocyte cell fates is largely accomplished, but the higher order assembly of chamber structure is disrupted.

Experimental Methods

Small Molecule Treatment

Zebrafish were maintained at 28.5° C. as described (Westerfield, "The Zebrafish Book, Guide for the Laboratory Use of Zebrafish (*Danio rerio*)," Univ. of Oregon Press, Eugene 1995). Unless specified otherwise, embryos were treated prior to gastrulation by adding concentramide to the water at a final concentration of 34 nM from a 34 μM stock solution in DMSO.

Whole-mount in Situ Hybridization and Immunohistochemistry

Digoxigenin-labeled antisense RNA probes were generated by ill vitro transcription for cmlc2 (Yelon et al., supra), vmhc (Yelon et al., supra), and pax2.1 (Krauss et al., Development 113:1193-1206, 1991). In situ hybridization was carried out as described (Oxtoby et al., Nucleic Acids Res. 21:1087-1095, 1993). For whole-mount immunohistochemistry, embryos were fixed in 4% paraformaldehyde in phosphate-buffered saline (S46 and 3G8) or 80% methanol, 20% dimethyl sulfoxide (α-ZO-1), permeablized in acetone for 30 minutes at −20° C. (3G8), blocked with 5% fetal bovine serum, and incubated with the antibodies S46, 3G8 (Vize et al., Dev. Biol. 171:531-540, 1995), or α-ZO-1. An anti-mouse-horseradish peroxidase conjugate was used as secondary antibody for S46 and 3G8, and an Alexa 488-labeled anti-mouse secondary antibody was used for α-ZO-1 staining.

Histology

Fixed embryos were dehydrated, embedded in plastic (JB4, Polysciences, Inc.), and sectioned at 2-7 μm. Retinal sections were stained with hematoxylin-eosin or dapi.

Cloning of Has

Embryos were separated into mutant and wild-type pools based on phenotypic analysis. Genomic DNA was isolated from individual embryos by incubation in DNA isolation buffer overnight at 50° C. (DNA isolation buffer: 10 mM Tris-HCl, pH 8.3; 50 mM KCl; 0.3% Tween-20; 0.3% Nonidet P40; 0.5 mg/ml proteinase K). Proteinase K was inactivated prior to PCR setup by heating samples to 98° C. for 10 minutes. PCR reactions were performed using diluted genomic DNA as described (Knapik et al., Development 123: 451-460, 1996).

RNA was isolated (RNeasy columns, Qiagen) from pools of wild-type and mutant embryos to generate cDNA for RT-PCR analysis (SMART RACE cDNA amplification kit, Clontech). Fragments were then subcloned into PCRII-TOPO (Invitrogen). PCR primers were synthesized based on sequence from an EST for PKCλ (fc69h04, GenBank accession# AI883774) and genomic sequence (Genome Systems, BAC clone address 23c14), and used to sequence the entire PKCλ coding region and 3'UTR.

Genomic clones were isolated by PCR analysis of DNA pools from BAC (Genome Systems) and YAC (Research Genetics) libraries using primer sets for the linked markers z11023 and z8451. YAC end sequence was determined as described (Zhong et al., Genomics 48:136-138, 1998). BAC ends were sequenced directly using SP6 and T7 primers, and BACs 53c17, 89i15, and 152p21 were subcloned by shotgun cloning of partial AluI digested fragments into pBluescript.

For the complete sequencing of BACs, a hydroshear was used to produce fragments of 2-3 kb in length. These fragments were then blunt-end ligated into pGEM5 (Promega) and sequenced using an ABI3700 to generate approximately five-fold coverage. The sequence was assembled using the Phred/Phrap/Consed programs (Gordon et al., Genome Res. 8:195-202, 1998; Ewing et al., Genome Res. 8:186-194, 1998; Ewing et al., Genome Res. 8:175-185, 1998).

Western Blotting

Groups of 25 embryos were lysed in 0.5% Triton X100 in phosphate-buffered saline. Lysates were clarified by centrifugation and separted by 10% sodium dodecyl sulfate polyacrylamide gel electrophoresis. Western blotting was performed using an α-PKCλ rabbit polyclonal antibody (Santa Cruz Biotechnology, Inc.).

Morpholino Injection

An antisense morpholino oligonucleotide of sequence 5'-CTGTCCCGCAGCGTGGGCATTATGG-3' (SEQ ID NO:6) (GeneTools, LLC) was dissolved at a concentration of 100 aM in 1× Danieau's buffer (5 mM Hepes pH 7.6, 58 mM NaCl, 0.7 mM KCl, 0.6 mM Ca $(NO_3)_2$, 0.4 mM $MgSO_4$). One nL of this solution or 1× Danieau's buffer was injected into each 1-4 cell embryo before allowing the embryos to develop at 28.50° C.

*C. elegans* Development

*C. eleganis* strain KK871 (par-2::GFP) was maintained at 25° C. For each sample, 10-15 adult worms were soaked in 80 μL M9 medium containing 34 μM concentramide, 0.25% dimethyl sulfoxide for 30-60 minutes. Worms were then cut open with a scalpel, and embryos were mounted on 2% agarose pads with coverslips. Embryos were allowed to develop at 25° C. before being photographed live.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it is to be understood that it is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the appended claims.

What is claimed is:

1. A method of determining whether a human test subject has, or is at risk of developing, a heart disease or condition related to Protein Kinase C λ, said method comprising analyzing a nucleic acid molecule of a sample from the test subject to determine whether the test subject has a mutation in a gene encoding human Protein Kinase C λ, wherein said gene encoding said Protein Kinase C λ encodes the sequence of SEQ ID NO:5, and the presence of a mutation indicates that said test subject has, or is at risk of developing, a heart disease or condition related to Protein Kinase C λ.

2. The method of claim 1, wherein said gene encoding human Protein Kinase C λ comprises the sequence of SEQ ID NO:4.

3. The method of claim 1, wherein said heart disease or condition is associated with epithelial-epithelial cell interactions or epithelial cell polarity.

4. The method of claims 2, wherein said heart disease or condition is associated with epithelial-epithelial cell interactions or epithelial cell polarity.

5. The method of claim 1, wherein said mutation results in a carboxyl terminal truncation of Protein Kinase C λ.

6. The method of claim 2, wherein said mutation results in a carboxyl terminal truncation of Protein Kinase C λ.

7. The method of claim 3, wherein said mutation results in a carboxyl terminal truncation of Protein Kinase C λ.

8. The method of claim 4, wherein said mutation results in a carboxyl terminal truncation of Protein Kinase C λ.

9. The method of claim 1, wherein said mutation is the heart and soul mutation.

10. The method of claim 2, wherein said mutation is the heart and soul mutation.

11. The method of claim 3, wherein said mutation is the heart and soul mutation.

12. The method of claim 4, wherein said mutation is the heart and soul mutation.

13. The method of claim 5, wherein said mutation is the heart and soul mutation.

14. The method of claim 6, wherein said mutation is the heart and soul mutation.

15. The method of claim 7, wherein said mutation is the heart and soul mutation.

16. The method of claim 8, wherein said mutation is the heart and soul mutation.

* * * * *